(12) United States Patent
Randad et al.

(10) Patent No.: US 6,613,764 B1
(45) Date of Patent: Sep. 2, 2003

(54) ASPARTIC PROTEASE INHIBITORS

(75) Inventors: Ramnarayan S. Randad, Frederick, MD (US); John W. Erickson, Frederick, MD (US); Michael A. Eissenstat, Frederick, MD (US); Lucyna Lubkowska, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/868,775

(22) PCT Filed: Jan. 6, 2000

(86) PCT No.: PCT/US00/00265
§ 371 (c)(1),
(2), (4) Date: Sep. 28, 2001

(87) PCT Pub. No.: WO00/40558
PCT Pub. Date: Jul. 13, 2000

Related U.S. Application Data

(60) Provisional application No. 60/114,868, filed on Jan. 6, 1999.

(51) Int. Cl.[7] .................. A61K 31/5377; C07D 413/02
(52) U.S. Cl. .................. 514/235.8; 514/256; 514/318; 544/123; 544/129; 544/316
(58) Field of Search ............... 544/316, 123, 544/129; 514/256, 235.8, 318; 546/193, 209

(56) References Cited

U.S. PATENT DOCUMENTS

| 5,475,027 A | 12/1995 | Talley et al. |
| 5,502,060 A | 3/1996 | Thompson et al. |
| 5,635,523 A | 6/1997 | Kempf et al. |
| 5,703,076 A | 12/1997 | Talley et al. |
| 5,728,718 A | 3/1998 | Randad et al. |
| 5,763,464 A | 6/1998 | Randad et al. |
| 5,914,332 A | 6/1999 | Sham et al. |

FOREIGN PATENT DOCUMENTS

| WO | WO 96 04232 A | 2/1996 |
| WO | WO 96 19437 A | 6/1996 |
| WO | WO 97/21685 | * 6/1997 |

OTHER PUBLICATIONS

Apers, S. et al., "Separation of a triterpenoid saponin mixture from Maesa lanceolata: semipreparative reversed–phase wide pore high performance liquid chromatography with temperature control", *Journal of Pharmaceutical and Biomedical Analysis*, 1998, 18:4,5, 737–743.

El–On, J. et al., Topical Treatment of New and Old World cutaneous leishmaniasis in experimental animals, *Trans. Roy. Soc. Trop. Med. Hyg.*, 1987, 81, 734–737.

Sindambiwe, J. et al., "Evaluation of biological activity of triterpenoid saponins from Maesa lanceolata", *Journal of Natural Products*, May, 1998, 61:5, 585–590.

Sindambiwe, J. et al., "Triterpenoid saponins from Maesa lanceolata", *Phytochemistry*, 1996, 41:1, 269–277.

Meek et al., *J. Enzyme Inhibition*, 6(1), 65–98 (Jan. 1992).

Meek et al., *Nature*, 343(6253), 90–92 (Jan. 1990).

Moore et al., *Perspect. Drug Dis. Design*, 1, 85–108 (1993).

Norbeck et al., *Ann. Reports Med. Chem.*, 26, 141–150 (1991).

Otto et al., *PNAS USA*, 90, 7543–7547 (1993).

Plattner et al., *Drug Discovery Technologies*, Clark et al., eds., Ellish Horwood, Chichester, England, 92–126 (1990).

Randad et al., *Bioorganic & Medicinal Chemistry Letters*, 4(9), 1471–1480 (1996).

Randad et al., *Bioorganic & Medicinal Chemistry Letters*, 5(15), 1707–1712 (1995).

Randad et al., *Bioorganic & Medicinal Chemistry Letters*, 5(21), 2557–2562 (1995).

Rich et al., *J. Med. Chem*, 33, 1285–1288 (1990).

Roberts et al., *Science*, 248, 358–361 (1990).

Sham et al., *Antimicrobial Agents and Chemotherapy*, 42(1), 3218–3224 (1998).

Sham et al., *J. Med. Chem.*, 39, 392–397 (1996).

Silva et al., *Aspartic Proteinases*, 51, 363–373, New York (1998).
Silva et al., *Proc. Nat. Acad. Sci. USA*, 93, 10034–10039 (Sep. 1996).
Tomasselli et al., *Int. J. Chem. Biotechnology*, 6, 6–27 (1991).
Tong et al., *Structure*, 3(1), 33–40 (1995).
Vacca et al., *J. Med. Chem.*, 34(3), 1225–1228 (Mar. 1991).
Weislow et al., *J. National Cancer Inst.*, 81, 577 (Apr. 1989).
Bhat et al., *Structural Biology*, 1(8), 552–556 (Aug. 1994).
Bold et al., *J. Med. Chem.*, 41, 3387–3401 (1998).
De Clerq et al., *J. Med. Chem.*, 38, 2491–2517 (1995).
Erickson et al., *Science*, 249, 527–533 (1990).
Fässler et al., *J. Med. Chem.*, 39, 3203–3216 (1996).
Ghosh et al., *Bioorganic & Medicinal Chemistry Letters*, 8, 687–690 (Mar. 1998).
Ghosh et al., *J. Medicinal Chemistry*, 36(2), 292–294 (Jan. 1993).
Gulnik et al., *FEBS Letters*, 413, 379–384 (1997).
Gulnik et al., *J. Mol. Biol.*, 227, 265–270 (1992).
Ho et al., *J. Virology*, 68(3), 2016–2020 (Mar. 1994).
Huff et al., *J. Med. Chem.*, 34(8), 2305–2314 (Aug. 1991).
Hurst et al., *Drugs*, 60(6), 1371–1379 (2000).
Kageyama et al., *Antimicrob. Agents Chemother.*, 37, 810–817 (Apr. 1993).
Kageyama et al., *Antimicrob Agents Chemother.*, 36, 926–933 (May 1992).
Kalish et al., *Bioorganic & Medicinal Chemistry Letters*, 5(7), 727–732 (1995).
Kaplan et al., *PNAS USA*, 91, 5597–5601 (1994).
Kempf et al., *J. Med. Chem.*, 41(4), 602–617 (1998).
Kempf et al., *J. Med. Chem.*, 36, 320–330 (1993).
Kempf et al., *J. Med. Chem.*, 33, 2687–2689 (1990).
Kramer et al., *Science*, 231, 1580–1584 (1996).
Lehr et al., *J. Med. Chem.*, 39, 2060–2067 (1996).
McQuade et al., *Science*, 247, 454–456 (1990).

* cited by examiner

*Primary Examiner*—Joseph K. McKane
*Assistant Examiner*—Golam M. M. Shameem
(74) *Attorney, Agent, or Firm*—Leydig, Voit & Mayer, Ltd.

(57) ABSTRACT

The present invention provides a compound of formula (I) wherein a, b, c, d, and e, are $R^7$, $OR^7$, $SR^7$, $NR^7R^8$, $NHCOR^7$, $CO_2R^7$, CN, $NO_2$, $NH_2$, $N_3$, or a halogen. $R^7$ and $R^8$ are H or alkyl, $R^1$ and $R^2$ are H or alkyl, and $R^3$ is a non-aromatic substituent. Substituent A is OH, $NH_2$, or SH. Substituents B and $B^1$ include amide and sulfonamide groups, which can be cyclic, acyclic, or amino acid derivatives. Alternatively, B and R' together with the nitrogen to which they are bonded, and/or B' and $R^2$ together with the nitrogen to which they are bonded, define a heterocycle. The present invention further provides a pharmaceutical composition that includes a carrier and a therapeutically effective amount of at least one compound of the present invention. The present invention further provides therapeutic methods that include administering a therapeutically effective amount of at least one compound of the present invention

31 Claims, 7 Drawing Sheets

ASPARTIC PROTEASE INHIBITORS

This application is a 371 of PCT/US00/00265 Jan. 6, 2000 which claims benefit of Ser. No. 60/114,868 Jan. 6, 1999.

TECHNICAL FIELD OF THE INVENTION

The present invention relates to aspartic protease inhibitors, to compositions containing them, and to therapeutic methods of using them.

BACKGROUND OF THE INVENTION

A number of serious diseases, including infectious diseases, and even certain types of cancer, utilize proteolytic enzymes in physiological functions that play a critical role in their life cycles. Aspartic proteases are among the proteolytic enzymes that have been identified in this connection. In order to combat diseases which utilize aspartic proteases in critical aspects of their life cycles, aggressive efforts have been undertaken to develop aspartic protease inhibitors particularly over the last decade. Recent efforts in this area have primarily focused in the treatment or prevention of acquired immune deficiency syndrome (AIDS). AIDS is a fatal disease, reported cases of which have increased dramatically within the past several years. Estimates of reported cases in the very near future also continue to rise dramatically.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct families of HIV have been described to date, namely HIV-1 and HIV-2. The acronym HIV will be used herein to refer to HIV viruses generically.

Specifically, HIV is known to exert a profound cytopathic effect on the CD4+ helper/inducer T-cells, thereby severely compromising the immune system. HIV infection also results in neurological deterioration and, ultimately, in the death of the infected individual.

The field of viral chemotherapeutics has developed in response to the need for agents effective against retroviruses, in particular HIV. For example anti-retroviral agents, such as 3'-azido-2',3'-ideoxythymidine (AZT), 2'3'-dideoxycytidine (ddC), and 2'3'-dideoxyinosine (ddI) are known to inhibit reverse transcriptase. There also exist antiviral agents that inhibit transactivator protein. Nucleoside derivatives, such as AZT, are currently available for antiviral therapy. Although very useful, the utility of AZT and related compounds is limited by toxicity and insufficient therapeutic indices for fully adequate therapy.

Retroviral protease inhibitors also have been identified as a class of anti-retroviral agents. Retroviral protease is an aspartic protease that processes polyprotein precursors into viral structural proteins and replicative enzymes. This processing is essential for the assembly and maturation of fully infectious virions. Accordingly, the design of such aspartic protease inhibitors remains an important therapeutic goal in the treatment of AIDS.

The use of HIV protease inhibitors, in combination with agents that have different antiretroviral mechanisms (e.g., AZT, ddI and ddT), also has been described. For example, synergism against HIV-1 has been observed between certain $C_2$ symmetric HIV inhibitors and AZT (Kageyama et al., *Antimicrob. Agents Chemother.*, 36, 926–933 (1992)).

Numerous classes of potent peptidic inhibitors of protease have been designed using the natural cleavage site of the precursor polyproteins as a starting point. These inhibitors typically are peptide substrate analogs in which the scissile $P-P_1'$ amide bond has been replaced by a non-hydrolyzable isostere with tetrahedral geometry (Moore et al, *Perspect. Drug Dis. Design*, 1, 85 (1993); Tomasselli et al., *Int. J. Chem. Biotechnology*, 6 (1991); Huff, *J. Med. Chem.*, 34, 2305 (1991); Norbeck et al., *Ann. Reports Med. Chem.*, 26, 141 (1991); and Meek, *J. Enzyme Inhibition*, 6, 65 (1992)). Although these inhibitors are effective in preventing the retroviral protease from functioning, the inhibitors suffer from some distinct disadvantages. Generally, peptidomimetics often make poor drugs, due to their potential adverse pharmacological properties, i.e., poor oral absorption, poor stability and rapid metabolism (Plattner et al, *Drug Discovery Technologies*, Clark et al., eds., Ellish Horwood, Chichester, England (1990)).

The design of the HIV-1 protease inhibitors based on the transition state mimetic concept has led to the generation of a variety of peptide, derivatives highly active against viral replication in vitro (Erickson et al, *Science*, 249, 527–533 (1990); Kramer et al., *Science*, 231, 1580–1584 (1986); McQuade et al., *Science*, 247, 454–30 456 (1990); Meek et al., *Nature* (London), 343, 90–92 (1990); and Roberts et al., *Science*, 248, 358–361 (1990)). These active agents contain a non-hydrolyzable, dipeptidic isostere, such as hydroxyethylene (McQuade et al., supra; Meek et al., *Nature* (London), 343, 90–92 (1990); and Vacca et al., *J. Med. Chem.*, 34, 1225–1228 (1991).) or hydroxyethylamine (Ghosh et al., *Bioorg. Med. Chem. Lett.*, 8, 687–690 (1998); Ghosh et al., *J. Med. Chem.*, 36, 292–295 (1993)); Rich et al., *J. Med. Chem.*, 33, 1285–1288 (1990); and Roberts et al., *Science*, 248, 358–361 (1990)) as an active moiety that mimics the putative transition state of the aspartic protease-catalyzed reaction.

Two-fold ($C_2$) symmetric inhibitors of HIV protease represent another class of potent HIV protease inhibitors on the basis of the three-dimensional symmetry of the enzyme active site (Erickson et al. (1990), supra). Typically, however, the usefulness of currently available HIV protease inhibitors in the treatment of AIDS has been limited by relatively short plasma half-life, poor oral bioavailability, and the technical difficulty of scale-up synthesis (Meek et al. (1992), supra).

In a continuing effort to address the problem of short plasma half-life and poor bioavailability, new HIV protease inhibitors have been identified. For example, HIV protease inhibitors incorporating the 2,5-diamino-3,4-disubstituted-1,6-diphenylhexane isostere are described in U.S. Pat. No. 5,728,718 (Randad et al.). See also WO 96/19437. HIV protease inhibitors, which incorporate the hydroxyethylamine isostere, are described in U.S. Pat. No. 5,502,060 (Thompson et al.), U.S. Pat. No. 5,703,076 (Talley et al.), and 5,475,027 (Talley et al.). HIV protease inhibitors that incorporate a 2,5-diamino-1,6-diphenylhexane isostere are described in WO 96/04232, U.S. Pat. No. 5,635,523, Kempf et al., *J. Med. Chem.*, 41, 602–617 (1998) and Sham et al., *Antimicrob Agents Chemother.*, 42, 3218–3224 (1998).

The emergence of mutant strains of HIV, in which the protease is resistant to the $C_2$ symmetric inhibitors, also presents a serious challenge in the treatment and prevention of AIDS (Otto et al., *PNAS USA*, 90, 7543 (1993); Ho et al., J. Virology, 68, 2016–2020 (1994); and Kaplan et al., *PNAS USA*, 91, 5597–5601 (1994)). In one study, the most abundant mutation found in response to a $C_2$ symmetry based inhibitor was Arg to Gln at position 8 (R8Q), which strongly affects the $S_3/S_{3'}$ subsite of the protease binding domain.

Other mutant viruses have been identified, for example, in which the amino acid at position 84 of the retroviral protease has mutated from isoleucine into valine (84V), and in which the amino acid at position 32 of the retroviral protease has mutated to include valine (84V). Double mutants, for example, 82F/84V also have been identified. Thus, it is desirable to identify new aspartic protease inhibitors in the continuing effort to combat AIDS, and to address the problems emerging with the rise of mutant HIV strains.

Aspartic proteases also have been implicated in the life cycle of other serious infectious diseases, for example, Malaria. Malaria is one of the worlds most devastating diseases, afflicting several hundred million people a year, and killing an estimated two million of those infected, mostly children. The etiologic agent is a parasitic protozoan of the genus Plasmodium, which causes disease in its intraerythrocytic phase. A prominent feature of its development inside red blood cells is the degradation of hemoglobin. During its relatively short life cycle, the malaria-causing parasite consumes nearly all of the host's hemoglobin, generating amino acids for its own growth and maturation. The degradation of the host's hemoglobin, which is a vast catabolic process, involves a series of proteases, two of which have been identified as aspartic proteases termed "plasmepsins." The structure of plasmepsin II has recently been elucidated on the basis of diffraction data. Silva et al., *Aspartic Proteinases*, 51, pp. 363–373, New York (1998).

Although potent plasmepsin inhibitors have been identified, their ability to inhibit the malarial parasite in culture is very limited, possibly due to the inability of the inhibitors to penetrate the cellular structure sufficiently to inhibit plasmepsin in the microorganism itself. See, e.g., Silva et al., *Proc. Nat. Acad. Sci. USA*, 93, pp. 10034–10039, September 1996 (Biochemstry). Metabolism of the inhibitor by the microorganism also may be a factor. Thus, it remains a challenge to identify new plasmepsin inhibitors that are potent and also are effective against the malarial parasite in culture.

Aspartic proteases also have been implicated in essential pathways related to cancer. For example, elevated levels of cathepsin D, an aspartic protease, in primary breast cancer tissues has been correlated with increased risk of metastasis and shorter relapse-free survival in breast cancer patients. See, e.g., Gulnik et al., *J. Mol. Biol.*, 227, 265–270 (1992). Increased levels of secretion of cathepsin D in breast cancer is due to both over overexpression of the gene and altered processing of the protein. High levels of cathepsin D and other proteases may degrade the extracellular matrix and thereby promote the escape of cancer cells to the lymphatic and circulatory system and enhance the invasion of new tissues. Most deaths incurred from cancer are due to its metastatic spread to secondary organs. It is therefore desirable to identify cathepsin D inhibitors as potential therapeutics for the prevention or treatment of cancer.

In view of the foregoing problems, there exists a need for new aspartic protease inhibitors, pharmaceutical compositions, and therapeutic methods of using aspartic protease inhibitors. The present invention provides such aspartic protease inhibitors, pharmaceutical compositions, and therapeutic methods of using them. These and other advantages of the present invention, as well as additional inventive features, will be apparent from the description of the invention provided herein.

BRIEF SUMMARY OF THE INVENTION

The present invention provides an aspartic proteinase-inhibiting compound of the formula:

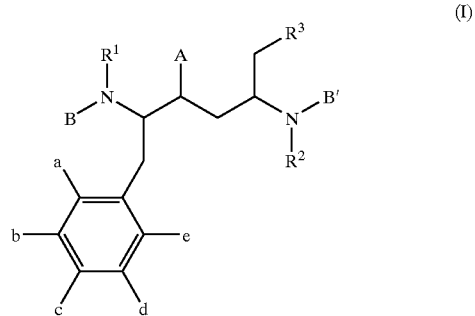

(I)

wherein a, b, c, d, and e, are the same or different and each is $R^7$, $OR^7$, $SR^7$, $NR^7R^8$, $NHCOR^7$, $CO_2R^7$, CN, $NO_2$, $NH_2$, $N_3$, a hydroxyl, a methoxyl, or a halogen. Substituents $R^7$ and $R^8$ are the same or different and each is H, an unsubstituted alkyl or a substituted alkyl. Substituents $R^1$ and $R^2$ are the same or different and each is H or an alkyl, wherein $R^1$ and $R^2$ are unsubstituted or substituted. Substituent $R^3$ is an alkyl, an alkenyl, an alkynyl, or a cycloalkyl. $R^3$ can be unsubstituted or substituted. Substituent A is a heteroatomic substituent, for example, OH, $NH_2$, or SH.

Substituents B and B' are the same or different and each is represented by the formula:

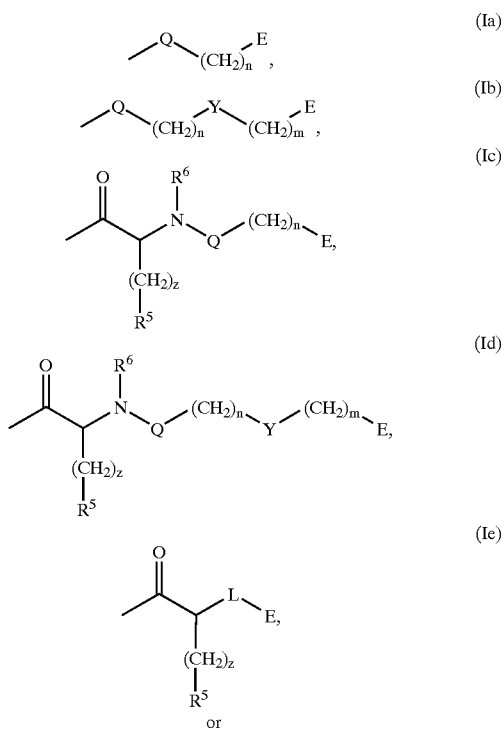

or

-continued

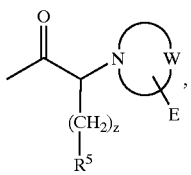

(If)

wherein m, n, and z, are the same or different and each represent an integer from 0 to 4. Q is $SO_2$ (forming a sulfonamide bond) or C=X, wherein X is O (forming an amide bond), an optionally substituted amino (forming an imide bond), $NCO_2R^7$ (forming an imidate), $NSO_2R^7$ (forming a sulfonimidate), or S (forming a thioamide bond). The substituent Y is a heteroatomic spacer, such as O, S, or amino (unsubstituted or substituted), or an organic spacer, for example, an aryl spacer or a heteroaryl spacer.

Substituents B and B' include D and L amino acids and derivatives thereof, for example, those represented by formulae (Ic)–(If). The amino acid substituents can be natural or unnatural (e.g., synthetic). When B or B' is an amino acid substituent of the formula (Ic)–(If), $R^5$ includes H, an alkyl, an alkenyl, an alkynyl, a cycloalkyl, a heterocycloalkyl, an aryl, or a heteroaryl. $R^5$ can be unsubstituted or substituted. Substituents B and B' also include glycolic or thioglycolic acids (e.g., formula (Ie), wherein substituent L is O or S). Alternatively, substituent B or B' can be a monosubstituted amino acid (formula (Ie), wherein substituent L is NH), or even an amino acid without substitution on N-terminus, for example, when L is NH and E is H.

When B or B' is an amino acid substituent, the N-terminus can be unsubstituted (as indicated above), partially substituted or fully substituted. Thus, $R^6$ includes, for example, H, an alkyl, an alkenyl, an alkynyl, a cycloalkyl, a heterocycloalkyl, an aryl, or a heteroaryl, and $R^6$ can be unsubstituted or substituted. When B or B' is an amino acid substituent with N-terminal substitution, the N-terminus thereof can be part of a heterocycle (e.g., as in formula (If)). In formula (1f), W represents an organic residue comprising at least one carbon atom and shares at least two bonds with the N-terminal nitrogen, such that the substituent:

of formula (If) defines a nitrogen-containing heterocycle.

Substituent E is the terminal substituent of formulae (Ia)–(If) and includes, for example, H, $(CH_2)_qR^9$, $O(CH_2)_qR^9$, $S(CH_2)_qR^9$, $N[(CH_2)_qR^9]R^{10}$, CO $(CH_2)_qR^9$, CS $(CH_2)_qR^9$, $CO_2(CH_2)_qR^9$, $NHCO_2(CH_2)_qR^9$, C(O)S $(CH_2)_qR^9$, $C(S)O(CH_2)_qR^9$, $CS_2(CH_2)_qR^9$, C(O)N[ $(CH_2)_qR^9]R^{10}$, $NHC(O)N[(CH_2)_qR^9]R^{10}$, $C(S)N[(CH_2)_qR^9]R^{10}$, $NHC(S)N[(CH_2)_qR^9]R^{10}$, $NR^{10}CO(CH_2)_qR^9$, $NR^{10}CS$ $(CH_2)_qR^9$, $NR^{10}CO_2(CH_2)_qR^9$, $NR^{10}C(O)S(CH_2)_qR9$, $NR^{10}CS_2(CH_2)_qR^9$, $O_2C(CH_2)_qR^9$, $S_2C(CH_2)_qR^9$, SCO $(CH_2)_qR^9$, $OCS(CH_2)_qR^9$, $SO_2(CH_2)_qR^9$, $OSO_2(CH_2)_qR^9$, $NR^{10}SO_2(CH_2)_qR^9$, CN, $NO_2$, $N_3$, or a halogen, wherein q is an integer from 0–4. The substituent $R^9$ is an alkyl, an alkenyl, an alkynyl, an cycloalkyl, a heterocycloalkyl, an aryl, or a heteroaryl. $R^9$ can be substituted or unsubstituted. Substituent $R^{10}$ is H, an unsubstituted alkyl or a substituted alkyl. The compound of the present invention as defined herein also includes prodrugs and pharmacologically acceptable salts thereof.

Alternatively B and $R^1$ together with the nitrogen atom to which they are bonded (i.e., together with the nitrogen on the carbon bearing the benzyl substituent as shown in formula (I)) can comprise a heterocyclic substituent, which can be unsubstituted or substituted. Likewise, B' and $R^2$ together with the nitrogen atom to which they are bonded (i.e., the nitrogen atom on the carbon bearing $CH_2-R^3$, as shown in formula (I)) can comprise a heterocyclic ring, which can be unsubstituted.

The present invention further provides a pharmaceutical composition that includes a carrier and a therapeutically effective amount of at least one compound of the present invention. The therapuetically effective amount is generally an aspartic protease inhibiting-effective amount. The aspartic protease inhibiting-effective amount, for example, can be an HIV-1 protease inhibiting-effective amount, a cathepsin D inhibiting-effective amount, and/or a plasmepsin inhibiting-effective amount.

The present invention further provides a method of preventing or treating an HIV infection which includes administering an HIV protease inhibiting-effective amount of at least one compound of the present invention. Also provided is a method of preventing or treating cancer which includes administering a cathepsin D inhibiting-effective amount of at least one compound of the present invention. The present invention further provides a method of preventing or treating a malarial infection which includes administering a plasmepsin inhibiting-effective amount of at least one compound of the present invention.

DESCRIPTION OF THE PREFERRED EMBODIMENTS

Figure 1:
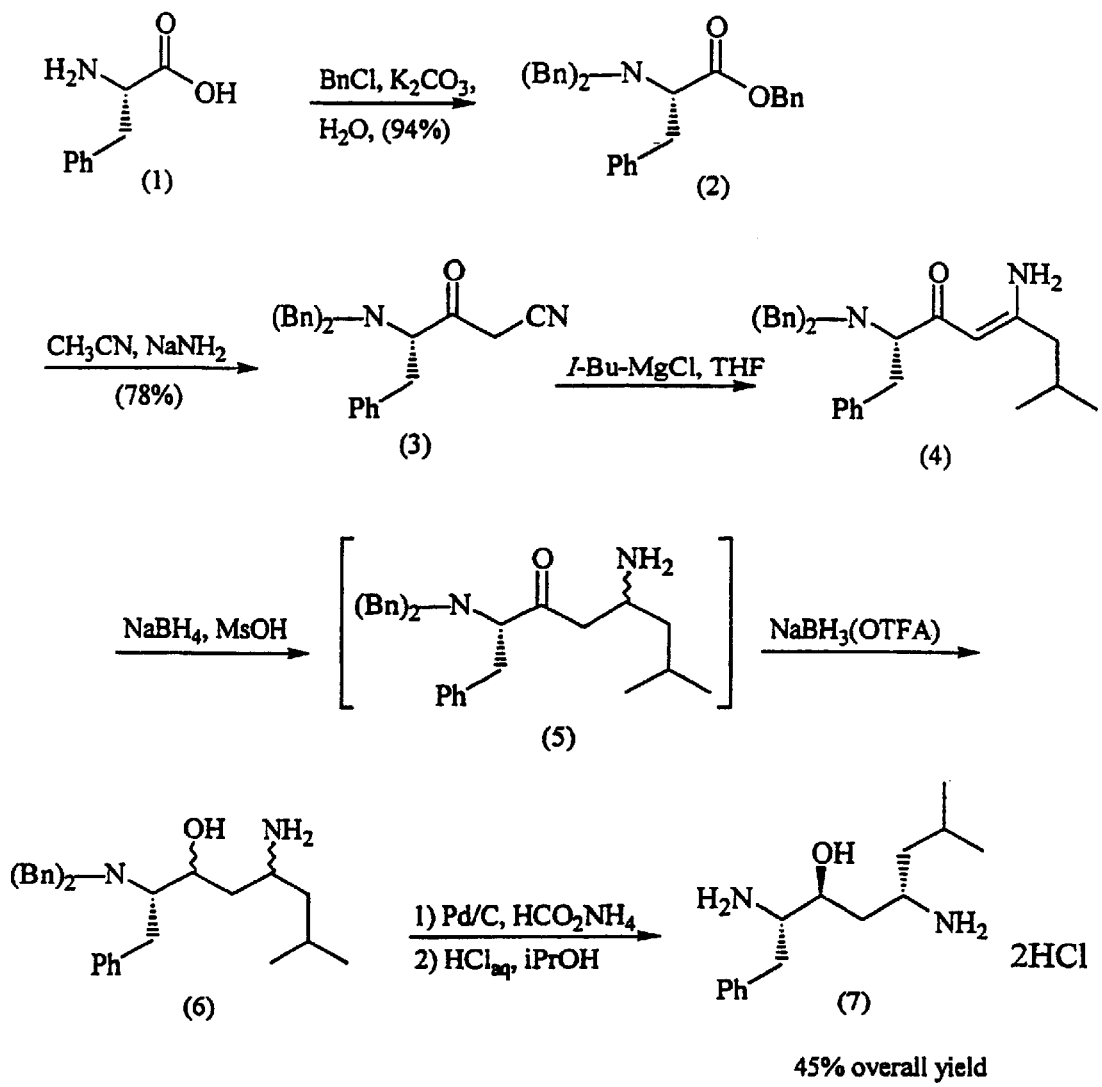
FIG. 1 illustrates the synthesis of a core diamine intermediate that can be used in the preparation of aspartic protease inhibitors.

In a preferred embodiment, the present invention provides a compound of the formula:

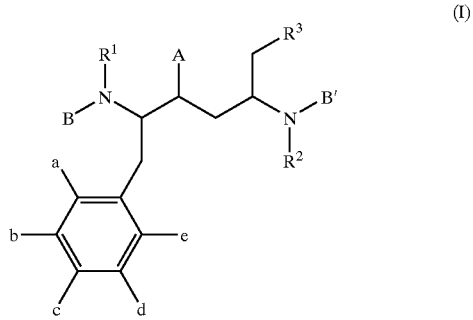

(I)

wherein a, b, c, d, and e, can be the same or different and each is H, $R^7$, $OR^7$, $SR^7$, $NR^7R^8$, $NHCOR^7$, $CO_2R^7$, CN, $NO_2$, $NH_2$, $N_3$, a hydroxyl, a methoxyl, or a halogen. Substituents $R^7$ and $R^8$ can be the same or different and each is H, an unsubstituted alkyl or a substituted alkyl. When either or both of $R^7$ and $R^8$ is an alkyl, each of $R^7$ and $R^8$ is preferably a $C_1$–$C_{12}$ alkyl, more preferably a $C_1$–$C_8$ alkyl, and most preferably $C_1$–$C_6$ alkyl. Accordingly, substituents a–e include, for example, H or an alkyl ($R^7$), a hydroxyl or an ether ($OR^7$), a thiol or a thio ether ($SR^7$), $NH_2$, a mono-alkylamino ($NHR^7$), a di-alkyl amino ($NR^7R^8$), an amido ($NHCOR^7$), an ester or acid ($CO_2R^7$) cyano (CN), nitro ($NO_2$), azido ($N_3$), halogens (iodo, bromo, chloro, or fluoro), and the like.

Substituents $R^1$ and $R^2$ can be the same or different and each is preferably H or an alkyl, preferably a $C_1$–$C_{12}$ alkyl, more preferably a $C_1$–$C_8$ alkyl, and is most preferably $C_1$–$C_6$ alkyl. When $R^1$ or $R^2$ is an alkyl, it can be substituted with one or more substituents selected from the group consisting of $R^7$, $OR^7$, $SR^7$, $NR^7R^8$, CN, $NO_2$, $N_3$, a halogen, and the like, wherein $R^7$ and $R^8$ are as defined herein.

Substituent $R^3$ can be a linear, a branched, or a cyclic substituent, provided that $R^3$ is not aromatic. The presence of a non-aromatic substituent at position $R^3$ in the core structure:

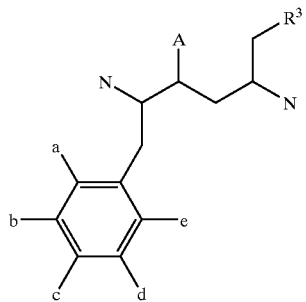

confers advantageous biomedical properties to the compound of the present invention. Although applicants do not wish to be bound by any particular theory, it is believed that a non-aromatic substituent at position $R^3$ enhances the structural flexibility of the core, enabling the inhibitor to "adapt" to structural variations in the active sites of different aspartic proteases.

In particular, it is believed that when $R^3$ is aromatic, $R^3$ and the aromatic ring of the $P_3$, ligand undergo intramolecular "stacking," causing the core to become structurally rigid. By contrast, when a non-aromatic group is substituted at position $R^3$, there is no tendency for $R^3$ and the aromatic ring of the $P_3$, ligand to stack, thereby making the inhibitor molecule structurally more flexible. As such, the compound of the present invention has a greater ability to adapt or conform to the active sites of structurally different aspartic proteases, thereby promoting inhibitory activity against structurally different aspartic proteases.

A wide range of structural combinations for $R^1$, $R^2$, B, and B' can be utilized in conjunction with the core structure of the present invention. Indeed, many different combinations of B and B' provide compounds with potent inhibitory activity against different aspartic proteases, as illustrated in Examples 35 and 36. Moreover, the enhanced flexibility of the core structure also can improve pharmacological properties, for example, metabolic stability and bioavailability, as illustrated below in Example 37.

Preferably, $R^3$ is a straight chain or a branched alkyl, alkenyl, or alkynyl substituent, or is a cycloalkyl. $R^3$ can be unsubstituted or can be substituted with one or more substituents selected from $OR^7$, $SR^7$, CN, $NR^7R^8$, $NO_2$, $N_3$, and a halogen. When $R^3$ is an alkyl, it is preferably a $C_1$–$C_{12}$ alkyl, more preferably a $C_1$–$C_{10}$ alkyl, and most preferably a $C_1$–$C_8$ alkyl. When $R^3$ is an alkenyl or an alkynyl, it is preferably $C_2$–$C_{12}$, more preferably $C_2$–$C_{10}$, and is most preferably a $C_2$–$C_8$ alkenyl or a $C_2$–$C_8$ alkynyl. When $R^3$ is a cycloalkyl, it is preferably a $C_3$–$C_{12}$ cycloalkyl, more preferably a $C_3$–$C_{10}$ cycloalkyl, and is most preferably a $C_3$–$C_8$ cycloalkyl.

Substituent A is heteroatom-containing substituent, preferably OH, $NH_2$, SH, or a derivative thereof.

Substituents B and B' are the same or different, and each can be any suitable substituent that imparts or enhances aspartic protease inhibitory activity of the compounds of the present invention, and/or the pharmacological properties thereof such as, for example, metabolic stability, oral bioavailability, or the like. Preferably, substituents B and B' are the same or different and each is of the formula:

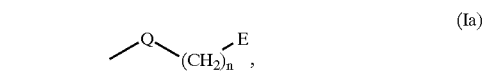 (Ia)

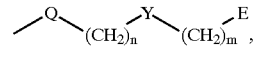 (Ib)

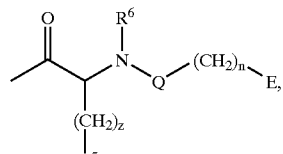 (Ic)

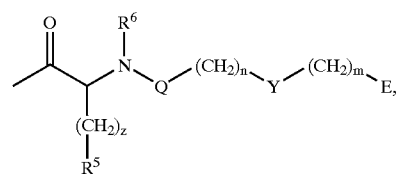 (Id)

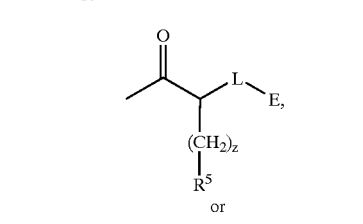 (Ie)

or

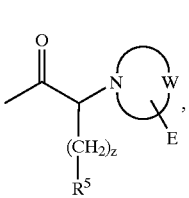 (If)

wherein m, n, and z, are the same or different and each is an integer from 0 to 10. Preferably m and n are each an integer from 0 to 8, more preferably from 0 to 6, and most preferably from 0 to 4.

Substituent Q can be any suitable linking functional group, and preferably is $S_2$ (forming a sulfonamide) or C=(X), wherein X is O (forming an amide bond), $NR^7$ (forming an imide bond)y, $NCO_2R^7$ (forming an imidate) $NSO_2R^7$ (forming a sulfonimidate), or S (forming a thioamide), or the like.

Substituent Y is a heteroatomic spacer such as, for example, O, S, $NR^4$, wherein $R^4$ is H, an alkyl, an alkenyl, an alkynyl, a cycloalkyl, a heterocycloalkyl, an aryl, or a heteroaryl. $R^4$ can be unsubstituted or it can be substituted with one or more substituents selected from the group consisting of $R^7$, $OR^7$, $SR^7$, $NR^7R^8$, CN, $NO_2$, $N_3$, and halogens. Alternatively, Y is an aryl or a heteroaryl. When Y is an aryl or a heteroaryl, it is preferably a $C_6$–$C_{15}$ aryl or a $C_5$–$C_{15}$ heteroaryl (i.e., contains 3–15 carbon atoms in the ring skeleton, not including heteroatoms in the case of heterocyclic substituents). More preferably, when Y is an aryl or a heteroaryl, it is a $C_6$–$C_{10}$ aryl or a $C_5$–$C_{10}$ heteroaryl, and most preferably is a $C_6$ aryl or a $C_5$–$C_8$ heteroaryl. The aryl or the heteroaryl represented by Y can be unsubstituted or can be substituted with one or more substituents selected from the group consisting of, $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, CN, $NO_2$, $N_3$, and halogens, wherein $R^7$ and $R^8$ are the same or different and are as defined herein.

Substituents B and B' include D and L amino acids and derivatives thereof, for example, those represented by formulae (Ic)–(If). The amino acid substituents can be natural or unnatural (e.g., synthetic). For example, $R^5$ can be H, an alkyl, an alkenyl, an alkynyl, a cycloalkyl, a heterocycloalkyl, an aryl, or a heteroaryl. $R^5$ can be unsubstituted or it can be substituted with one or more substituents selected from the group consisting of $R^7$ (hydrogen or an alkyl), $OR^7$ (a hydroxyl or an ether), $SR^7$ (a thiol or a thioether), $NR^7R^8$ (amino), $COR^7$ (an aldehyde or a ketone), $CSR^7$ (e.g., a thioketone), $CO_2R^7$ (an acid or an ester), $C(O)SR^7$ (e.g., a thioester), $C(S)OR^7$ (e.g., a thionoester), $CS_2R^7$ (e.g., a dithioester), $C(O)NR^7R^8$ (a carbon-bonded amide), $NHC(O)NR^7R^8$ (a urea), $C(S)NR^7R^8$ (a thioamide), $NHC(S)NR^7R^8$ (a thiourea), $NR^8COR^7$ (a nitrogen-bonded amide group or an "amido" group), $NR^8CSR^7$ (a nitrogen-bonded thioamide group or a "thioamido" group), $NR^8CO_2R^7$ (a nitrogen-bonded carbamate group), $NR^8C(O)SR^7$ (a nitrogen-bonded thiocarbamate group), $NR^8C(S)OR^7$ (a nitrogen-bonded thionocarbamate group), $NR^8CS_2R^7$ (a nitrogen-bonded dithiocarbamate group), $O_2CR^7$ (an oxygen-bonded carboxylate), $S_2CR^7$ (a sulfur-bonded dithiocarboxylate), $SCOR^7$ (a sulfur-bonded thiocarboxylate), $OCSR^7$ (an oxygen-bonded thionocarboxylate), $SO_2R^7$ (a sulfone), $OSO_2R^7$ (a sulfonate) , $NR^8SO_2R^7$ (a N-bonded sulfonamide), $SO_2NR^7R^8$ (a S-bonded sulfonamide), a guanidyl, CN, $NO_2$, $N_3$, and halogens, and $R^7$ and $R^8$ are as defined herein. Substituents B and B' also include glycolic or thioglycolic acid substituents, for example, as in formula (1e), wherein L is O or S. Alternatively, substituents B and B' can be a monosubstituted amino acid, for example, when B or B' is of formula (Ie) and substituent L is NH. Alternatively, B and B' can be an amino acid without any N-terminal substitution, for example, when B or B' is of formula (Ie), wherein L is NH and E is H.

When B or B' is an amino acid substituent, the N-terminus can be unsubstituted (as indicated above), partially substituted, or fully substituted. Thus, $R^6$ includes, for example, H, an alkyl, an alkenyl, an alkynyl, a cycloalkyl, a heterocycloalkyl, an aryl, or a heteroaryl, wherein $R^6$ is unsubstituted or substituted with one or more substituents selected from the group consisting of $R^7$, $OR^7$, $SR^7$, $CO_2R^7$, $SO_2R^7$, $NR^7R^8$, CN, $NO_2$, $N_3$, a cycloalkyl, a heterocycloalkyl, an aryl, a heteroaryl, and halogens. When $R^6$ is alkyl, it is preferably a $C_1$–$C_{10}$ alkyl, more preferably a $C_1$–$C_8$ alkyl, and is most preferably a $C_1$–$C_6$ alkyl. When $R^6$ is alkenyl or alkynyl, it is preferably a $C_2$–$C_{10}$ alkenyl or alkynyl, more preferably a $C_2$–$C_8$ alkenyl or alkynyl, and is most preferably a $C_2$–$C_6$ alkenyl or a alkynyl. When $R^6$ is a cyclic substituent (e.g., a cycloalkyl, a heterocycloalkyl, an aryl, or a heteroaryl, which are monocylic or bicyclic), it is preferably a $C_3$–$C_{12}$ cyclic substituent (i.e., contains 3–12 carbon atoms in the ring skeleton, not including heteroatoms in the case of heterocyclics). More preferably, when $R^6$ is a cyclic substituent, it is a $C_3$–$C_8$ cycloalkyl, a $C_3$–$C_8$ heterocycloalkyl, an aryl which is a phenyl or a nahpthyl, or a $C_5$–$C_8$ heteroaryl.

When B or B' is an amino acid substituent with N-terminal substitution, the N-terminus can be part of a heterocycle, for example, as shown in formula (If). In formula (1f), W represents an organic residue comprising at least one carbon atom and shares at least two bonds with the N-terminal nitrogen atom such that the substituent:

of formula (If) defines an N-terminal heterocycle. For example W can be an alkyl linker (e.g., —$(CH_2)_{2-9}$—), a linker with one or more heteroatoms (e.g., —$(CH_2)_{2-5}$O$(CH_2)_{2-5}$—, —$(CH_2)_{2-5}$S$(CH_2)_{2-5}$—, —$(CH_2)_{2-5}$SO$(CH_2)_{2-5}$—, —$(CH_2)_{2-5}$SO_2(CH_2)_{2-5}$—, or —$(CH_2)_{2-5}$NH$(CH_2)_{2-5}$—, a carbonyl linker, for example, —$C(O)(CH_2)_{2-9}$—, —$C(O)(CH_2)_{0-5}O(CH_2)_{0-5}$—, —$C(O)(CH_2)_{0-5}S(CH_2)_{0-5}$—, —$C(O)(CH_2)_{0-5}SO(CH_2)_{0-5}$—, —$C(O)(CH_2)_{0-5}SO_2(CH_2)_{0-5}$—, or —$C(O)(CH_2)_{0-5}NH(CH_2)_{0-5}$—, a sulfonyl linker (e.g., by replacing the carbonyl of any of the foregoing linkers with $SO_2$), or the like. The N-terminal heterocycle (and, hence, the organic residue represented by W) can be fully saturated, can contain one or more multiple bonds, and can be unsubstituted or substituted. For example, the NH of —$(CH_2)_2NH(CH_2)_2$— or —$C(O)(CH_2)_{0-4}NH(CH_2)_{0-4}$— is substituted with E to give —$(CH_2)_{2-5}NE(CH_2)_{2-5}$— or —$C(O)(CH_2)_{0-5}NE(CH_2)_{0-5}$—, wherein E is as defined herein. It will also be appreciated that the N-terminal heterocycle may be substituted, regardless of substituent E, with, for example, one or more substituents with one or more substituents selected from the group consisting of oxo, thio, $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR\,SO_2R^7$, CN, $NO_2$, $N_3$, and halogens, wherein $R^7$ and $R^8$ are the same or different and are as defined herein.

Substituent E is the terminal substituent of formulae (Ia)–(If) and preferably includes H, $(CH_2)_qR^9$, $O(CH_2)_qR^9$, $S(CH_2)_qR^9$, $N[(CH_2)_qR^9]R^{10}$, $CO(CH_2)_qR^9$, $CS(CH_2)_qR^9$, $CO_2(CH_2)_qR^9$, $NHCO_2(CH_2)_qR^9$, $C(O)S(CH_2)_qR^9$, $C(S)O(CH_2)_qR^9$, $CS_2(CH_2)_qR^9$, $C(O)N[(CH_2)_qR^9]R^{10}$, $NHC(O)N[(CH_2)_qR^9]R^{10}$, $C(S)N[(CH_2)_qR^9]R^{10}$, $NHC(S)N[(CH_2)_qR^9]R^{10}$, $NR^{10}CO(CH_2)_qR^9$, $NR^{10}CS(CH_2)_qR^9$, $NR^{10}CO_2(CH_2)_qR^9$, $NR^{10}C(O)S(CH_2)_qR^9$, $NR^{10}CS_2(CH_2)_qR^9$, $O_2C(CH_2)_qR^9$, $S_2C(CH_2)_qR^9$, $SCO(CH_2)_qR^9$, $OCS(CH_2)_qR^9$, $SO_2$ $(CH_2)_qR^9$, $OSO_2(CH_2)_qR^9$, $NR^{10}SO_2(CH_2)_qR^9$, CN, $NO_2$, $N_3$, and halogens, wherein q is an integer from 0–4. $R^9$ can be substituted or unsubstituted and includes any suitable organic substituent which is bonded to the compound of the present invention via carbon, a heteroatom, a functional group, or the like. Preferably, $R^9$ is H, an alkyl, an alkenyl, an alkynyl, a cycloalkyl, a heterocycloalkyl, an aryl, or a heteroaryl. When $R^9$ is substituted, it can be substituted with one or more substituents selected from the group consisting of, $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR$, $NR^8CS_2R^7$, $O_2CR^7$, $S_2CR^7$, $OCSR^7$, $SO_2R^7$, $OSO_2R^7$, $NR^8SO_2R^7$, a guanidyl, oxo, thio, CN, $NO_2$, $N_3$, and halogens, wherein $R^7$ and $R^8$ are the same or different and are as defined herein. When $R^9$ is alkyl, it is preferably a $C_1$–$C_{10}$ alkyl, more preferably a $C_1$–$C_8$ alkyl, and is most preferably a $C_1$–$C_6$ alkyl substituent. When $R^9$ is an alkenyl or an alkynyl, it is preferably a $C_2$–$C_{10}$ alkenyl or alkynyl, more preferably a $C_2$–$C_8$ alkenyl or alkynyl, and is most preferably a $C_2$–$C_6$ alkenyl or alkynyl substituent. When $R^9$ is a cyclic substituent (i.e., a cycloalkyl, a heterocycloalkyl, an aryl, or a heteroaryl), it is preferably a $C_3$–$C_{12}$ cyclic substituent (i.e., contains 3–12 carbon atoms in the ring skeleton, not including heteroatoms in the case of heterocyclics). More preferably, $R^9$ is a $C_3$–$C_{10}$ cycloalkyl, a $C_3$–$C_{10}$ heterocycloalkyl, an aryl which is preferably phenyl or naphthyl, or a $C_5$–$C_{10}$ heteroaryl substituent.

While $R^{10}$ can include any suitable substituent defined herein for $R^9$, $R^{10}$ preferably is H or an alkyl which can be unsubstituted or substituted with one or more substituents selected from the group consisting of CN, $NH_2$, $NO_2$, $N_3$, and halogens. The compound of the present invention, as defined herein, also includes prodrugs and pharmaceutically acceptable salts thereof.

With regard to substituent B and B', one embodiment includes compounds in which B or B' is a substituent of the formula:

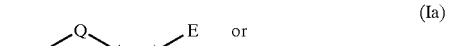
(Ia)

(Ib)

wherein Q, n, m, and E is as defined herein, and Y is a heteroatom spacer. When Y is a heteroatom spacer, it is preferred that Q is a carbonyl (C=O), Y is O or S, m and n are the same or different and each is 0 or 1, and E is $R^9$, wherein $R^9$ is an alkyl, an alkenyl, an alkynyl, a cycloalkyl, a heterocycloalkyl, an aryl, or a heteroaryl. As indicated above, $R^9$ can be unsubstituted or it can be substituted with one or more substituents selected from the group consisting of, $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, a guanidyl, oxo, thio, CN, $NO_2$, $N_3$, a halogens, wherein $R^7$ and $R^8$ are as defined herein.

Examples of particular B or B' is substituents of formula (Ib), wherein Y is a heteroatom spacer, include substituents of the formula:

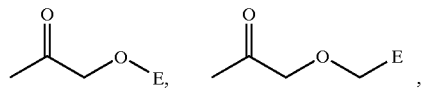

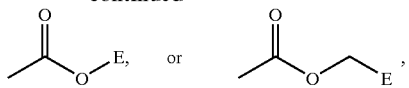

wherein E is $R^9$ (as defined herein). When B or B' is of formula (Ia) or (Ib) and Y is a heteroatom spacer, $R^9$ preferably is an aryl or a heteroaryl, wherein $R^9$ is unsubstituted or substituted. Examples of suitable aryl and heteroaryl substituents for $R^9$ include those selected from the group consisting of 2-methylphenyl, 2,6-dimethylphenyl, 3-amino-2-methylphenyl, 3-acetamido-2-methylphenyl, 3-hydroxy-2-methylphenyl, 4-hydroxy-2-methylphenyl, 4-amino-2-methylphenyl, 3-acetamido-2-methylphenyl, 4-methoxy-2-methylphenyl, 4-fluoro-2-methylphenyl, 4-trifluoromethyl-2-methylphenyl, 2,4-dimethylphenyl, 2-methyl-4-nitrophenyl, 3-amino-2,6-dimethylphenyl, 3-hydroxy-2,6-dimethylphenyl, 2-methyl-3-nitrophenyl, 4-acetyl-2-methylphenyl, 4-aminocarbonyl-2-methylphenyl, benzofuranyl, benzotetrohydrofuranyl, benzothiazolyl, benzimidazolyl, indolyl, quinolinyl, isoquinolinyl, oxazolyl, benzopiperazinyl, benzopyrrolidinyl, pyridinyl, 4-(2-methyl) tetrahydrofuranyl, 4-(2-methyl) tetrahydrothiophenyl, thiazolyl, imidazolyl, tert-butyl, hydroxy tert-butyl, isoxazolyl, pyrazolyl, benzoxadiazolyl, and morpholinyl.

Another embodiment of the present invention includes compounds in which B and/or B' is an amino acid substituent. Examples of suitable amino acid substituents include amino acids and related analogs of the formula:

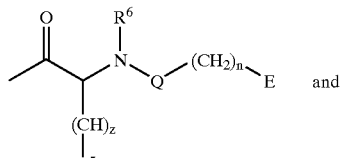
(Ic)

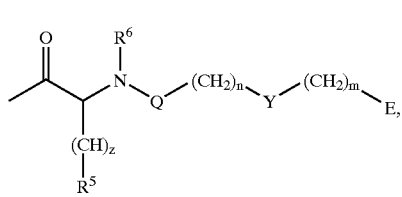
(Id)

wherein z is 0 or 1, $R^5$ is an unsubstituted alkyl or a substituted alkyl, $R^6$ is H, Q is C=O, Y is O or S, m and n are the same or different and each is 0 or 1, and E is $R^9$. Preferably, $R^9$ is an aryl or a heteroaryl, which can be unsubstituted or substituted. When $R^5$ is substituted, it is preferably substituted with one or more substituents selected from the group consisting of, $R^7$, $OR^7$, and $C(O)NR^7R^8$. When $R^9$ is substituted, it is preferably substituted with one or more substituents selected from the group consisting of, $R^7$, $OR^7$, $SR^7$, $NR^7R^8$, $COR^7$, $CSR^7$, $CO_2R^7$, $C(O)SR^7$, $C(S)OR^7$ $CS_2R^7$, $C(O)NR^7R^8$, $NHC(O)NR^7R^8$, $C(S)NR^7R^8$, $NHC(S)NR^7R^8$, $NR^8COR$ , $NR^8CSR$, $NR^8CO_2R^7$, $NR^8C(C)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, a guanidyl, CN, $NO_2$, $N_3$, and halogens, wherein $R^7$ and $R^8$ are the same or different and are as defined herein.

Valine analogs are among the preferred amino acid substituents for B and/or B' and are represented, for example, in formulae (Ic) and (Id), wherein z is 0 and $R^5$ is isopropyl. When B or B' is a valine analog represented by formula (Ic)

or (Id), it is preferred that $R^6$ is H, Q is a carbonyl (C=O), Y is O or S, m and n are the same or different and each is 0 or 1, and E is $R^9$. $R^9$ is preferably an aryl or a heteroaryl, which can be unsubstituted or substituted. When $R^9$ is substituted, it is preferably substituted with one or more substituents selected from the group consisting of, $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, CN, $NO_2$, $N_3$, and halogens. $R^7$ and $R^8$ are the same or different and are as defined herein. More preferably, the valine analog of formula (Ic) or (Id) is of the formula:

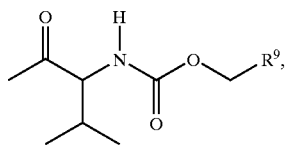

wherein $R^9$ is selected from the group consisting of phenyl, pyridinyl, thiazolyl, isothiazolyl, oxazolyl, isoxazolyl, pyrazolyl, imidazolyl, pyrrolyl, thiophenyl, furanyl, oxadiazolyl, benzothiazolyl, benzoisothiazolyl, benzoxazolyl, benzoisoxazolyl, benzopyrazolyl, benzimidazolyl, indolyl, benzothiophenyl, benzofuranyl, and benzoxadiazolyl, wherein the foregoing can be unsubstituted or substituted as described herein.

When B or B' is an amino acid substituent, even relatively simple substitution of the N-terminal nitrogen can result in potent aspartic protease inhibitory activity. Accordingly, B and B' include substituents of formula (Ie), wherein L is NH, z is 0, and $R^5$ is isopropyl, such that B and/or B' is:

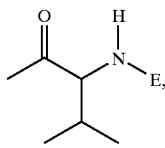

wherein E is H, $COR^9$, or $SO_2R^9$, wherein $R^9$ includes relatively simple substituents such as, for example, methyl, and the like.

The N-terminal nitrogen of the amino acid analog of substituent B or B' also can be included in a cyclic structure such that the N-terminus is part of a nitrogen-containing heterocyclic ring system. A preferred amino acid analog in which the N-terminus is included in a nitrogen-containing heterocycle is represented by the formula:

(If)

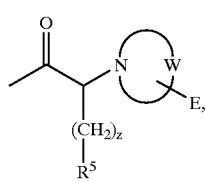

wherein z, $R_5$, W and E are as defined herein. In one embodiment, the substituent:

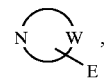

(of formula (1f)) defines an N-terminal heterocycle, such that B or B' is of the formula:

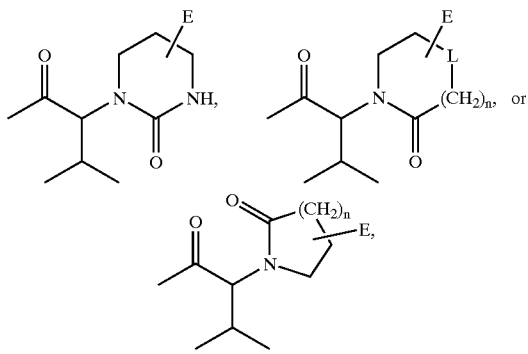

wherein n is an integer from 1–4, L is O, S, or NH, and E is as defined herein. The organic residue represented by W also includes linkers of the formula $-(CH_2)_{2-9}-$, $-(CH_2)_{2-5}O(CH_2)_{2-5}-$, $-(CH_2)_{2-5}S(CH_2)_{2-5}-$, $-(CH_2)_{2-5}SO(CH_2)_{2-5}-$, $-(CH_2)_{2-5}SO_2(CH_2)_{2-5}-$, $-(CH_2)_{2-5}NH(CH_2)_{2-5}-$, $-C(O)(CH_2)_{2-9}-$, $-C(O)(CH_2)_{0-5}O(CH_2)_{0-5}-$, $-C(O)(CH_2)_{0-5}S(CH_2)_{0-5}-$, $-C(O)(CH_2)_{0-5}SO(CH_2)_{0-5}-$, $-C(O)(CH_2)_{0-5}SO_2(CH_2)_{0-5}-$, $-C(O)(CH_2)_{0-5}NH(CH_2)_{0-5}-$, or a corresponding sulfonyl linker (e.g., wherein a C(O) in any of the foregoing linkers is replaced by $SO_2$). The N-terminal heterocycle can be unsubstituted or it can be substituted. For example, the N-terminal heterocycle is substituted with E as defined herein. It will also be appreciated that the N-terminal heterocycle may be substituted, regardless of substituent E, with one or more substituents selected from the group consisting of $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, CN, $NO_2$, $N_3$, and halogens, wherein $R^7$ and $R^8$ are the same or different and each is H, an unsubstituted alkyl or a substituted alkyl (as defined herein).

Another embodiment of the present invention includes a compound in which B and/or B' comprises a substituent of the formula:

(Ib)

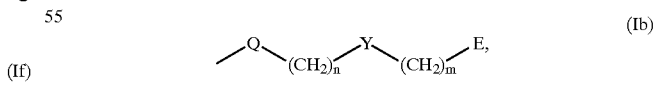

wherein Y is a cyclic spacer and m, n, and E are as defined herein. While any suitable cyclic spacer for Y can be utilized (e.g., a cycloalkyl, a heterocycloalkyl, an aryl, a heteroaryl, or the like), Y is preferably an aryl or a heteroaryl. The cyclic spacer Y can be unsubstituted or substituted as described herein. In a preferred embodiment, Q is C=O, Y is a phenyl spacer and m and n are both zero such that B and/or B' is of the formula:

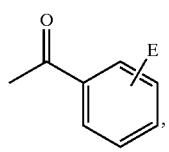

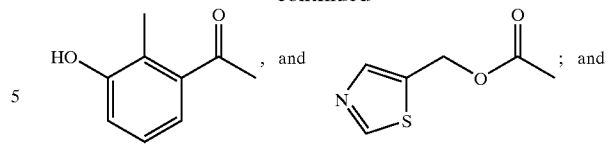

wherein E is as defined herein. In a particularly preferred embodiment, when Y is a phenyl spacer, E is NHCO$_2$(CH$_2$)$_q$R$^9$, wherein q is 0 or 1, and R$^9$ is a phenyl or a pyridinyl, which can be unsubstituted or substituted with one or more substituents selected from the group consisting of, R$^7$, OR$^7$, SR$^7$, NR$^7$R$^8$, COR$^7$, CSR$^7$, CO$_2$R$^7$, C(O)SR$^7$, C(S)OR$^7$, CS$_2$R$^7$, C(O)NR$^7$R$^8$, NHC(O)NR$^7$R$^8$, C(S) NR$^7$R$^8$, NHC(S)NR$^7$R$^8$, NR$^8$COR$^7$, NR$^8$CSR$^7$, NR$^8$CO$_2$R$^7$, NR$^8$C(O)SR$^7$, NR$^8$CS$_2$R$^7$, O$_2$CR$^7$, S$_2$CR$^7$, SCOR$^7$, OCSR$^7$, SO$_2$R$^7$, OSO$_2$R$^7$, NR$^8$SO$_2$R$^7$, CN, NO$_2$, N$_3$, and halogens, wherein R$^7$ and R$^8$ are the same or different and are as defined herein.

Examples of specific compounds of the present invention include compounds represented by formula (I), wherein a, b, c, d, e, R$^1$, and R$^2$ are all H, R$^1$ is isopropyl, A is OH, B defines a substituent which is bonded to formula (I) via an amide bond, and is selected from the group consisting of:

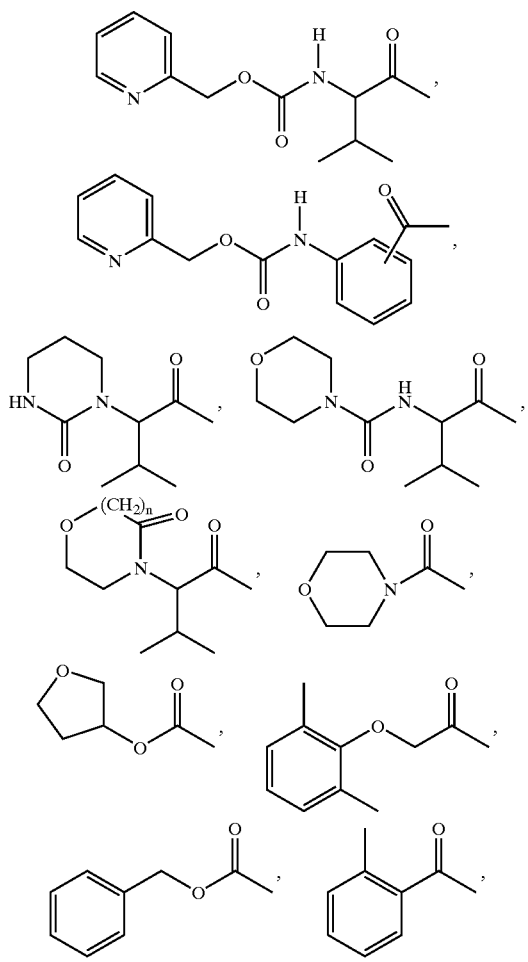

B' is bonded to formula (I) via an amide bond, and is selected from the group consisting of:

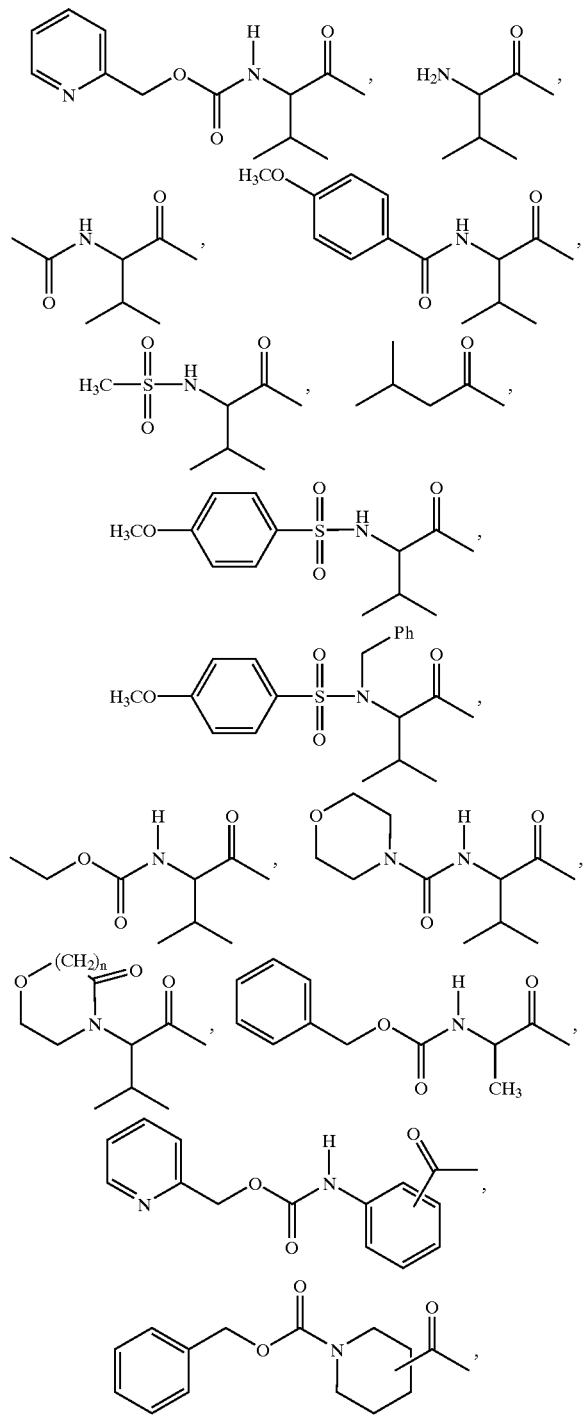

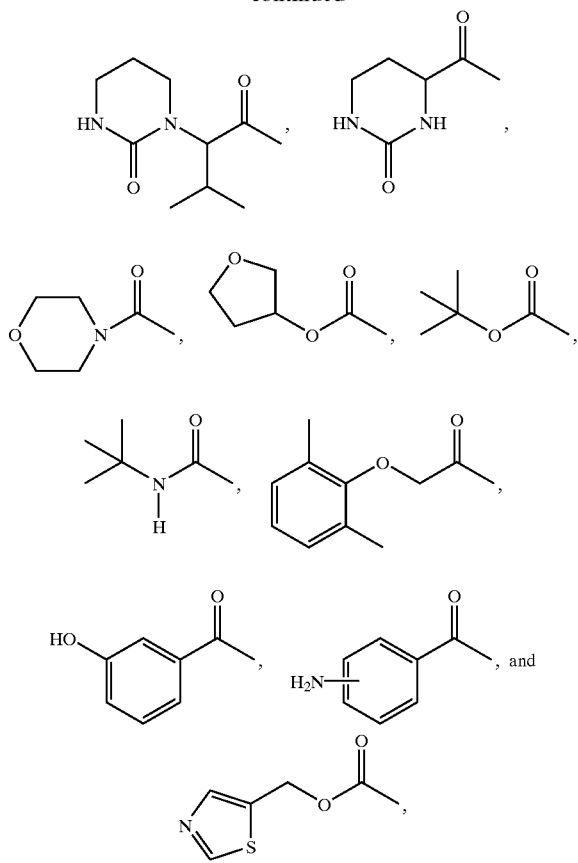
wherein n is an integer from 0–4.
Examples of other particularly preferred embodiments include compounds of formula (I), wherein a, b, c, d, e, $R^1$; and $R^2$ are all H, $R^3$ is isopropyl, A is OH, and B and B' are the same or different and each is selected from the group consisting of:
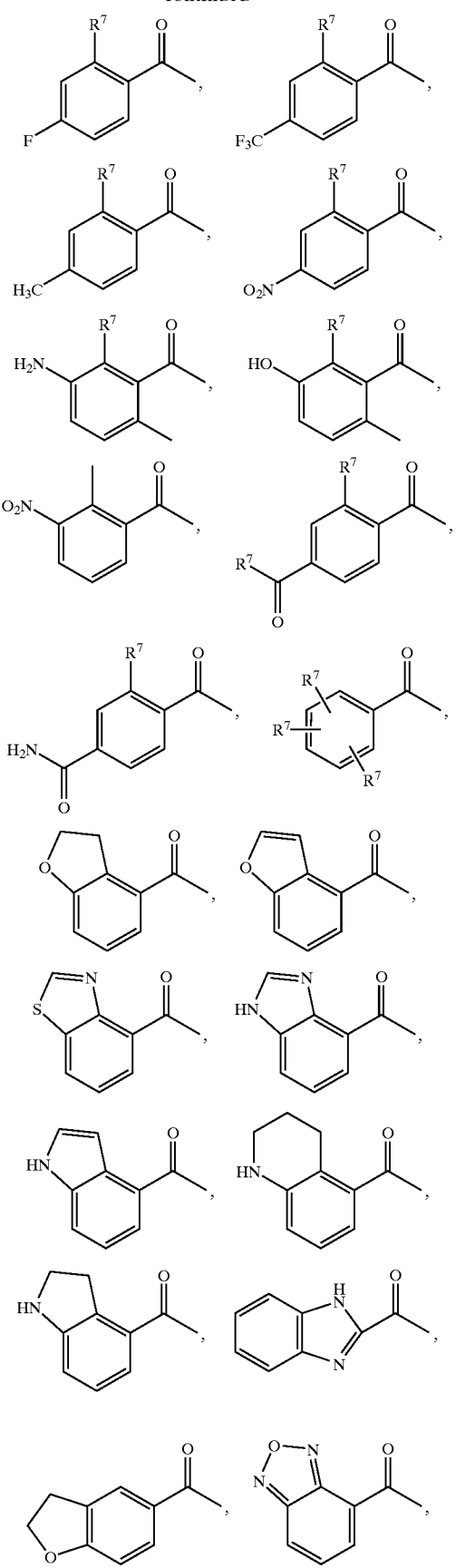

-continued

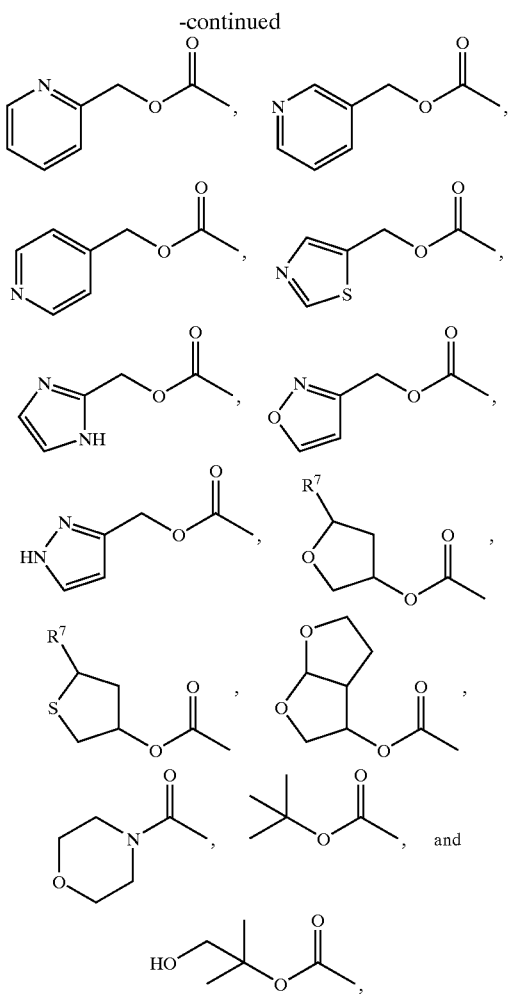

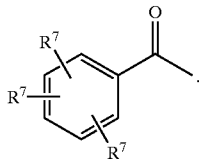

wherein R⁷ is H, an unsubstituted alkyl or a substituted alkyl. In a preferred embodiment, both B and B' are benzamide substituents, which are the same or different, and each is preferably of the formula:

a In all of the embodiments defined herein, each occurrence of any substituent defined by a variable can be the same or different if two or more of such substituents are on the same molecule. Thus, for example, each $R^7$ can be H, an unsubstituted alkyl or a substituted alkyl, as defined herein, and each occurrence of $R^7$ can be the same or different when two or more $R^7$ substituents are on the same molecule.

Alternatively B and $R^1$ together with the nitrogen atom to which they are bonded (i.e., together with the nitrogen on the carbon bearing the benzyl substituent as shown in formula (I)) can comprise a heterocycle, which can be unsubstituted or substituted. The heterocycle defined by B and $R^1$ includes, for example, a cyclic substituent of the formula:

thus defining a compound of the formula:

(Ig)

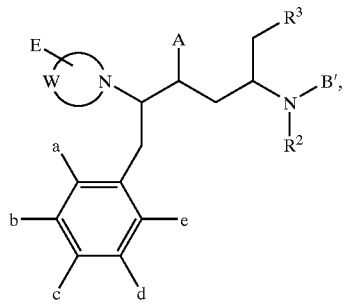

wherein W and E are as defined herein. Likewise, B' and $R^2$ together with the nitrogen atom to which they are bonded (i.e., the nitrogen atom on the carbon bearing $CH_2$—$R^3$, as shown in formula (I)) can comprise a heterocycle, which can be unsubstituted or substituted. The heterocycle defined by B' and $R^2$ includes, for example, a cyclic substituent of the formula:

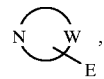

thus defining a compound of the formula:

(Ih)

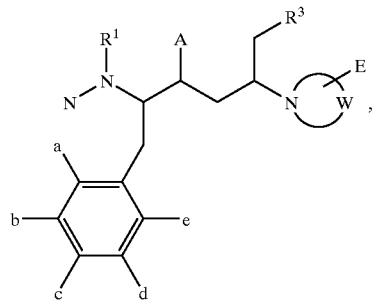

wherein W and E are as defined herein. The organic residue represented by W includes, by way of example, linkers of the formula —$(CH_2)_{2-9}$—, —$(CH_2)_{2-5}O(CH_2)_{2-5}$—, —$(CH_2)_{2-5}S(CH_2)_{2-5}$—, —$(CH_2)_{2-5}SO(CH_2)_{2-5}$—, —$(CH_2)_{2-5}SO_2(CH_2)_{2-5}$—, —$(CH_2)_{2-5}NH(CH_2)_{2-5}$—, —$C(O)(CH_2)_{2-9}$—, —$C(O)(CH_2)_{0-5}O(CH_2)_{0-5}$—, —$C(O)(CH_2)_{0-5}S(CH_2)_{0-5}$—, —$C(O)(CH_2)_{0-5}SO(CH_2)_{0-5}$—, —$C(O)(CH_2)_{0-5}SO_2(CH_2)_{0-5}$—, —$C(O)(CH_2)_{0-5}NH(CH_2)_{0-5}$—, or a corresponding sulfonyl linker (e.g., wherein a C(O) in any of the foregoing linkers is replaced by $SO_2$). The heterocyclic ring defined by B and $R^1$ together with the nitrogen atom to which they are bonded, and/or the heterocyclic ring defined by B' and $R^2$ together with the nitrogen atom to which they are bonded can be unsubstituted or substituted. For example, the NH of —$(CH_2)_{2-5}NH$ $(CH_2)_{2-5}$— or —$C(O)(CH_2)_{0-5}NH(CH_2)_{0-5}$— can be substituted with E as defined herein to give, for example, —$(CH_2)_2NE(CH_2)_2$— or —$C(O)(CH_2)_{0-4}NE(CH_2)_{0-4}$—, wherein E is as defined herein. The heterocycle defined by B and $R^1$ together with the nitrogen atom to which they are bonded, and/or the heterocycle defined by B' and $R^2$ together with the nitrogen atom to which they are bonded is substituted with substituent E as defined herein. It will also be appreciated that these heterocycles may be substituted, regardless of substituent E, with one or more substituents selected from the group consisting of oxo, thio, $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, CN, $NO_2$, $N_3$, and halogens, as defined herein. Examples of such heterocyclic rings include those described in connection with formula (If).

The compound of the present invention also includes pharmacologically acceptable salts and prodrugs of the compound of the present invention.

As utilized herein, the term "alkyl" means a straight-chain or branched-chain alkyl substituent containing from about 1 to about 20 carbon atoms chain, preferably from about 1 to about 10 carbon atoms, more preferably from about 1 to about 8 carbon atoms, still more preferably from about 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like.

The term "alkenyl" means a straight-chain or branched-chain alkenyl substituent having one or more double bonds and containing from about 2 to about 20 carbon atoms chain, preferably from about 2 to about 10 carbon atoms, more preferably from about 2 to about 8 carbon atoms, still more preferably from about 2 to about 6 carbon atoms. Examples of such substituents include vinyl, allyl, 1,4-butadienyl, isopropenyl, and the like.

The term "alkynyl" means a straight-chain or branched-chain alkynyl substituent having one or more triple bonds and containing from about 2 to about 20 carbon atoms chain, preferably from about 2 to about 10 carbon atoms, more preferably from about 2 to about 8 carbon atoms, still more preferably from about 2 to about on 6 carbon atoms. Examples of such substituents include ethynyl, propynyl (propargyl), butynyl, and the like.

The term "alkylamino" and "dialkylamino" means an alkyl or a dialkyl amine substituent, wherein the term "alkyl" is defined as above. Examples of alkylamino substituents include methylamino ($NHCH_3$), ethylamino ($NHCH_2CH_3$), n-propylamino, isopropylamino, n-butylamino, isobutylamino, sec-butylamino, tert-butylamino, n-hexylamino, and the like. Examples of dialkylamino substituents include dimethylamino ($N(CH_3)_2$), diethylamino ($N(CH_2CH_3)_2$), di-n-propylamino, diisopropylamino, di-n-butylamino, diisobutylamino, di-sec-butylamino, di-tert-butylamino, di-n-hexylamino, and the like.

The term "cycloalkyl" means a monocyclic or a polycyclic alkyl substituent defined by one or more alkyl carbocyclic rings, which can be the same or different when the cycloalkyl is a polycyclic substituent having 3 to about 10 carbon atoms in the carbocyclic skeleton in each ring, preferably about 4 to about 7 carbon atoms, more preferably 5 to 6 carbons atoms. Examples of monocyclic cycloalkyl substituents include cyclopropyl, cyclobutyl, cyclopentyl, cyclohexyl, cycloheptyl, cyclodecyl, and the like. Examples of polycyclic cycloalkyl substituents include decahydronaphthyl, bicyclo[5.4.0]undecyl, adamantyl, and the like.

The term "aryl" refers to an aromatic carbocyclic substituent, as commonly understood in the art, and includes monocyclic and polycyclic aromatics such as, for example, phenyl and naphthyl substituents, and the like.

The term "heteocycle" or "heterocyclic" encompasses both hetercycloalkyls and heteroaryls. The term "heterocycloalkyl" means a cycloalkyl substituent as defined herein (including polycyclics), wherein at least one carbon which defines the carbocyclic skeleton is substituted with a heteroatom such as, for example, O, N, or S, optionally comprising one or more double bond within the ring, provided the ring is not heteroaryl as defined herein. The heterocycloalkyl preferably has 3 to about 10 atoms (members) in the carbocyclic skeleton of each ring, preferably about 4 to about 7 atoms, more preferably 5 to 6 atoms. Examples of heterocycloalkyl substituents include epoxy, aziridyl, oxetanyl, tetrahydrofuranyl, dihydrofuranyl, piperadyl, piperidinyl, pyperazyl, piperazinyl, pyranyl, morpholinyl, and the like.

The term "heteroaryl" means a substituent defined by an aromatic heterocyclic ring, as is commonly understood in the art, including monocyclic and polyclic heteroaryls. Monocyclic heteroaryls include, for example, imidazole, thiazole, pyrazole, pyrrole, furane, pyrazoline, thiophene, oxazole, isoxazol, pyridine, pyridone, pyrimidine, pyrazine, and triazine substituents. Polycyclic heteroaryls include, for example, quinoline, isoquinoline, indole, purine, benzimidazole, benzopyrrole, and benzothiazole substituents, which heteroaryl substituents are optionally substituted with one or more substituents selected from the group consisting of a halogen, an alkyl, alkoxy, amino, cyano, nitro, and the like. It will be appreciated that the heterocycloalkyl and heteroaryl substituents can be coupled to the compounds of the present invention via a heteroatom, such as nitrogen (e.g., 1-imidazolyl).

It will also be appreciated that certain polycyclic heterocyclic substituents may contain an aromatic ring and a non-aromatic ring. Examples of such polycyclic substituents include, for example, benzotetrahydrofuranyl, benzopyrrolidinyl, benzotetrahydrothiophenyl, and the like.

The term "amino acid" means any alpha-amino acid, as is commonly understood in the art, in D or L form, or any D,L-mixture thereof, which are naturally-occurring or unnatural (e.g., synthetic), or a derivative thereof. Examples of common amino acids include glycine, alanine, valine, tyrosine, phenylalanine, histidine, tryptophan, aspartic acid, serine, homoserine, glutamic acid, asparagine, glutamine, methionine, lysine, arginine, leucine, isoleucine, threonine, cysteine, and the like. Synthetic amino acids include, for example, O-methyl-tyrosine, 4-thiazolyl alanine, 2-thiazolyl alanine, 3-pyrazolyl alanine, homophenylalanine, p-fluorophenylalanine, O-benzyl serine, and the like.

Figure 2:
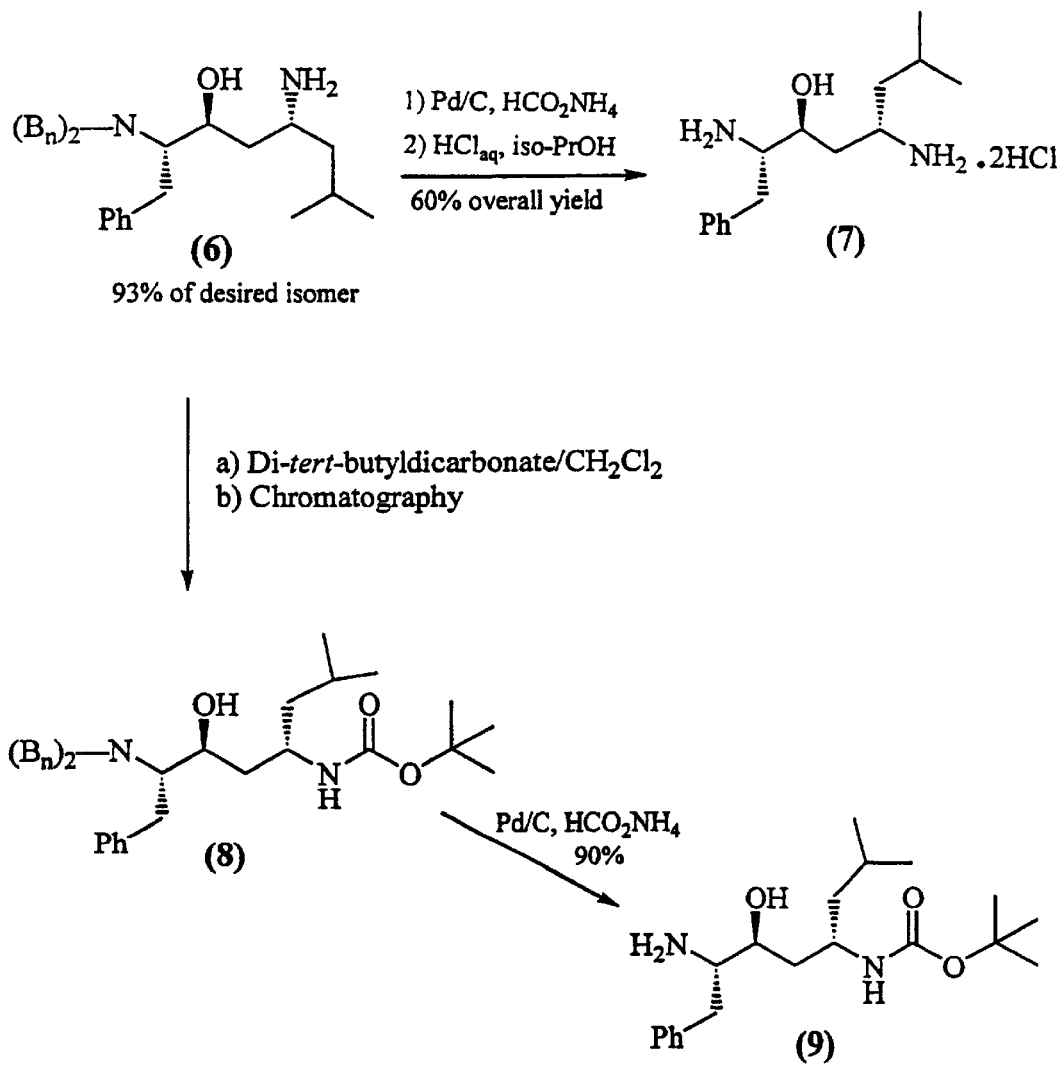
FIG. 2 illustrates the synthesis of various differentially N-protected core diamine intermediates.
Figure 3:
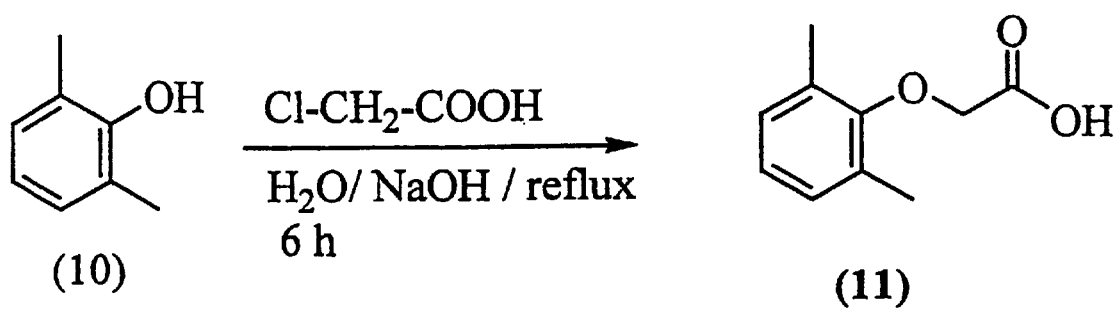
FIG. 3 illustrates the synthesis of 2,6-dimethylphenoxyacetic acid.
Figure 4:
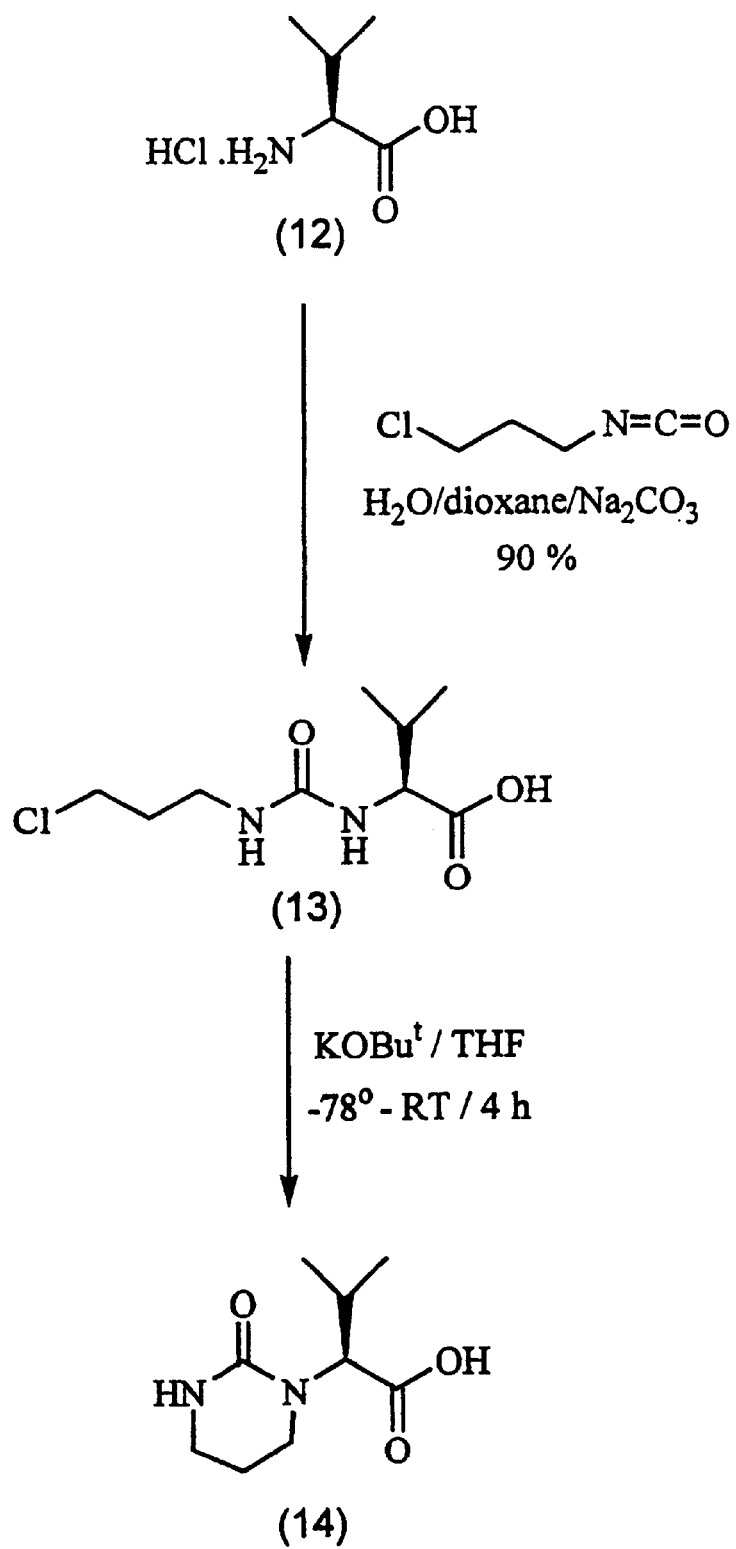
FIG. 4 illustrates the synthesis of N-(2-oxopyrimidinyl) valine.
Figure 5:
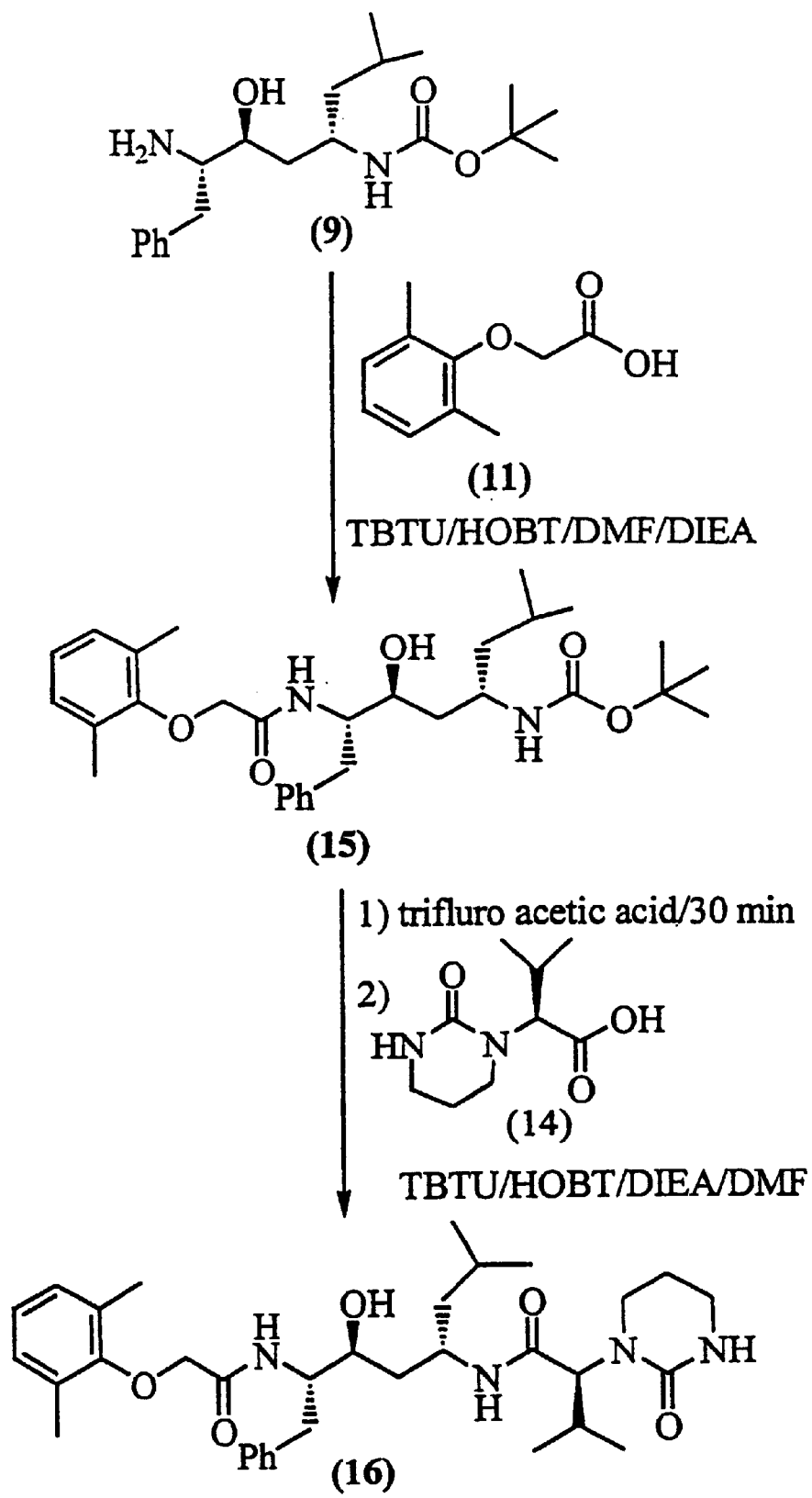
FIG. 5 illustrates the synthesis of various aspartic protease inhibitors.
Figure 6:
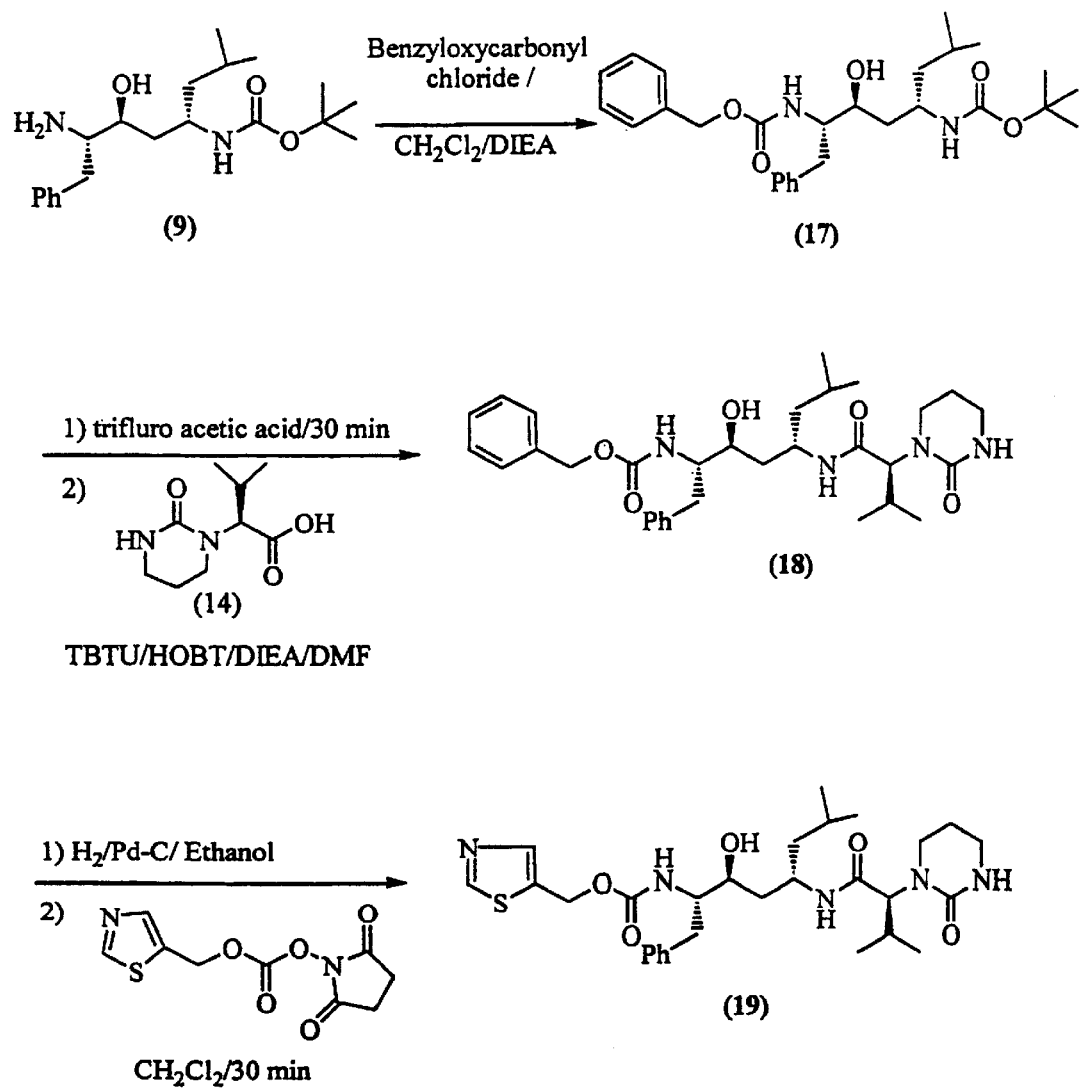
FIG. 6 illustrates the synthesis of various aspartic protease inhibitors.
Figure 7:
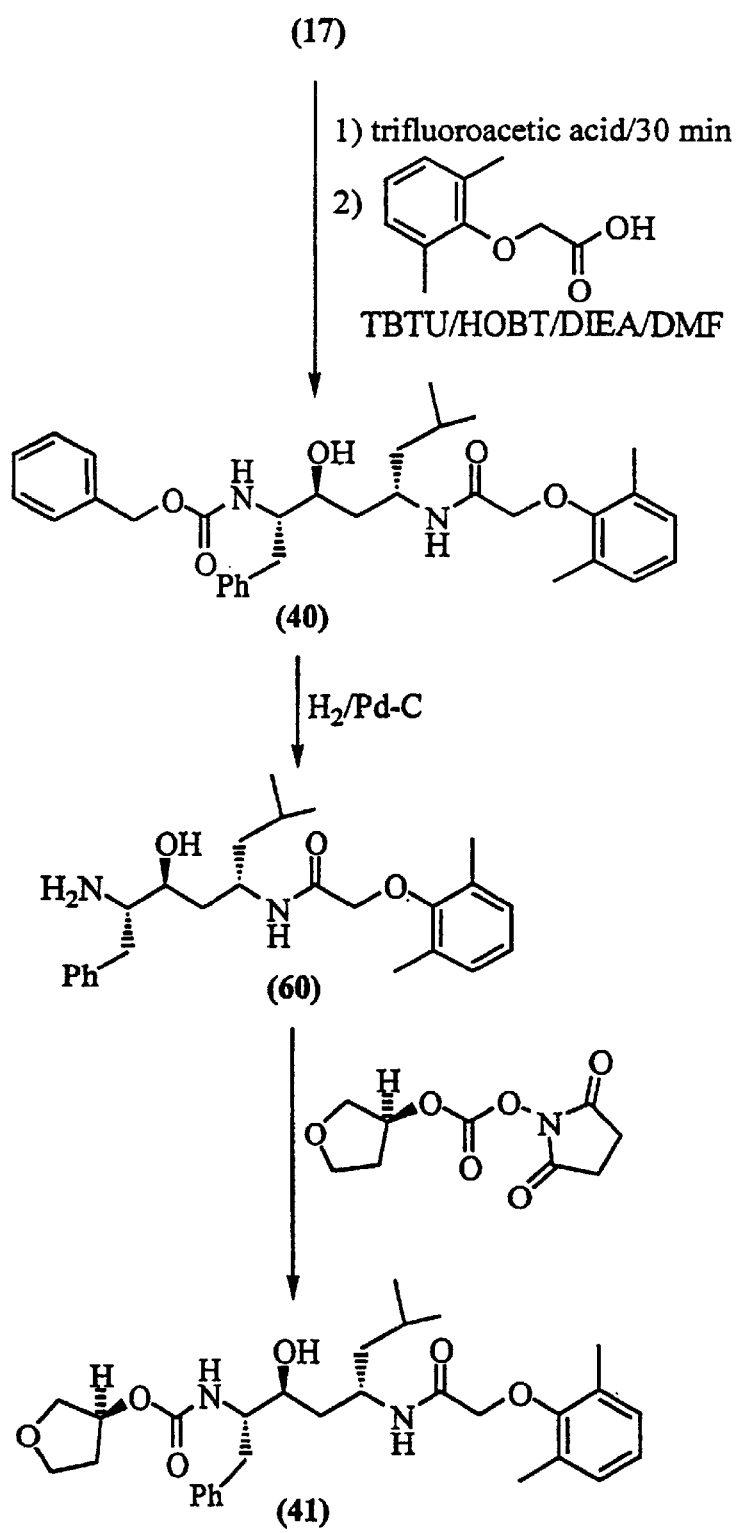
FIG. 7 illustrates the synthesis of various aspartic protease inhibitors.

It will be appreciated that the compounds encompassed within the scope of the present invention, including modifications, derivatives, and substituents thereof, can be prepared by synthetic methods available in those of ordinary skill in the art. Examples of methods suitable for preparing representative compounds within the scope of the present invention, and intermediates therefore, are illustrated in FIGS. 1–7. An example of the synthesis of an unsubstituted "core" diamine structure of formula (I) is illustrated, for example, in FIG. 1. In FIG. 1, diamine (7) is obtained in six synthetic steps from phenylalanine. Other diamine cores can be made in accordance with the chemistry shown in FIG. 1. Moreover, intermediate (6) in FIG. 1 can be utilized to provide a differentially protected amine (9) with respect to the diamine core, wherein each amine can be selectively protected or reacted, as illustrated in FIG. 2, compounds (6) and (9). FIGS. 3 and 4 illustrate methods of preparing compounds that can be utilized as B and B' substituents for formula (I). FIGS. 5–7 illustrate methods of preparing various aspartic protease inhibitors of the present invention, in which the substituents B and B' are different. The synthetic procedures illustrated in FIGS. 1–7 are described in greater detail in the examples below.

The present invention further provides a pharmaceutical composition which includes a carrier and a therapeutically effective amount of at least one compound of the present invention. The pharmaceutical composition of the present invention may be in a form suitable for oral use such as, for example, tablets, troches, lozenges, aqueous or oily suspensions, dispersible powders or granules, emulsions, hard or soft capsules, syrups or elixirs. Compositions intended for oral use may be prepared according to any method known in the art form the manufacture of pharmaceutical compositions, and such compositions can contain one or more agents including, for example, sweetening agents, flavoring agents, coloring agents, and preserving agents in order to provide a pharmaceutically elegant and/or palatable preparation. Tablets can contain the active ingredient in admixture with non-toxic pharmaceutically acceptable excipients which are suitable for manufacture of tablets. Such excipients can include, for example, inert diluents such as, for example, calcium carbonate, lactose, calcium phosphate or sodium phosphate; granulating and disintegrating agents such as, for example, maize starch or alginic acid; binding agents such as, for example, starch, gelatine or acacia, and lubricating agents such as, for example, stearic acid or talc. The tablets may be uncoated, or they may be coated by known techniques to delay disintegration and absorption in the gastrointestinal tract and thereby provide a sustained action over a longer period. A time delay material, for example, glyceryl monostearate or glyceryl distearate, alone or with a wax, may be employed. Formulations for oral use also can be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example arachis oil, peanut oil, liquid paraffin or olive oil.

Aqueous suspensions typically contain the active materials in admixture with excipients suitable for the manufacture of aqueous suspensions. Such excipients include suspending agents, for example, sodium carboxymethyl cellulose, methylcellulose, hydroxypropylmethylcellulose, sodium alginate, polyvinylpyrrolidone, gum tragacanth and gam acacia. Dispersing or wetting agents may include natural-occurring phosphatides, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example, polyoxyethylene sorbitol monooleate, or condensation products of ethylene oxide with partial esters derived from fatty acids and hexitol anhydrides, for example, polyoxyethylene sorbitan mono-oleate. The aqueous suspensions also can contain one or more preservatives, for example, ethyl or n-propyl p-hydroxy benzoate, one or more coloring agents, one or more flavoring agents and one or more sweetening agents such as, for example, sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions can be preserved by the addition of an antioxidant such as, for example, ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, also may be present.

The pharmaceutical composition of the present invention also can be in the form of oil-in-water-emulsions. The oily phase can be a vegetable oil, for example, olive oil or arachis oils, or a mineral oil, for example liquid paraffin or mixtures of these. Suitable emulsifying agents may be naturally-occurring gums, for example gum acacia or gum tragacantn, naturally-occurring phosphatides, for example soya bean lecithin, and esters or partial esters derived from fatty acids and hexitol anhydrides, for example sorbitan mono-oleate, and condensation products of the said partial esters and ethylene oxide, for example polyoxyethylene sorbitan mono-oleate. The emulsions also can contain sweetening and flavoring agents.

The pharmaceutical composition of the present invention can be in the form of syrups and elixirs, which are typically formulated with sweetening agents such as, for example, glycerol, sorbitol or sucrose. Such formulations also can contain a demulcent, a preservative and flavoring and coloring agents.

The pharmaceutical composition can be in the form of a sterile injectable preparation, for example, as a sterile injectable aqueous or oleagenous suspension. Suitable suspensions for parenteral administration can be formulated according to the known art using those suitable dispersing or wetting agents and suspending agents which have been mentioned above. Formulations suitable for parenteral administration also can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The sterile injectable preparation can be in the form of a solution or a suspension in a non-toxic parenterally-acceptable diluent or solvent, for example, as a solution in water or 1,3-butanediol. Among the acceptable vehicles and solvents that can be employed, for example, are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as, for example, oleic acid find use in the preparation of injectables.

The compound(s) of the present invention also can be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols. Formulations suitable for vaginal administration can be presented as pessaries, tampons, creams, gels, pastes, and foams.

Formulations suitable for topical administration may be presented as creams, gels, pastes, or foams, containing, in addition to the active ingredient, such carriers as are known in the art to be appropriate.

The aspartic protease inhibitors of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations such as in a nebulizer or an atomizer.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Any suitable dosage level can be employed in the pharmaceutical compositions of the present invention. The dose administered to an animal, particularly a human, in accordance with the present invention should be sufficient to effect a prophylactic or therapeutic response in the animal over a reasonable time frame. The amount of active ingredient that can be combined with the carrier materials to produce a single dosage form will vary depending upon the host treated and the particular mode of administration. One skilled in the art will recognize that the specific dosage level for any particular patient will depend upon a variety of factors including, for example, the activity of the specific compound employed, the age, body weight, general health, sex, diet, time of administration, route of administration, rate of excretion, drug combination and the severity of the particular disease undergoing therapy. The size of the dose will also be determined by the existence, nature, and extent of any adverse side-effects that might accompany the administration of a particular compound. Other factors which effect the specific dosage include, for example, bioavailability, metabolic profile, and the pharmacodynamics associated with the particular compound to be administered in a particular patient.

Suitable doses and dosage regimens can be determined by comparisons, for example, with peptidomimmetic protease inhibitor agents that are known to effect a desirable anti-infective response, or by comparisons with any other anti-retroviral chemotherapeutic agents that are known to inhibit the proliferation of a retrovirus in an infected individual. The preferred dosage is the amount which results in the prevention or inhibition of an infection (e.g., HIV or malarial), or in the inhibition of cancer metastasis, without significant side effects. In proper doses and with suitable administration of certain compounds, the present invention provides for a wide range of effects, e.g., from partial inhibition to essentially complete inhibition of the aspartic protease associated with the disease-causing organism or, in the case of cancer, from partial inhibition to essentially complete inhibition of the aspartic protease associated with cancer metastasis.

For antiviral compositions, the aspartic protease inhibitors of the present invention also can be administered in combination with other antiretroviral compounds such as, for example, ritonavir, amprenavir, saquinavir, indinavir, AZT, ddI, ddC, D4T, lamivudine, 3TC, and the like, as well as admixtures and combinations thereof, in a pharmaceutically acceptable carrier. The individual daily dosages for these combinations can range from about one-fifth of the minimally recommended clinical dosages to the maximum recommended levels for the entities when they are given singly.

Generally, the therapeutically effective amount in the pharmaceutical compositions of the present invention is an aspartic protease inhibiting-effective amount. In one preferred embodiment, the therapeutically effective amount is an aspartic protease inhibiting-effective amount which is an HIV-1 protease inhibiting-effective amount. The HIV-1 protease inhibiting-effective amount can be effective toward normal or mutant HIV-1 protease inhibiting-effective amount. The mutant HIV-1 protease inhibiting-effective amount, for example, can be an 84V mutant HIV-1 protease inhibiting-effective amount. The mutant HIV-1 protease inhibiting-effective amount also can be, for example, an 82F/84V mutant HIV-1 protease inhibiting-effective amount. Alternatively, the mutant HIV-1 protease inhibiting-effective amount can be, for example, a 32I mutant HIV-1 protease inhibiting-effective amount.

The therapeutically effective amount also can be a cathepsin D inhibiting-effective amount (e.g., for the treatment of cancer) or a plasmepsin inhibiting-effective amount (e.g., for the treatment of malaria).

The present invention further provides a method of preventing or treating a retroviral infection comprising administering a retroviral protease inhibiting-effective amount of at least one compound of the present invention. The method of the present invention can be applied, for example, toward the treatment or prevention of an HIV infection and, more particularly, an HIV-1 infection in a mammal, particularly a human. In accordance with the method of the present invention, an aspartic picotease-inhibiting effective amount of one or more of the present inventive compounds can be administered to a mammal infected with, or who may come in contact with, a retrovirus, particularly HIV, and more particularly HIV-1. The compound(s) of the present invention can be administered alone or in combination with one or more other antiretroviral compounds such as, for example, AZT, ddI, ddC, D4T, lamivudine or 3TC. When a retroviral protease inhibiting-effective amount of one or more compounds of the present invention is (are) administered, L2h retroviral proliferation can be effectively inhibited.

The dose administered to an animal, particularly a human, in the context of the present invention should be sufficient to effect a therapeutic response in the animal over a reasonable time frame. The dose can be determined by the strength of the particular composition employed and the condition of the animal, as well as the body weight of the animal to be treated. The size of the dose also can be determined by the existence, nature, and extent of any adverse side-effects that might accompany the administration of a particular compound. Other factors which effect the specific dosage include, for example, bioavailability, metabolic profile, and the pharmacodynamics associated with the particular compound to be administered in a particular patient.

One skilled in the art will recognize that the specific dosage level for any particular patient will depend upon a variety of factors including, for example, the activity of the specific compound employed, the age, body weight, general health, sex, diet, time of administration, route of administration, rate of excretion, drug combination, CD4 count, the potency of the active compound with respect to the particular retroviral strain to be inhibited, and the severity of the symptoms presented prior to or during the course of therapy. What constitutes a retroviral protease-inhibiting amount, particularly a HIV protease-inhibiting amount, and more particularly an HIV-1 protease-inhibiting amount, of one or more compounds of the present invention, alone or in combination with one or more other currently available antiretroviral compounds can be determined, in part, by use of one or more of the assays, examples of which are described herein. Similarly, whether or not a given retrovirus is inhibited by a retroviral protease-inhibiting amount of a compound of the present invention can be determined through the use of one or more of the assays described herein, or in the scientific literature, or using any other suitable method or methods known in the art.

One skilled in the art will appreciate that suitable methods of administering the compounds and pharmaceutical compositions of the present invention to an animal are available, and, although more than one route can be used to administer a particular composition, a particular route can provide a more immediate and more effective reaction than another route. One or more of the present inventive compounds, alone or in combination with one or more other antiretroviral therapies or compounds, also can be administered to a mammal, in particular a human, as a prophylactic method to prevent a retroviral, particularly an HIV, more particularly an HIV-1, infection.

The present invention further provides a method of preventing or treating a malarial infection in which a plasmepsin inhibiting-effective amount of at least one compound of the present invention, alone or in combination with another antimalarial agent, is administered to a patient in need thereof. The dose administered to an animal, particularly a human, in the context of the present invention should be sufficient to effect a therapeutic response in the animal over a reasonable time frame. The dose will be determined by the strength of the particular composition employed and the condition of the animal and other factors described herein with respect to the treatment of HIV. What constitutes a plasmepsin inhibiting-effective amount of one or more compounds of the present invention can be determined, in part, by the use of one or more of the assays described herein or by any other suitable method or methods known in the art. Similarly, whether or not a given malarial parasite is inhibited by a compound of the present invention can be determined through the use of one or more assays. Suitable assays include, for example, those described herein or in the scientific literature (including enzyme inhibition and antimalarial assays). What constitutes a plasmepsin inhibiting-effective amount also can be determined, in part, by clinical evaluation, for example, by reduction of one or more symptoms associated with malaria, resistance to malarial infection relative to an untreated control group, or the like.

The present invention further provides a method of preventing or treating cancer comprising administering a cathepsin D inhibiting-effective amount of at least one compound of the present invention, alone or in combination with another anticancer agent or antiproliferative compound or the like. In a preferred embodiment, the method of the present invention is applied toward the treatment or prevention of breast cancer.

For the treatment of cancer, the compounds of the present invention can be administered alone or in combination with other chemotherapeutic compounds. Additional chemotherapeutic compounds include, for example, doxifluridine, fluorouracil, methotrexate, hydroxyurea, cytarabine, cisplatin, carboplatin, mitimycins, cyclophosphamide, ifosphamide, chloroambucil, thiotepa, melphalan, doxorubicin, epirubicin, mitoxanthrone, bleomycin, daunorubicin, etoposide, vincristine, vindesine, tamoxifen, leuprolide, flutamide, goserelin, medroxyprogesterone, estramustine, megestrol acetate, and the like, as well as admixtures and combinations thereof. The individual daily dosages for these combinations can range from about one-fifth of the minimally recommended clinical dosages to the maximum recommended levels for the entities when they are given singly.

The following examples further illustrate the present invention but, of course, should not be construed as in any way limiting its scope.

SYNTHESIS EXAMPLES

The following protocols were used in the synthesis of the compounds of the present invention. Proton nuclear magnetic resonance ($^1$H NMR) spectra were recorded on a Varian XL-200 or VXR-500S MHz spectrometer. $^1$H NMR spectral data are reported in δ ppm scale relative to TMS. High resolution mass spectra were recorded on a VG70-250 and FAB mass spectra on a VG ZAB-2F (Manchester, England) mass spectrometer. Flash chromatography was performed on silica gel (230–400 mesh, E. Merck). HPLC analysis were carried out using a Hewlett Packard 1050 chromatograph using an analytical column YMC-Pack ODS-AQ (C18)(250×4.6 mm, S-5, 120 Å) reverse phase column and methanol/water (0.05% trifluoroacetic acid) mixtures as mobile phase (gradient 50–100% of methanol during 30 min.). Thin-layer chromatography was performed on silica gel F-254 plates (0.25; 0.50 @ 1 mm Whatman) and visualized using sulfuric acid or chlorine or ninhidrin/TDM (4,4'-tetramethyldiaminodiphenylethane) and UV methods. TLC solvent systems used are: A (ethyl acetate-hexane, 7:3), B (ethyl acetate-hexane, 1:3), C (ethyl acetate-hexane, 1:1), D (chloroform-methanol, 95:5), E (chloroform-methanol, 9:1). Solvents were of reagent grade.

Example 1

This example illustrates the synthesis of (L) -N,N-dibenzylphenylalanine benzyl ester, compound (2) of FIG. 1. To a homogeneous solution of L-phenylalanine (75 g, 0.45 moles), $K_2CO_3$ (200 g, 1.45 moles) , and water (300 mL) was added benzyl chloride (182 g, 1.44 moles) The solution was heated at reflux for 16 h (prolonged reflux is necessary to destroy excess BnCl). Heptane (200 mL) and water (150 mL) were added to the cooled reaction mixture. The organics were separated and washed twice with 150 mL of water/methanol (2/1 v/v). The organics were concentrated in vacuo to afford 190 g of a lite yellow oil which was >90% pure by HPLC. An analytical sample was prepared by flash chromatography (10% EtOAc/hexanes): $R_1$, 0.65 (25% Et)Ac/hexanes); $^1$H NMR (CDCl$_3$) δ 7.5–7.0 (m, 20H) , 5.3 (d, 1H, J=13.5 Hz), 5.2 (d, 1H, J=13.5 Hz), 4.0 (d, 2H, J=15 Hz), 3.8 (t, 2H, J=8.4 Hz), 3.6 (d, 2H, J=15 Hz), 3.2 (dd, 1H, J=8.4, 14.4 Hz).

Example 2

This example illustrates the synthesis of (4S)-4-dibenzylamino-3-oxo-5-phenyl-pentanonitrile, compound (3) of FIG. 1. The crude ester 4 (190 g, 90% pure, 390 mmol) was dissolved in THF (510 mL) and cooled to −45° C. under nitrogen. To a separate flask was charged−95% sodium amide (38.4 g, 940 mmol) under nitrogen followed by THF (425 mL). The slurry was cooled to −45° C. and CH$_3$CN (52 mL, 1.0 mol) was added over 15 minutes. The anion solution was added to the ester solution over 15 minutes and was then stirred at −45° C. for 2 h. The reaction was quenched with 900 mL of 25% w/v aqueous citric acid. The organics were separated and washed with 900 mL of 20% w/v brine. The organics were filtered and concentrated in vacuo. The residue was crystallized from 500 mL of ethanol (denatured with toluene to afford 112 g (78%, 67% for two steps) of a white solid: mp 84–85° C.; R, 0.55 (25% EtOAc/hexanes) ; $^1$H NMR (CDCl$_3$) δ 7.3 (m, 15H), 3.9 (d, 1H, J=19.5 Hz), 3.8 (d, 2H, J=4.0, 13.5 Hz), 3.6 (d, 2H, J=13.5 Hz), 3.5 (dd, 1H, J=4.0, 10.5 Hz), 3.2 (dd, 1H, J=10.5, 13.5 Hz), 3.0 (dd, 1H, J=4.0, 13.5 Hz), 3.0 (d, 1H, J=19.5 Hz).

Example 3

This example illustrates the synthesis of (7S)-4-amino-7-dibenzylamino-2-methyl-6-oxo-8-phenyl-oct-4-ene, compound (4) of FIG. 1. To a solution of nitrile 5 (53 g, 144 mmol) in 150 mL of tetrahydrofuran at 10° C. was added ) a 2.0 M solution of isobutylmagnesium chloride in ether (210 mL, 420 mmol). The solution was warmed to 25° C. and was stirred for 16 h. The reaction was cooled to 5° C. and was quenched by slow addition of 10% aqueous citric acid (770 mL, w/v). The organic layer was separated and washed with ½ sat'd. aqueous NaCl (500 mL), was dried over Na$_2$SO$_4$ (5 g) and was concentrated in vacuo: MS m/z 427 (M+H)$^+$; $^1$H NMR (CDCl$_3$); δ 0.91 (d, J=6.5 Hz, 3H) 0.94 (d, J=6.5 Hz, 3H), 1.77–1.84 (m, 1H), 1.88–1.94 (m, 2H), 2.98 (dd, J=13.7; 7.7 Hz, 1H) , 3.12 (dd, J=13.6; 7.5 Hz, 1H), 3.5 (t, J=7.2 Hz, 1H), 3.66 (d, J=14.0 Hz, 2H), 3.85 (d, J=14.1 Hz, 1H), 4.94 (s, 1H), 5.02 (s, 1H), 7.09–7.23 (m, 15H), 9.88 (s, 1H).

C (CDCl$_3$) 197.5, 164.3, 140.1, 139.4, 129.4, 128.6, 128.0, 127.9, 126.6, 125.6, 96.6, 66.3, 54.3, 45.8, 33.2, 27.7, 22.3, 22.2.

Example 4

This example illustrates the synthesis of (2S,3S,5S)-5-amino-2-(dibenzylamino)-3-hydroxy-7-methyl-1-phenyloctane, compound (6) of FIG. 1. A suspension of sodium borohydride (8.2 g, 216 mmol) in tetrahydrofuran (500 mL) was cooled to −5° C. Methanesulfonic acid (34 mL, 526 mmol) was added at a rate such that the temperature remained below 5° C. The reaction was cooled to 0° C. and a solution of compound (4) of FIG. 1 (37 g, 86 mmol) in THF (80 mL) and iPrOH (43 mL) was added. The mixture was stirred for 14 h at 10° C.

To a separate flask was added sodium borohydride (13.1 g, 344 mmol) and THF (200 mL). After cooling to 0° C., 33 mL (430 mmol) of trifluoroacetic acid was added slowly. The solution was stirred 30 min. at 10° C. and was then added to the previous action at a rate such that the temperature remained below 15° C. This was stirred for 4 h, cooled to 10° C., and quenched with 3N NaOH (325 mL). After adding tert-butyl methyl ether (375 mL), the organic layer was separated and was washed with 0.5N NaOH (375 mL), 20% w/v aqueous NH$_4$Cl (375 mL) , and 6% w/v aqueous NaCl (2×375 mL). The organics were dried over sodium sulfate and concentrated in vacuo. This afforded 37 g of a mixture of diastereomers as a yellow oil; Rf 0.28 (95:3:2:CHCl$_3$:MeOH:isopropylamine)

Example 5

This example illustrates the synthesis of (2S,3S,5S)-2,5-diamino-3-hydroxy-7-methyl-1-phenyloctane dihydrochloride, compound (7) of FIG. 1. A solution of crude compound (6) of FIG. 1 (2.8 g, 6.5 mol), methanol (10 mL), aqueous ammonium formate (2 g in 1 mL water), and 5% palladium on carbon (1 g) was heated to reflux for 6 h. The cooled suspension was filtered through a bed of diatomaceous earth and the cake was washed with methanol (2×10 mL). The filtrate was concentrated in vacuo to an oil. The residue was dissolved in EtOAc (50 mL) and was washed with 1N NaOH (10 mL), with 20% aqueous brine, and with water. The organics were concentrated in vacuo. To the oil was added iPrOH. (10 mL) and conc. HCl (aq, 1 mL). The suspension was heated to reflux for 1 h, cooled over 6 h to 25° C., and held at that temperature for 12 h. The slurry was filtered, and the cake was washed with ethyl acetate: MS m/z 251 (M+H)$^+$; $^1$H NMR (CD$_3$QD); δ 0.94 (d, J=6.5 Hz, 3H), 0.95 (d, J=6.5 Hz, 3H), 1.42–1.51 (m, 2H) , 1.64–1.72 (m, 1H) , 1.73–1.86 (m, 2H) , 2.92 (dd, J=14.1; 7.4 Hz, 1H), 3.05 (dd, J=14.1; 7.2 Hz, 1H), 3.34–3.44 (m, 2H), 3.82–3.92 (m, 1H), 3.91 (dt, J=10.8, 3.4 Hz, 1H), 7.28–7.43 (m, 5H). $^{13}$C(CDCl$_3$) δ 137.1, 130.3, 130.6, 128.6, 69.2, 58.7, 50.5, 43.5, 37.6, 37.1, 25.4, 23.1, 22.6.

Example 6

This example illustrates the synthesis of (2S,3S,5S)-5-[N-(tert-butyloxycarbonyl)amino]-2-[N-(dibenzyl)amino]-3-hydroxy-7-methyl-1-phenyloctane, compound (8) of FIG. 2. A solution of (2S,3S,5S)-5-amino-2-[(N-dibenzyl)amino]-3-hydroxy-7-methyl-1-phenyloctane (9.46 g, 22 mmol), di-tert-butyl carbonate (5.66 g, 26 mmol) and diisopropylethylamine (2.82 g, 3.82 mL, 22 mmol) in methylene chloride (400 mL), was stirred at room temperature for 12 h. Solvents were evaporated and residue was diluted with ethyl acetate and sequentially washed with aqueous NaHCO$_3$, aqueous KHSO$_4$, brine, dried on MgSO$_4$ and concentrated in vacuo. Yield 11.8 g; thick liquid purified on flash chromatography using hexane and ethyl acetate mixtures (0 to 10% of ethyl acetate). Yield of pure product after chromatography 8.74 g (75%); TLC [R$_f$=0.51 (B)]; HPLC (t$_{ret}$=21.26 min.); MS m/z 531 (M+H)$^+$; $^1$H NMR (CDC13); δ 8 0.88 (dd, J=6.3; 3.9 Hz, 6H), 1.14–1.21 (m, 1H), 1.24–1.32 (m, 2H), 1.35–1.47 (m, 1H), 1.49 (s, 9H), 1.57–1.65 (m, 1H), 2.83–2.86 (m, 1H), 2.94 (dd, J=14.2; 4.5 Hz, 1H), 3.04 (dd, J=14.2; 8.7 Hz, 1H), 3.61 (d, J=14.1 Hz, 2H), 3.75 (d, J=14.1 Hz, 2H), 3.80–3.83 (m, 1H), 3.95 (d, J=11 Hz, 1H), 4.10 (s, 1H), 4.29 (d, J=9.1 Hz, 1H), 7.10–7.26 (m, 15H).

Example 7

This example illustrates the synthesis of (2S,3S,5S)-2-amino-5-[N-tert-butyloxycarbonylamino]-3-hydroxy-7-methyl-1-phenyloctane. A solution of (2S,3S,5S)-5N-(tert-butyloxycarbonyl)amino-2-(N-dibenzyl)amino-3-hydroxy-7-methyl-1-phenyloctane (compound (8) of FIG. 1, 8.65 g, 16.3 mmol), aqueous ammonium formate (8 g in 10 mL of water ), 50 Palladium on carbon (2.2 g) in methanol (100 mL) was heated to reflux for 6 h. The cooled suspension was filtered through the Celite 521, washed with methanol and concentrated in vacuo. The residue was dissolved in ethyl acetate (150 mL) and was washed with 1N NaOH (50 mL), brine, dried over potassium carbonate filtereted and concentrated to give white solid product. Yield 5.11 g (91%), mp 118–119° C.; [R$_f$=0.21 (E)]; HPLC (t$_{ret}$=12.1 min.); MS m/z 351M+H)+; $^1$H NMR (CDCl$_3$) δ 0.90 (dd, J=6.7; 2.4 Hz, 6H), 1.07–1.14 (m, 1H), 1.22–1.28 (m, 3H), 2.70 (dd, J=13.5; 9.9 Hz, 1H), 2.80–2.84 (m , 1H), ), 3.07 (m, 1H), ), 3.37 (dd, J=13.2 Hz, 2H), 3.62 (m, 2H), 3.91 (d, J=13.2 Hz, 2H), 4.39 (bs, 1H), 4.62 (bs, 1H), 7.20–7.32 (m, 15H).

Example 8

This example illustrates the synthesis of (2S,3S,5S)-5-[N-tert-butyloxycarbonylamino]-2-[N-[2-(2,6- dimethylphenoxy)acetyl]amino]-3-hydroxy-7-methyl-1-phenyloctane (compound (15) of Table 1). To a stirred solution of (2S,3S,5S)-5-amino-5-[N-tert-butyloxycarbonylamino]-3-hydroxy-7-methyl-1-phenyloctane (350 mg, 1 mmol), 2-(1H-benzatriazole-1-yl)-1,1,3,3-tetramethyluronium tetrafluroborate (TBTU, 329 mg, 1 mmol), 1-hydroxybenzotriazole (HOBt, 153 mg, 1 mmol) and (2,6-dimethylphenoxy)acetic acid (216 mg, 1.2 mmol), in 50 mL of dimethylformamide (DMF) was added diisopropylethyl amine (DIPEA, 322 mg, 435 mL, 2.5 mmol). The reaction mixture was stirred at room temperature for 5 h. The solvent was removed under reduced pressure, residue was taken up in ethyl acetate and washed sequentially with aqueous $KHSO_4$, brine, aqueous NaHCO3, and brine. The organic layer was dried over $MgSO_4$ and concentrated under reduced pressure to provide crude (2S,3S,5S)-5-[N-tert-butyloxycarbonylamino]-2-[N-[2-(2,6-dimethylphenoxy)acetyl]amino]-3-hydroxy-7-methyl-1-phenyloctane. The crude product was crystallized from ethyl acetate : hexane (1:3); Yield 420 mg (82%); TLC [$R_f$=0.19(B)]; HPLC ($t_{ret}$=25.56 min.); MS m/z 513 (M+H)$^+$; H NMR (CDCl$_3$) δ 0.86 (d, J=6.5 Hz, 3H), 0.87 (d, J=6.4 Hz, 3H), 1.18–1.32 (m, 2H), 1.42 (s, 9H), 1.59–1.63 (m, 2H), 2.18 (s, 6H), 3.01 (bd, 2H), 3.61–3.68 (m, 1H), 3.80 (m, 1H), 4.19 (d, J=2.3 Hz, 2H), 4.26 (m, 1H), 4.52 (m, 1H), 6.94 (m, 1H), 6.98 (m, 2H), 7.26–7.31 (m, 5H). $^{13}$C NMR (CDCl$_3$) d168.7, 156.3, 154.2, 138.1, 130.3, 129.2, 128.9, 128.3, 126.3, 124.5,79.6, 70.1, 69.9,54.5, 47.4, 45.4, 42.7, 38.3, 28.3, 24.6, 22.9, 21.9, 16.1

Example 9

This example describes the synthesis of (2S,3S,5S)-2-[N-[2-(2,6-dimethylphenoxy)acetyl]amino]-5-[N-[[3-methyl-2S-(2-oxo-tetrahydropyrimidin-1-yl-butyryl)amino]-3-hydroxy-7-methyl-1-phenyloctane (compound (16) of Table 1. The compound (2S,3S,5S)-5-[N-tert-butyloxycarbonylamino]-2-[N-[2-(2,6-dimethylpheroxy)acetyl]amino]-3-hydroxy-7-methyl-1-phenyloctane (compound (15) of Table 1, 120 mg, 0.23 mmol) was dissolved in solution of trifluoroacetic acid (3. mL) and stirred at room temperature for 30 min., after which solvents were evaporated. The evaporation was repeated 3 times with ethyl ether and finally dried under vacuum, MS m/z 413 (M+H)$^+$;

The resulting salt of (2S,3S,5S)-5-amino-2-[N-[2-(2,6-dimethylphenoxy)acetyl]amino]-3-hydroxy-7-methyl-1-phenyloctane, was added to the solution of TBTU (86 mg, 0.27 mmol), HOBt, (41 mg, 0.27 mmol), 3-methyl-2S-oxo-tetrahydropyrimidin-1-yl-butyric acid (54 mg, 0.27 mmol), DIPEA (139 mg, 189 mL, 1.08 mmol) in 10 mL of dimethylformamide (DMF). The reaction mixture was stirred at room temperature for 4 h. The solvent was removed under reduced pressure, residue was taken up in ethyl acetate and washed sequentially with aqueous $KHSO_4$, brine, aqueous NaHCO3, and brine. The organic layer was dried over $MgSO_4$ and concentrated under reduced pressure. Yield 160 mg; thick liquid purified on Silicagel circular column using ethyl acetate and methanol mixtures (0 to 10% of methanol). Yield of pure product 68 mg (50%); TLC [$R_f$=0.19(B)]; HPLC ($t_{ret}$=23.3 min.); MS m/z 617 (M+Na)$^+$; H NMR (CDC13) δ 0.82 (d, J=6.5 Hz, 3H), 0.85 (d, J=6.2 Hz, 3H), 0.86 (d, J=6 Hz, 3H), 0.89 (d, J=6.5 Hz, 3H), 1.18–1.25 (m, 2H) , 1.37–1.43 (m, 1H), 1.51–1.59 (m, 1H), 1.64 (t, J=6.0 Hz, 2H) , 1.77–1.84 (m, 1H) , 1.85–1.92 (m, 1H), 2.17 (s, 6H), 2.23–2.32 (m, 2H), 3.00 (d, J=7.3 Hz, 2H), 3.19–3.24 (m, 3H), 3.33–3.37 (m, 1H), 3.79 (bt, 1H), 3.86–3.93 (m, 1H), 4.19 (d, J=14 Hz, 2H), 4.23–4.26 (m, 1H), 4.27–4.31 (m, 1H), 4.55 (bs, 1H), 5.05 (bs, 1H), 6.92 (bs, 1H) , 6.93 (dd, J=6.3 Hz, 8.4, 1H) , 6.98 (bd, 2H), 7.18–7.22 (m, 1H), 7.25–7.28 (m, 4H).

Example 10

This example illustrates the synthesis of (2S, 3S, 5S)-5-[N-[[3-methyl-2S-(2-oxo-tetrahydropyrimidin-1-yl)] butyryl]amino]-2-(N-[(thiazol-5-yl-methoxy)carbonyl] amino]-3-hydroxy-7-methyl-1-phenyloctane (compound (19) of FIG. 6 and compound (19) of Table 1). To a stirred solution of (2S,3S,5S)-2-amino-5-[N-[[3-methyl-2S-(2-oxo-tetrahydropyrimidin-1-yl) butyryl[amino]3-hydroxy-7-methyl-1-phenyloctane (0.14 mmol) in methylene chloride (25 mL) was added (thiazol-5-yl-methyl)-N-succinimidylcarbonate (43 mg, 0.14 mmol) and DIPEA (22 mg, 30 mL, 0.15 mmol). The reaction mixture was stirred at room temperature for 4 h. Solvent was removed under reduced pressure, residue was taken up in methylene chloride and washed sequentially with aqueous $KHSO_4$, brine, aqueous NaHCO$_3$, and brine. The organic layer was dried over $Na_2SO_4$ and concentrated under reduced pressure to provide crude 120mg of product Purified by preparative HPLC; Yield 41 mg (54); TLC [$R_f$=0.21(E)]; HPLC (rt=16.6 min.), MS m/z 596 (M+Na)$^+$; $^1$H NMR (CDOD$_3$) δ 0.86–0.89 (m, 12H) , 1.17–1.22 (m, 1H), 1.32–1.37 (m, 1H), 1.52–1.55 (m, 3H), 1.77–1.84 (m, 4H), 1.87–1.96 (m, 1H), 2.19–2.26 (m, 1H), 2.77–2.85 (m, 1H), 3.21–3.28 (m, 4H) , 3.38–3.43 (m, 1H), 3.64 (dt, J=7.0 Hz; 1.9 Hz, 1H), 4.09–4.15 (m, 1H), 4.25–4.28 (m, 1H), 4.30 (d, J=11.3 Hz, 1H), 4.85 (m, 2H), 7.13–7.16 (m, 1H), 7.20–7.26 (m, 6H).

Example 11

This example describes the synthesis of (2S,3S,5S)-2-[(N-[2-(2,6-dimethylphenoxy)acetyl]amino]-5-[N-(3S-tetrahydrofuranyloxycarbonyl)amino]-3-hydroxy-7-methyl-1-phenyloctane (compound (26) of Table 1). The compound was prepared following a similar procedure described in Example 10; substituting (3S-terahydrofuranyl)-N-succinimidylcarbonate for (thiazol-5-yl-methyl)-N-succinimidylcarbonate: Yield (46i); TLC [$R_f$=0.38 (A)]; MS m/z 527 (M+H)$^+$; H NMR (CDCl$_3$) δ 0.86 (d, J=6.5, 6H), 1.22–1.27 (m, 1H), 1.32–1.39 (m, 1H), 1.56–1.66 (m, 3H), 1.93–1.98 (m, 1H), 2.01–2.17 (m, 1H), 2.19 (s, 6H), 2.99–3.04 (m, 2H), 3.71 (m, 1H), 3.79–3.91 (m, 5H), 4.21–4.26 (m, 3H), 4.65 (d, J=8.2 Hz, 1H), 5.22 (bt, 1H), 6.95 (dd, J=6.2 Hz, 8.4, 1H), 7.00 (bd, 2H), 7.20–7.33 (m, 5H).

Example 12

This example describes the synthesis of (2S,3S,5S)-2-[N-[2-(2,6-dimethylphenoxy)acetyllamino-5-[N(morpholine-4-carbonyl)amino]-3-hydroxy-7-methyl-1-phenyloctane (compound (27) of Table 1). To a stirred solution of (2S, 3S,5S)-5-amino-2-[(N-[2-(2,6-dimethyphenoxy)acetyl] amino]-3-hydroxy-7-methyl-1-phenyloctane (88 mg, 0.22 mmol) and diisopropylethylamine (55 μL, 0.34 mmol) in acetonitrile (10 mL), was added a solution of 4-morpholinecarbonyl chloride (30 μL, 0.26 mmol) in acetonitrile (5 mL) at room temperature for 3 h. Solvents were evaporated and the residue was diluted with ethyl acetate and sequentially washed with aqueous NaHCO$_3$, aqueous $KHSO_4$, brine, dried on MgSO$_4$ and concentrate in vacuo. Crude product was purified on preparative TLC using hexane and ethyl acetate mixtures (70% of ethyl acetate). Yield of pure product after chromatography 77 mg (70%); TLC [$R_f$=0.30 (A)]; HPLC ($^t$ret=21.7 min.); MS m/z 548

(M+Na)⁺; H NMR (CDCl₃) δ 0.86 (d, J=6.5, 3H), 0.88 (d, J=6.5, 3H), 1.25–1.31 (m, 1H), 1.37–1.43 (m, 1H), 1.54–1.66 (m, 2H), 2.20 (s, 6H), 3.01 (dddd, J=7.8 Hz, 13.6, 14.8, 2H), 3.27–3.36 (m, 4H), 3.67(bt, 4H), 3.79 (bt, 1H), 4.18 (bt, 1H), 4.20 (s, 2H), 4.40 (d, J=7.3 Hz, 1H), 4.96 (bd, 1H), 6.93 (dd, J=6.2 Hz, 8.5, 1H), 6.98 (bd, 2H), 7.2–7.30 (m, 5H).

Example 13

This example describes the synthesis of (2S,3S,5S)-5-[N-[[N'-(tert-butyl)amino]carbonyl]amino]-2-[N-[2-(2,6-dimethylphenoxy)acetyl]amino]-3-hydroxy-7-methyl-1-phenyloctane (compound (28) of Table 1). The compound was prepared following a similar procedure described in Example 12; using tert-butylisocyanate instead of 4-morpholinecarbonyl chloride: Yield (59%); TLC [R$_f$=0.24 (C)]; HPLC ($^t$ret=23.9 min.); MS m/z 534 (M+Na)⁺; H NMR (CDCl₃) δ 0.86 (d, J=6.6 Hz, 6H), 1.18–1.25 (m, 1H), 1.27–1.33 (m, 1H), 1.31 (s, 9H), 1.54–1.62 (m, 4H), 1.64 (bs, 1H), 2.19 (s, 6H), 3.02 (t, J=7.9 Hz, 2H), 3.65–3.71 (m, 1H), 3.80(t, J=6.1 Hz, 4H), 4.06 (d, J=7.9 Hz, 1H), 4.17–4.23 (m, 1H), 4.20 (s, 2H), 4.29 (s, 1H), 4.90 (s, 1H), 6.94 (dd, J=6.1, 8.4 Hz, 1H), 6.99 (bd, 2H), 7.19–7.22 (m, 1H), 7.29–7.31 (m, 4H).

Example 14

This example illustrates the synthesis of (2S, 3S, 5S)-2-[N-[2-(2,6-dimethylphenoxy)acety2]amino]-5-[N-[2S-(2-oxopyrimidinyl)-4-carbonyl]amino]-3-hydroxy-7-methyl-1-phenyloctane (compound.(29) of Table 1). The compound was prepared following a similar procedure described in Example 9, except that 2S-(2-oxopyrimidynyl)-4-carboxylic acid was used as the acid component: Yield (47i); TLC [R$_f$=0.54 (E)]; HPLC ($^t$ret=19.9 min.); MS m/z 539 (M+H)⁺; H NMR (CDCl₃) δ 0.87 (d, J=6.5 Hz, 3H), 0.89 (d, J=6.4 Hz, 3H), 1.24–1.29 (m, 2H), 1.41–1.47 (m, 1H), 3) 1.51–1.56 (m, 1H), 1.59–1.66 (m, 1H), 1.77–1.81 (m, 1H), 1.97–2.03 (m, 1H), 2.12–2.18 (m, 1H), 2.16 (s, 6H), 2.90 (dd, J=8.4, 13.7 Hz, 1H), 3.01 (dd, J=6.6, 13.7 Hz, 1H), 3.09–3.14 (m, 1H), 3.17–3.20 (m, 1H), 3.79 (m, 1H), 3.92–3.95 (m, 1H), 4.04–4.10 (m, 1H), 4.11 (d, J=14.9 Hz, 1H), 4.21–4.25 (m, 1H), 4.24 (d, J=14.9 Hz, 1H), 4.56 (m, 1H), 6.58 (m, 1H), 6.94 (dd, J=5.9, 8.6 Hz, 1H), 6.98–6.99 (m, 2H), 7.17–7.22 (m, 2H), 7.24–7.29 (m, 3H).

Example 15

This example illustrates the synthesis of (2S, 3S, 5S)-2-[N-[2-(2,6-dimethylphenoxy)acetyl]amino]-5-[N-[N'-(pyridine-2-methoxycarbonyl)valinyl]amino]-3-hydroxy-7-methyl-1-phenyloctane (compound (30) of Table 1). The compound was prepared following a similar procedure described in Example 9, except that N'-(pyridine-2-methoxycarbonyl)valine was used as the acid component: Yield (49%); TLC [R$_f$=0.50 (D)]; HPLC (t$_{ret}$=21.3 min.); MS m/z 546 (M+H)⁺; H NMR (CDCl₃) δ 0.84 (d, J=7.4 Hz, 3H), 0.85 (d, J=7.0 Hz, 3H), 0.89 (d, J=6.8 Hz, 3H), 0.93 (d, J=6.6 Hz, H), 1.22–1.28 (m, 2H), 1.39–1.45 (m, 1H), 1.51–1.57 (m, 1H), 1.59–1.63 (m, 1H), 1.70 (m, 1H) 1.73 (bd, 1H), 2.17 (s, 6H), 2.94–3.03 (m, 2H), 3.79 (bd, 1H), 3.91–3.94 (m, 2H), 4.14 (d, J=14.7 Hz, 1H), 4.21 (d, J=14.8 Hz, 1H), 4.23 (m, 1H), 5.17 (d, J=13.1 Hz, 1H), 5.27 (d, J=13.3 Hz, 1H), 5.35 (bd, 1H), 6.15 (bd, 1H), 6.94 (dd, J=6.1, 8.5 Hz, 1H), 6.98–7.00 (m, 2H), 7.19–7.23 (m, 2H), 7.26–7.33 (m, 5H), 7.69, (t, J=7.7 Hz, 1H) 8.58 (d, J=4.7, 1H).

Example 16

This example illustrates the synthesis of (2S, 3S, 5S)-5-[N-(4-aminobenzoyl)amino]-2-[N-[2-(2,6-dimethylphenoxy)acetyl]amino]-3-hydroxy-7-methyl-1-phenyloctane (compound (31) of Table 1). The compound was prepared following a procedure similar to that described in Example 9, except that 4-nitrobenzoic acid was used as the acid component. Following the peptide coupling the nitro group was reduced. The mixture of (2S, 3S, 5S)-2-[N-[2–2,6-dimethylphenoxy)acetyl]amino]-5-[N-(4-nitrobenzoyl)amino]-3-hydroxy-7-methyl-1-phenyloctane (80 mg, 0.13 mmol), and 10% Palladium on carbon (10 mg) in ethanol (50 mL) stirred vigorously under an H₂ atmosphere for 6 h. The suspension was filtered through the Celite 521, washed with ethanol and concentrated in vacuo to give white solid product. Yield (49%); TLC [R$_f$=0.21 (C)]; HPLC ($^t$ret=20.0 min.); MS m/z 532 (M+H)⁺; H NMR (CDCl₃) δ 0.88 (d, J=6.6 Hz, 3H), 0.90 (d, J=6.7 Hz, 3H), 1.34–1.39 (m, 1H), 1.49–1.55 (m, 1H), 1.62–1.67 (m, 1H), 1.71–1.73 (m, 2H), 2.13 (s, 6H), 3.00 (dd, J=7.9, 13.7 Hz, 1H), 3.04 (dd, J=7.3, 13.7 Hz, 1H), 3.84 (t, J=5.8 Hz, 1H), 4.03–4.09 (m, 2H), 4.16 (d, J=6.1 Hz, 1H), 4.20–4.26 (m, 2H), 4.81 (m, 1H), 5.99 (bd, 1H), 6.65 (d, J=8.4 Hz, 2H), 6.90 (dd, J=5.5, 8.8 Hz, 1H), 6.94 (bd, 2H), 7.19–7.22 (bt, 1H), 7.26–7.31 (m, 5H), 7.56 (d, J=8.4 Hz, 2H)

Example 17

This example illustrates the synthesis of (2S, 3S, 5 5S)-5-[N-(3-aminobenzoyl)amino-2-[N-[2-(2,6-dimethylphenoxy)]acetyl]amino]-3-hydroxy-7-methyl-1-phenyloctane (compound (32) of Table 1). The compound was prepared following a procedure similar to that described in Example 16, except that 3-nitrobenzoic acid was used as the acid component: TLC [R$_f$=0.20 (C)]; HPLC ($^t$ret=18.7 min.); MS m/z 532 (M+H)⁺; H NMR (CDCl₃) δ 0.87 (d, J=6.7 Hz, 3H), 0.91 (d, J=6.6 Hz, 3H), 1.32–1.37 (m, 1H), 1.49–1.53 (m, 1H), 1.62–1.69 (m, 1H), 1.72–1.74 (m, 2H), 2.15 (s, 6H), 3.03 (dd, J=7.9, 13.7 Hz, 15 1H), 3.05 (dd, J=7.3, 13.7 Hz, 1H), 3.86 (t, J=5.8 Hz, 1H), 4.03–4.08 (m, 2H), 4.14 (d, J=6.1 Hz, 1H), 4.20–4.26 (m, 2H), 4.83 (m, 1H), 5.99 (m, 1H), 6.65 (d, J=8.4 Hz, 2H), 6.91 (dd, J=5.5, 8.8 Hz, 1H), 6.94 (bd, 2H), 7.19–7.22 (bt, 1H), 7.26–7.31 (m, 5H), 7.56 (d, J=8.4 Hz, 2H)

Example 18

This example illustrates the synthesis of (2S,3S,5S)-2-[N-(benzyloxycarbonyl)amino])-5-[N-[[3-methyl-2S-(2-oxo-tetrahydropyrimidin-1-yl)]butyryl]amino]-3-hydroxy-7-methyl-1-phenyloctane (compound (18) of FIG. 6 and Table 1) starting from compound 17, as shown in FIG. 6. The compound was prepared following a similar procedure described in Example 9, except that 3-methyl-2S-oxo-30 tetrahydropyrimidin-1-yl-butyric acid was used as the acid component. The crude product of this reaction was purified on HPLC. The main product (compound (18) of Table 1) exhibited following physical and spectral data: TLC [R$_f$= 0.80 (E)]; HPLC ($^t$ret=22.3 min.); MS m/z 589 (M+Na)⁺; H NMR (CDCl₃ δ 0.84 (dd, J=6.6, 2.5 Hz, 6H), 0.89 (d, J=6.6 Hz, 3H), 0.92 (d, J=6.4 Hz, 3H), 1.13–1.18 (m, 1H), 1.25 (bs. 1H), 1.34–1.4 (m, 2H), 1.47–1.54 (m, 1H), 1.55–1.60 (m, 6H), 1.80–1.90 (m, 1H), 2.21–2.28 (m, 2H), 2.83, (m, 6H), 2.87 (d, J=7.6 Hz, 1H), 3.15 (m, 1H), 3.18–3.23 (m, 1H), 3.39–3.44 (m, 1H), 3.57–3.59 (m, 1H), 3.76–3.88 (m, 1H), 4.14 (d, J=11.4 Hz, 1H), 4.43 (d, J=3.5 Hz, 1H), 4.56 (s, 1H), 5.05 (bs, 2H), 5.18 (d, J=14.5 Hz, 1H), 6.46 (d, J=8.7 Hz, 1H), 7.16–7.36 (m, 10H).

Example 19

The minor product from the reaction of Example 18, (2S,3S,5S)-2-[N-(benzyloxycarbonyl)amino])-5-[N-[[3-methyl-2R-(2-oxo-tetrahydropyrimidin-1-yl)]butyryl]amino]-3-hydroxy-7-methyl-1-phenyloctane (compound (33) of Table 1), was isolated and characterized as follows: TLC [$R_f$=0.74 (E)]; HPLC ($^r$ret=21.3 min.); MS m/z 589 (M+Na)$^+$; H NMR (CDCl$_3$) δ 0.81–0.90 (m, 12H, 1.17 (bs, 1H), 1.37 (bs, 1H), 1.52–1.58 (m, 3H), 1.81 (bs, 1H), ), 1.87 (bs, 1H), 2.28 (bs, 6H), 2.88 (d, J=6.7 Hz, 1H), 3.24 (m, 3H), 3.68 (bs, 1H), 3.82–3.86 (m, 2H), 4.28 (bs, 1H), 5.00 (d, J=12.4 Hz, 1H), ), 5.06 (d, J=12.4 Hz, 1H), ), 5.33 (d, J=11.8 Hz, 1H), 6.79 (bs, 1H), 7.17–7.34 (m, 10H).

Example 20

This example illustrates the synthesis of (2S,3S,5S)-2-[N-(3S-terahydrofuranyloxycarbonyl]amino]-5-[N-[[3-methyl-2S-(2-oxo-tetrahydropyrimidin-1-yl)]butyryl]amino]-3-hydroxy-7-methyl-1-phenyloctane (compound (35) of Table 1). The compound was prepared following a similar procedure described in Example 10, substituting 3S-terahydrofuranyl)-N-succinimidylcarbonate for (thiazol-5-yl-methyl)-N-succinimidylcarbonate: TLC [$R_f$=0.22 (D)]; HPLC ($^r$ret=16.77 min.); MS m/z 569 (M+Na)$^+$; H NMR (CDCl$_3$) δ 0.81 (d, J=6.5 Hz, 3H), 0.84 (d, J=6.4 Hz, 3H), 0.89 (d, J=6.5 Hz, 3H), 0.93 (d, J=6.4 Hz, 3H), 1.16–1.21 (m, 1H), 1.36–1.44 (m, 1H), 1.52–1.64 (m,3H), 1.83–1.85 (m, 1H), 1.92–1.99 (m, 2H), 2.08–2.16 (m, 1H), 2.29–2.31 (m, 1H), 2.80–2.91 (m, 2H), 3.27–3.29 (m, 2H), 3.37 (m, 1H), 3.68–3.70 (m, 2H), 3.78–3.91 (m, 6H), 4.22 (m, 1H), 5.12 (d, J=9.5 Hz, 1H), 5.15–5.18 (m, 1H), 5.49 (bs, 1H), 6.52 (m, 1H), 7.18–7.29 (m, 5H)

Example 21

This example illustrates the synthesis of (2S,3S,5S)-5-[N-(3-methyl-2S-(2-oxo-tetrahydropyrimidin-1-yl)]butyryl]amino]-2-[N-(morpholino-4-carbonyl]amino]-3-hydroxy-7-methyl-1-phenyloctane (compound (36) of Table 1). The compound was prepared following a similar procedure to that described in Example 12, except that (2S,3S,5S)-5-[N-(3-methyl-2S-(2-oxo-tetrahydropyrimidin-1-yl)]butyryl]amino]-2-amino-3-hydroxy-7-methyl-1-phenyloctane was used as the amine component: TLC[$R_f$=0.21 (E)]; HPLC ($t_{ret}$=16.5 min.); MS m/z 568 (M+Na)$^+$; H NMR (CDCl$_3$) δ 0.80 (d, J=6.5 Hz, 3H), 0.83 (d, J=6.6 Hz, 3H), 0.89 (d, J=6.4 Hz, 3H), 0.94 (d, J=6.4 Hz, 3H), 1.15–1.21 (m, 1H), 1.36–1.40 (m, 1H), 1.47–1.54 (m, 1H), 1.56–1.62 (m, 2H), 1.80–1.86 (m, 1H), 1.89–1.96 (m, 2H), 2.26–2.32 (m, 1H), 2.85–2.97 (m, 2H), 3.25–3.27 (m, 8H), 3.61–3.63 (m, 4H), 3.67–3.70 (m, 1H), 3.77–3.84 (m, 1H), 3.89–3.94 (m, 1H), 4.28 (d, J=11.1 Hz, 1H), 4.48 (d, J=4.0 Hz, 1H) , 4.70 (s, 1H1), 4.88 (d, J=8.5 Hz, 1H), 6.49 (bs, 1H), 7.18–7.29 (m, 6H).

Example 22

This example illustrates the synthesis of (2S,3S,5S)-2-[N-(3-hydroxy-2-methylbenzoyl)amino]-5-[N-[[3-methyl-2S-(2-oxo-tetrahydropyrimidin-1-yl)]butyryl]amino]-3-hydroxy-7-methyl-1-phenyloctane (compound (37) of Table 1). The compound was prepared following a similar procedure described in Example 8, except that 3-hydroxy-2-methylbenzoic acid was used as the acid component: TLC [$R_f$=0.45 (E)]; HPLC ($^r$ret=17.2 min.); MS m/z 589 (M+Na)$^+$; H NMR (CD$_3$OD) δ 0.88–0.94 (m, 12H),), 1.25–1.1 (m, 1H), 1.34–1.44 (m, 2H), 1.58–1.72 (m, 3H), 1.80–1.90 (m, 2H), 1.92 (s, 3H), 2.22–2.29 (m, 1H), 2.89–2.92 (m, 2H), 3.20–3.24 (m, 3H), 3.41–3.45 (m, 1H), 3.76 (dt, J=6.9; 1.7Hz, 1H), 4.26 (m, 1H), 4.34 (d, J=11.2 Hz, 1H), 4.55–4.60 (m, 1H), 6.50–6.52 (m, 1H), 6.74–6.76 (m, 1H), 6.92–6.95 (m, 1H), 7.17–7.34 (m, 5H), 7.56 (d, J=9.2 Hz, 1H), 7.67 (d, J=9.5 Hz).

Example 23

This example illustrates the synthesis of (2S, 3S, 5S)-5-[N-[2-(2,6-dimethylphenoxy)acetyl]amino]-2-[N-[[3-methyl-2S-(2-oxo-tetrahydropyrimidin-1-yl)butyryl]amino]-3-hydroxy-7-methyl-1-phenyloctane (compound (43) of Table 1). The compound was prepared from compound 15 of FIG. 5 and compound 14 of FIG. 4 following a procedure similar to that described in Example 10: HPLC ($^r$ret=23.6 min.); MS m/z 617 (M+Na)$^+$; H NMR (CD$_3$OD) δ 0.82 (d, J=6.6 Hz, 3H), 0.90 (d, J=6.5 Hz, 3H), 0.94 (d, J=6.7 Hz, 3H), 0.96 (d, J=6.7 Hz, 3H), 1.25–1.30 (m, 1H), 1.43–1.49 (m, 1H), 1.52–1.58 (m, 1H), 1.52–1.58 (m, 1H), 1.61–1.72 (m, 4H), 2.06–2.15 (m, 1H), 2.20 (m, 6H), 2.60–2.65 (m, 1H), 2.76–2.87 (m, 2H), 2.96–3.01 (m 1H), 3.10–3.14 (m, 2H), 3.73–3.74 (m, 1H), 4.19–4.26 (m, 1H), 4.29 (d, J=11.2 Hz, 1H), 4.34–4.38 (m, 1H), 4.41–4.46 (m, 1H), 6.92–6.95 (m, 1H), 7.02 (d, J=7.6 Hz, 2H), 7.13–7.16 (m, 1H), 7.21–7.27 (m 4H) , 7.38 (d, J=8.7 Hz, 1H) , 7.94 (d, J=9.4 Hz, 1H)

Example 24

This example illustrates the synthesis of (2S,3S,5S)-2-[N-(benzyloxycarbonyl)amino]-5-[N-[2-(2,6-dimethylphenoxy)acetyl]amino]-3-hydroxy-7-methyl-1-phenyloctane (compound (40) of FIG. 7). The compound was prepared from compound (17) of FIG. 7 following a procedure similar to that described in Example 9: Yield (84%); TLC [$R_f$0.68 (C)]; HPLC ($t_{ret}$=24.8 min.); MS m/z 569 (M+Na)$^+$; H NMR (CDCl$_3$) δ 0.89 (dd, J=6.6; 6.5 Hz, 6H), 1.19–1.24 (m, 1H), 1.42–1.48 (m, 1H), 1.59–1.67 (m, 3H), 2.20 (s, 6H), 2.78–2.90 (m, 2H), 3.65–3.67 (m, 1H), 4.05–4.07 (m, 1H), 4.13–4.15 (m, 2H), 4.26–4.32 (m, 1H, 4.95–5.04 (m, 1H), 6.91–6.94 (m, 1H), 7.00 (d, J=7.4 Hz, 2H), 7.12–7.14 (m, 1H), 7.21–7.31 (m, 1OH).

Example 25

This example illustrates the synthesis of (2S,3S,5S)-5-[N-[2-(2,6-dimethylphenoxy)acetyl]amino]-2-[N-(3S-terahydrofuranyloxycarbonyl)amino]-3-hydroxy-7-methyl-1-phenyloctane (compound 41 of Table 1). Compound (60) was prepared by subjecting compound (40) to hydrogenolysis in accordance with Example 16 (see FIG. 7). Compound (60) was then reacted with 3S-terahydrofuranyl-N-succinimidylcarbonate following a procedure similar to that described in Example 11: TLC [$R_f$=0.26 (D)]; HPLC ($^r$ret= 22.3 min.); MS m/z 549 (M+Na)$^+$; H NMR (CD$_3$OD) δ 0.92–0.94 (m, 6H),), 1.26–1.32 (m, 1H), 1.47–1.53 (m, 1H), 1.63–1.69 (m, 4H), 1.93–1.98 (m, 1H), 2.08–2.23 (m, 1H), 2.22 (m, 6H), 2.76–2.88 (m, 3H), 3.56 (d, J=10.4 Hz, 1H), 3.66–3.70 (m, 2H), 3.73–3.80 (m, 2H), 3.82–3.87 (m, 1H), 3.99–4.04 (m, 1H), 4.16 (bs, 2H), 4.30 (m, 1H), 5.05–5.07 (m, 1H), 6.54 (d, J=9.6 Hz, 1H), 6.91–6.94 (m, 1H), 7.01 (d, J=7.5Hz, 2H), 7.12–7.16 (m, 1H) , 7.22–7.27 (m, 5H) , 7.85 (d, J=9.3 Hz, 1H)

Example 26

This example illustrates the synthesis of (2S,3S,5S)-5-[N-[2-(2,6-dimethylphenoxy)acetyl]amino]-2-[N-(3-hydroxy-2-methylbenzoyl)amino]-3-hydroxy-7-methyl-1-phenyloctane (compound 42 of Table 1). Compound (60) was prepared by subjecting compound (40) to hydrogenolysis in accordance with Example 16 (See FIG. 7). Compound (60) was then reacted with 3-hydroxy-2-methylbenzoic acid following a procedure similar to that described in Example 8: HPLC ($^t$ret=21.9 min.); MS m/z 569 (M+Na)$^+$; H NMR (CD$_3$OD/DMSO-d$_6$) δ 0.95 (dd, J=8.7; 6.6 Hz, 6H), 1.30–1.35 (m, 1H), 1.52–1.58 (m, 1H), 1.66–1.72 (m, 1H), 1.74–1.78 (m, 2H), 1.98 (s, 3H), 2.24 (m, 6H), 2.88–2.98 (m, 2H), 3.53–3.78 (m, 1H), 4.179–4.23 (m, 1H), 4.36–4.42 (m, 1H), 4.52–4.56 (m, 1H), 6.00 (dd, J=7.6; 0.9 Hz, 1H), 6.79 (d, J=8.07; 0.86 Hz, 1H), 6.92–7.03 (m, 4H), 7.17–7.20 (m, 1H), 7.26–7.29 (m, 2H), 7.32–7.34 (m, 2H).

Example 27

This example illustrates the synthesis of (2S,3S,5S)-2-[N-[2-(2,6-dimethylphenoxy)acetyl]amino]-5-[N-[[N'-(morpholin-4)carbonyl]valinyl]amino]-3-hydroxy-7-methyl-1-phenyloctane (compound (45) of Table 1). The compound was prepared by following a procedure similar to that described in Example 9, except that N-[(morpholin-4)carbonyl]valine was used as the acid component: HPLC ($t_{ret}$=23.4 min.); MS m/z 647 (M+Na)$^+$; H NMR (CDCl$_3$) δ 0.84–90 (m, 9H), 0. !(d, J=6.7 Hz, 3H), 1.22–1.29 (m, 4H), 1.39–1.44 (m, 1H) , 1.52–1.71 (m, 6H), 2.16 (m, 1H), 2.18 (s, 6H), 3.00–3.01 (m, 2H), 3.78 (m, 1H), 3.84–3.87 (m, 1H), 3.92–3.93 (m, 1H), 4.06–4.24 (m, 6H), 5.04 (bs, 1H), 5.95 (d, J=8.0 Hz, 1H), 6.93–7.01 (m, 3H), 7.20–7.24 (m, 2H), 7.27–7.31 (m, 3H).

Example 28

This example illustrates the synthesis of (2S,3S,5S)-2-[N-[2-(2,6-dimethylphenoxy)acetyl]amino]-5-[N-[[N'-ethyloxycarbonyl]valinyl]amino]-3-hydroxy-7-methyl-1-phenyloctane (compound (46) of Table 1). The compound was prepared by following a procedure similar to that described in Example 9, except that N-(ethoxycarbonyl)-valine was used as the acid component: HPLC ($t_{ret}$=23.6 min.); MS m/z 606 (M+Na)$^+$; H NMR (CDCl$_3$) δ 0.84 (d, J=6.4 Hz, 3H), 0.86 (d, J=6.7 Hz, 3H), 0.91 (d, J=6.9 Hz, 3H), 0.93 (d, J=6.9 Hz, 3H), 1.23–1.29 (m, 2H), 1.39–1.45 (m, 1H), 1.50–1.71 (m, 2H), 2.05–2.14 (m, 1H), 2.18 (s, 6H), 2.99–3.01 (m, 2H), 3.31–3.40 (m, 4H), 3.67–3.69 (m, 4H), 3.77 (m, 1H), 3.88–3.92 (m, 1H), 4.03 (m, 1H), 4.13–1.24 (m, 4H), 4.96 (d, J=7.9 Hz, 1H), 6.06 (d, J=7.7 Hz, 1H), 6.92–6.97 (m, 1H), 6.98–7.03 (m, 2H), 7.19–7.24 (m, 2H), 7.27–7.31 (m, 3H).

Example 29

This example illustrates the synthesis of (2S,3S,5S)-2-[N-[2-(2,6-dimethylphenoxy)acetyl]amino]-5-[N-[[N'-(methylsulfonyl)]valinyl]amino]-3-hydroxy-7-methyl-1-phenyloctane (compound (51) of Table 1). The compound was prepared by following a procedure similar to that described in Example 9, except that N-(methylsulfonyl) valine was used as the acid component: HPLC ($t_{ret}$=22.4 min.); MS m/z 613 (M+Na)$^+$; H NMR (CD$_3$OD) δ 0.89 (d, J=6.5 Hz, 3H), 0.90 (d, J=6.6Hz, 3H), 0.95 (d, J=6.8 Hz, 3H), 0.98 (d, J=6.6 Hz, 3H), 1.24–1.29 (m, 1H), 1.40–1.46 (m, 1H), 1.58–1.70 (m, 3H), 1.95–2.02 (m, 1H), 2.19 (s, 6H), 2.84 (s, 3H), 2.92–2.95 (m, 2H), 3.62 (d, J=6.3 Hz 1H), 3.79 (m, 1H), 4.05 (d, J=14.8 Hz, 1H), 4.14–1.18 (m, 1H), 4.17 (d, J=14.8 Hz, 1H), 4.41–4.44 (m, 1H), 6.91–6.94 (dd, J=6.8, 6.8 Hz, 1H), 6.99 (m, 2H), 7.17–7.20 (m, 1H), 7.25–7.32 (m, 4H).

Example 30

This example illustrates the synthesis of (2S,3S,5S)-2-[N-[2-(2,6-dimethylphenoxy)acetyl]amino]-5-[N-[[N'-(p-methoxyphenylcarbonyl)]valinyl]amino]-3-hydroxy-7-methyl-1-phenyloctane (compound (52) of Table 1). The compound was prepared by following a procedure similar to that described in Example 9, except that N'-(p-methoxyphenylcarbonyl)valine was used as the acid component: HPLC ($t_{ret}$=21.9 min.); MS m/z 646 (M+H)$^+$; H NMR (CD$_3$OD) δ 0.84 (d, J=6.6 Hz, 3H) , 0.86 (d, J=6.7 Hz, 3H), 0.97 (d, J=6.8 Hz, 3H), 0.99 (d, J=6.6 Hz, 3H), 1.22–1.28 (m, 1H), 1.38–1.45 (m, 1H), 1.58–1.70 (m, 3H), 2.10–2.16 (m, 1H), 2.19 (s, 6H), 2.94–2.95 (m, 2H), 3.79 (m, 1H), 3.84 (s, 3H), 4.06 (d, J=14.7 Hz, 1H), 4.14–1.18 (m, 1H), 4.17 (d, J=14.8 Hz, 1H), 4.27 (d, J=14.8 Hz, 1H), 4.44–4.47 (m, 1H), 6.91–6.94 (dd, J=6.7, 6.8 Hz, 1H), 6.97–7.01 (m, 4H), 7.17–7.20 (m, 1H), 7.25–7.32 (m, 4H) , 7.81 (m, 2H)

Example 31

This example illustrates the synthesis of (2S,3S,5S)-2-[N-[2-(2,6-dimethylphenoxy)acetyl]amino]-5-[N-[[N'-(p-methoxyphenylsulfonyl)]valinyl]amino-3-hydroxy-7-methyl-1-phenyloctane (compound 54) of Table 1). The compound was prepared by following a procedure similar to that described in Example 9, except that N-(p-methoxyphenylsulfonyl)valine was used as the acid component: Yield (49%); HPLC ($t_{ret}$=23.8 min.); MS m/z 704 (M+Na)$^+$; H NMR (CD$_3$OD) δ 0.75 (d, J=6.4 Hz, 3H), 0.79 (d, J=6.6 Hz, 3H), 0.82 (d, J=6.8 Hz, 3H), 0.87 (d, J=6.8 Hz, 3H), 1.07–1.18 (m, 2H), 1.21–1.28 (m, 1H), 1.53–1.56 (bt, 2H), 1.84–1.92 (m, 1H), 2.18 (s, 6H), 2.89–2.91 (m, 2H), 3.46 (d, J=5.6 Hz 1H), 3.73 (bt, 1H), 3.85 (s, 3H), 3.91–3.96 (m, 1H), 4.04 (d, J=14.8 Hz, 1H), 4.16 (d, J=14.8 Hz, 1H), 4.37 (m, 1H), 6.92 (dd, J=6.7, 8.2 Hz, 1H), 6.99–7.03 (m, 4H), 7.16–7.19 (m, 1H), 7.24–7.30 (m, 4H), 7.76 (bt, J=2.8 Hz, 1H), 7.77 (bt, J=2.1 Hz, 1H).

Example 32

This example illustrates the synthesis of (2S,3S,5S)-2-[N-(2,6-dimethylphenoxy)acetyl]amino]-5-[N-(isovaleryl)amino]-3-hydroxy-7-methyl-1-phenyloctane (compound (55) of Table 1). The compound was prepared following a procedure similar to that described in Example 10, except that isovaleryl-N-succinimidylcarbonate was used in place of (thiazol-5-yl-methyl)-N-succinimidylcarbonate: TLC

[R$_f$0.41 (C)]; HPLC (t$_{ret}$=24.0 min.); MS m/z 519 (M+Na)$^+$; H NMR (CDCl$_3$) δ 0.89 (d, J=6.6 Hz, 6H), 0.92 (d, J=6.4 Hz, 6H), 1.19–1.24 (m, 1H), 2.01–2.08 (m, 1H), 1.34–1.40 (m, 1H), 1.57–1.64 (m, 3H), 1.97–1.99 (m, 2H), 2.01–2.08 (m, 1H), 2.19 (s, 6H), 2.92–2.94 (m, 2H), 3.74 (dt, J=6.8 Hz, 1H), 4.07 (d, J=14.8 Hz, 1H), 4.10–4.16(m, 1H), 4.19 (d, J=14.9 Hz, 1H), 4.33–4.46 (m, 1H), 6.93 (dd, 6.8 Hz, 1H), 6.99–7.01 (bc, 2H), 7.16–7.19 (m, 1H), 7.25–7.31 (m, 4H).

Example 33

This example illustrates the synthesis of (2S,3S,5S) -5-[N-[N'-(benzyloxycarbonyl)alaninyl]amino] -2-[N-[2-(2,6-dimethylphenoxy)acetyl]amino]-3-hydroxy-7-methyl-1-phenyloctane (compound (56) of Table 1). The compound was prepared following a similar procedure described in Example 9, except that N-(benzyloxycarbonyl)alanine was used as the acid component: TLC [R$_f$=0.46 (A)]; HPLC (t$_{ret}$=25.5 min.); MS m/z 606 (M+H)$^+$; H NMR δ 0.87 (bd, 6H) , 1.29–1.23 (m, 2H) g 1.25 (d, J=7.1 Hz, 3H), 1.33–1.42 (m, 1H), 1.61 (bt, 3H), 2.19 (s, 6H), 2.88–2.97 (m, 2H), 3.75 (bt, 1H), 4.05 (m, 1H), 4.06 (d, J=14.8 Hz, 1H), 4.12 (m, 1H), 4.20 (d, J=14.8 Hz, 1H), 4.44 (m, 1H), 5.08 (s, 2H), 6.93 (dd, J=6.8, 8.1 Hz, 1H), 6.99–7.01 (m, 2H), 7.16–7.19 (bdt, 1H), 7.24–7.36 (m, 9H).

Example 34

This example illustrates the synthesis of (2S,3S,5S)-2-[N-[2-(2,6-dimethylphenoxy)acetyl]amino]-5-[N-[(thiazol-5-yl-methoxy)carbonyl]amino]-3-hydroxy-7-methyl-1-phenyloctane (compound (57) of Table 1). The compound (2S,3S,5S)-5-[N-tert-butyloxycarbonylamino]-2-[N-[2-(2,6-dimethylphenoxy)acetyl]amino]-3-hydroxy-7-methyl-1-phenyloctane (compound (15) of Table 1) was treated with trifluoroacetic acid to remove the N-tert-butyloxycarbonyl group in accordance with Example 9, to provide the amine (2S,3S,5S)-5-amino-2-[N-[2-(2,6-dimethylphenoxy)acetyl] amino]-3-hydroxy-7-methyl-1-phenyloctane. The desired product was obtained by treating the amine with (thiazol-5-yl-methyl)-N-succinimidylcarbonate following a procedure similar to that described in Example 10: TLC [R$_f$=0.58 (A)]; HPLC (t$_{ret}$=22.2 min.); MS m/z 576 (M+Na)$^+$; H NMR (CD$_3$OD) δ 0.87 (d, J=6.6, 3H), 0.89 (d, J=6.5, 3H), 1.16–1.22 (m, 1H), 1.31–1.37 (m, 1H), 1.60 (bt, 3H), 2.18 (s, 6H), 2.90–2.92 (m, 2H), 3.75 (bt, 1H), 3.85 (s, 3H) 3.83–3.89 (m, 1H), 4.09 (d, J=15.7 Hz, 1H), 4.19 (d, J=15.8 Hz, 1H), 4.48 (bt, 1H), 5.26 (S, 2H), 6.92 (dd, J=8.2 Hz, 1H), 6.99–7.01 (m, 3H), 7.16–7.19 (m, 1H), 7.24–7.31 (m, 4H), 7.88 (s, 1H), 8.96 (s, 1H).

Aspartic Protease Activity

Example 35

This example illustrates the HIV-1 protease inhibition activity (K$_i$), HIV-1 antiviral data (EC$_{50}$), and the toxicity against normal cells (IC$_{50}$), for particular compounds of formula (I). The HIV protease assay was done according to the protocol described in Kageyama et al, *Antimicrob. Agents Chemother.*, 37, 272 (1993). The HIV antiviral assay was done according to the protocol described in Weislow et al., *J. National Cancer Inst.* 81, 577 (1989). The results are shown in Table 1, below.

In Tables 1–3, below, the compounds tested are of the formula:

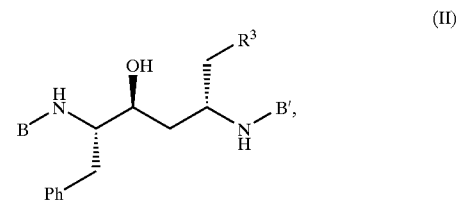

(II)

wherein R$^3$ is isopropyl, and the substituents B and B' are as indicated in the tables. The substituent "2-Py-Ant" is a substituent of the formula:

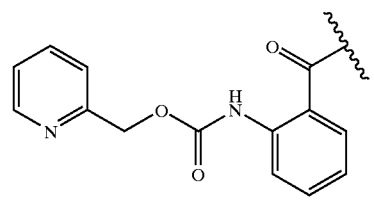

The substituent "2-Py-Val" is substituent of the formula:

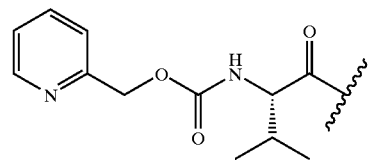

The term "Phe-Phe core" means that R$^3$ is phenyl in the compound of formula (II) , and that structural modification applies to all data listed in the same row for which the term appears. The term "CBZ" or "Z" means benzyloxycarbonyl. The term "Boc" means tert-butoxycarbonyl.

TABLE 1

| Comp. No. | B | B' | HIV-1 $K_i$ (pM) | 84V $K_i$ (pM) | 32I $K_i$ (pM) | 82F/84V $K_i$ (pM) | HIV-1 $EC_{50}$ (μM) | normal $IC_{50}$ (μM) |
|---|---|---|---|---|---|---|---|---|
| (20) | 2-Py-Ant carbamate-Val | 2-Py-Ant carbamate-Val | 5 | 23 | | 25 | 0.092 | >20 |
| (21) | 2-Py-Ant | t-Bu ester | 140 | 2.7 (nM) | | | 0.127 | >20 |
| (15) | 2,6-dimethylphenoxy-acetyl | 2-Py-Ant | 9 | | | | | |
| (16) | 2,6-dimethylphenoxy-acetyl | Val-cyclic urea | 7 | 91 | 31 | 137 | 0.023 | |
| (26) | 2,6-dimethylphenoxy-acetyl | tetrahydrofuranyl ester | 60 | | | 2.7 (nM) | 0.7 | |
| (27) | 2,6-dimethylphenoxy-acetyl | morpholine amide | 37 nM | | | | >50 | |

TABLE 1-continued

| Comp. No. | B | B' | HIV-1 $K_i$ (pM) | 84V $K_i$ (pM) | 32I $K_i$ (pM) | 82F/84V $K_i$ (pM) | HIV-1 $EC_{50}$ (μM) | normal $IC_{50}$ (μM) |
|---|---|---|---|---|---|---|---|---|
| (28) | 2,6-dimethylphenoxyacetyl | tert-butyl amide | 100 | | | | 2 | |
| (29) | 2,6-dimethylphenoxyacetyl | cyclic thiourea | 16 nM | | | | inactive | |
| (30) | 2,6-dimethylphenoxyacetyl | 2-Py-Val | 17 | | | 410 | | >100 |
| (31) | 2,6-dimethylphenoxyacetyl | 4-aminobenzoyl | 1.2 (nM) | | | | 0.083 | >100 |
| (32) | 2,6-dimethylphenoxyacetyl | 3-aminobenzoyl | 331 | | | | 2 | >100 |
| (33) | CBZ | Val-cyclic urea | 65% @ 1 (μM) 38% @ (0.5 μM) | | | | 2 | ≧100 |

TABLE 1-continued

| Comp. No. | B | B' | HIV-1 K$_i$ (pM) | 84V K$_i$ (pM) | 32I K$_i$ (pM) | 82F/84V K$_i$ (pM) | HIV-1 EC$_{50}$ (μM) | normal IC$_{50}$ (μM) |
|---|---|---|---|---|---|---|---|---|
| (18) | CBZ | [tetrahydrofuran-3-yl ester] | 65 ± 16 | | | | 0.6 | >100 |
| (35) | [tetrahydrofuran-3-yl ester] | [cyclic urea with iPr] | 94 ± 24 | | | 3.2 nM | 0.7 | >100 |
| (36) | [morpholine amide] | [cyclic urea with iPr] | 571 | | | | 2 | >100 |
| (37) | [3-hydroxy-2-methylbenzoyl] | [cyclic urea with iPr] | 104 ± 10 | | | | 0.2 | >10 |
| (38) | [2-methylbenzoyl] | [tert-butyl carbamate] | 2.1 nM | 12 nM | | | | |

TABLE 1-continued

| Comp. No. | B | B' | HIV-1 $K_i$ (pM) | 84V $K_i$ (pM) | 32I $K_i$ (pM) | 82F/84V $K_i$ (pM) | HIV-1 $EC_{50}$ (μM) | normal $IC_{50}$ (μM) |
|---|---|---|---|---|---|---|---|---|
| (19) | thiazol-5-ylmethyl carbamate | valine-tetrahydropyrimidin-2-one amide | 70 ± 10 | | | | 0.5 | >100 |
| (40) | CBZ | 2,6-dimethylphenoxyacetyl | 197 | | | | inactive | |
| (41) | (S)-tetrahydrofuran-3-yl carbamate | 2,6-dimethylphenoxyacetyl | 222 | | | | >1 | >100 |
| (42) | 3-hydroxy-2-methylbenzoyl | 2,6-dimethylphenoxyacetyl | 311 | | | | 0.75 | >100 |
| (43) | valine-tetrahydropyrimidin-2-one amide | 2,6-dimethylphenoxyacetyl | 176 | | | | 0.54 | >100 |
| (44) | valine-tetrahydropyrimidin-2-one amide | tert-butyl carbamate | 1,493 | | | | inactive | |

TABLE 1-continued

| Comp. No. | B | B' | HIV-1 K$_i$ (pM) 84V K$_i$ (pM) | 32I K$_i$ (pM) | 82F/84V K$_i$ (pM) | HIV-1 EC$_{50}$ (μM) | normal IC$_{50}$ (μM) |
|---|---|---|---|---|---|---|---|
| (45) | 2,6-dimethylphenoxy-acetyl | morpholine urea-Val | 50 | | 437 | 0.17 | >100 |
| (46) | 2,6-dimethylphenoxy-acetyl | ethyl carbamate-Val | 54 | | 671 | 0.16 | >100 |
| (47) | 2,6-dimethylphenoxy-acetyl | N-Cbz-piperidine-3-carbonyl | 1502 ± 66 | | | | |
| (48) | 2,6-dimethylphenoxy-acetyl | N-Cbz-piperidine-4-carbonyl | 113 nM | | | | |
| (49) | 2,6-dimethylphenoxy-acetyl | Val-NH$_2$ | 4 nM | | | 8 | >100 |
| (50) | 2,6-dimethylphenoxy-acetyl | N-acetyl-Val | 14 | | | 0.3 | >100 |

TABLE 1-continued

| Comp. No. | B | B' | HIV-1 $K_i$ (pM) | 84V $K_i$ (pM) | 32I $K_i$ (pM) | 82F/84V $K_i$ (pM) | HIV-1 $EC_{50}$ (μM) | normal $IC_{50}$ (μM) |
|---|---|---|---|---|---|---|---|---|
| (51) | 2,6-dimethylphenoxy-acetyl | N-methylsulfonyl-Val | 34 | | | | 0.7 | >100 |
| (52) | 2,6-dimethylphenoxy-acetyl | 4-methoxybenzamido-Val | 30 | | | | 0.2 | >93 |
| (54) | 2,6-dimethylphenoxy-acetyl | 4-methoxybenzenesulfonamido-Val | 6.8 | | | | 0.2 | 84 |
| (55) | 2,6-dimethylphenoxy-acetyl | isobutyl ketone | 1.5 nM | | | | 10 | >100 |
| (56) | 2,6-dimethylphenoxy-acetyl | Cbz-Ala | 195 | | | | 1 | >100 |
| (57) | 2,6-dimethylphenoxy-acetyl | thiazol-5-ylmethoxycarbonyl-Ala ester | 94 | | | | 1 | 10 |

TABLE 1-continued

| Comp. No. | B | B' | HIV-1 $K_i$ (pM) | 84V $K_i$ (pM) | 32I $K_i$ (pM) | 82F/84V $K_i$ (pM) | HIV-1 $EC_{50}$ (μM) | normal $IC_{50}$ (μM) |
|---|---|---|---|---|---|---|---|---|
| (58) | 2,6-dimethylphenoxy-acetyl | 3-hydroxyphenyl ketone | 1.2 nM | | | | 2 | 10 |
| (59) | Z-Gly | 3-hydroxyphenyl ketone | 108 nM | | | | >10 | |
| (60) | Z-Val | 3-hydroxyphenyl ketone | 198 | | | | 0.91 | >10 |
| (61) | Z-Ala | 3-hydroxyphenyl ketone | 2 nM | | | | >10 | |
| (62) | Z-Ile | 3-hydroxyphenyl ketone | 157 | | | | 1.4 | >10 |
| (63) | 2,6-dimethylphenoxy-acetyl | valyl-pyrrolidinone | 8.3 ± 4 | | | | 0.0004 | 10 |

TABLE 1-continued

| Comp. No. | B | B' | HIV-1 K_i (pM) | 84V K_i (pM) | 32I K_i (pM) | 82F/84V K_i (pM) | HIV-1 EC$_{50}$ ($\mu$M) | normal IC$_{50}$ ($\mu$M) |
|---|---|---|---|---|---|---|---|---|
| (64) | 2,6-dimethylphenoxyacetyl | N-benzyl-4-methoxybenzenesulfonamide with isopropyl | 4.1 | | | | 0.05 | >10 |
| (65) | 2,6-dimethylphenoxyacetyl | quinoline-2-carboxamide with CONH$_2$ | 38.2 | | | | | |
| (66) | 2,6-dimethylphenoxyacetyl | quinoline-2-carboxamide with CN | 2.4 nM | | | | | |
| (67) | Z-Phe | 3-hydroxybenzoyl | | | | not active | | |
| (68) | 2,6-dimethylphenoxyacetyl | N-methyl tetrahydropyrimidinone with isopropyl | | | | 0.50–0.11 | 5 | |

This example demonstrates that the compounds of the present invention exhibit excellent potency against HIV-1 and certain mutant strains of HIV-1, such as 84V, 32I, and double mutants such as 82F/84V, for example, as demonstrated with compound (16) of Table 1. These results are illustrative of the broad spectrum activity which can be expected from other compounds of the present invention. Moreover, the compounds were not toxic to normal cells, as indicated by the relatively high $IC_{50}$'s.

Example 36

This example illustrates the HIV-1 protease inhibition activity, HIV-1 antiviral data, plasmepsin II inhibition activity, and cathepsin D inhibition activity, for particular compounds of formula (I). The definition of the general formula, and for the substituents indicated in the tables that follow, apply the same in this example as they did in Example 35.

The HIV protease assay was done according to the protocol described in Example 35. The plasmepsin II assay was done according to the protocol used in Silva et al., *Proc. Nat. Acad. Sci. USA*, 93, pp. 10034–10039, September 1996 (Biochemstry). The cathepsin D assay was done according to the protocol described in Gulnik et al., *FEBS Letters*, 413, 379–384 (1997). The results are shown in Table 2, below. The compounds illustrated in Table 2 are of the general formula (II), as described in Example 35.

TABLE 2

| Comp. No. | B | B' | $R^3$ | HIV-1 $K_i$ (nM) | Cath D $K_i$ (nM) | Pls II $K_i$ (nM) | HIV-1 $EC_{50}$ ($\mu$M) | normal $IC_{50}$ ($\mu$M) |
|---|---|---|---|---|---|---|---|---|
| (24) | | | | 0.012 | 1,960 | 3,500 | 0.041 | >100 |
| (16) | | | | 0.007 | 3,300 | 357 | 0.023 | >100 |
| (26) | | | | 0.060 | 3.5 | 55 | 0.7 | >100 |
| (28) | | | | 0.1 | — | 107 | 2 | >100 |
| (31) | | | | 1.2 | — | 30 | 2 | >100 |
| (32) | | | | 0.33 | 7.4 | 18 | 2 | >100 |

TABLE 2-continued

| Comp. No. | B | B' | R³ | HIV-1 K$_i$ (nM) | Cath D K$_i$ (nM) | Pls II K$_i$ (nM) | HIV-1 EC$_{50}$ (μM) | normal IC$_{50}$ (μM) |
|---|---|---|---|---|---|---|---|---|
| (15) | 2,6-dimethylphenoxy-acetyl | tert-butyl carbamate | isobutyl | 0.009 | 6.1 | 210 | — | — |
| (27) | 2,6-dimethylphenoxy-acetyl | morpholine amide | isobutyl | 0.37 | 6.1 | 76 | >50 | — |
| (29) | 2,6-dimethylphenoxy-acetyl | cyclic urea | isobutyl | 0.16 | 305 | 3,500 | not active | — |
| (30) | 2,6-dimethylphenoxy-acetyl | 2-Py-Val | isobutyl | 0.017 | 3,300 | 2,350 | 0.083 | >100 |
| (60) | Z-Val | 3-hydroxyphenyl ketone | isobutyl | 0.198 | — | 2.4 | — | — |
| (62) | Z-Ile | 3-hydroxyphenyl ketone | isobutyl | 0.157 | — | 1.2 | — | — |
| (67) | Z-Phe | 3-hydroxyphenyl ketone | isobutyl | — | — | 17 | — | — |

A comparison between compounds (24) and (16) demonstrates, for example, that changing the substituent at R³ from an aryl to an alkyl in accordance with the present invention, results in a significant increase in aspartic protease inhibitory activity. For example, compound (16) is about ten-fold more potent than compound (24) against HIV-1 protease and plasmepsin II. Compounds (28), (31), and (32) demonstrated generally potent aspartic protease inhibitory activity against HIV-1, cathepsin D, and plasmepsin II. The compounds were generally potent in the antiviral assay, as illustrated by the EC$_{50}$'s, and were not toxic to normal cells, as illustrated by the IC$_{50}$'s.

In Vivo Data

Example 37

This example demonstrates the oral bioavailability of compound (19) of Table 1. Compound (19) was tested in IV-PO crossover studies in two Sprague-Dawley rats. For the IV portion of the studies, compound (19) was given at doses of 7 and 3 mg/kg, as a short infusion (30–60 seconds) via a jugular vein catheter using a vehicle of DMSO and a dose volume of 1 ml/kg. Heparinized blood samples were collected at close intervals through 3 hours, the plasma was separated, and plasma concentrations of compound (19) were determined by HPLC. One to two weeks later, the same rats were given doses of 22 and 50 mg/kg by gastric intubation. The vehicle was PEC300 and the dose volume was 10 ml/kg. Blood samples were collected at regular intervals through 24 hours, and analyzed as above. The oral bioavailability in both of these studies was 100%. Based on the excellent oral bioavailability of compound (19), it is expected that compound (19) will be an effective inhibitor of systemic aspartic protease when administered orally. Other compounds of the present invention also are expected to have good oral bioavailability.

Example 38

This example illustrates the oral bioavailability of various compounds of the present invention. The compounds tested in this example were administered intravenously (IV) and orally (P.O.) in rats. In the IV experiment, compounds were administered at a dose of about 5 mg/kg (infusion duration about 0.5–1.5 min.) and the rate of drug clearance (CL) and the time at which one-half of the drug was eliminated ($t_{1/2}$) were determined. In the P.O. experiment, compounds were administered at a dose of about 37 mg/kg (PEG 300 vehicle) and the maximum observed drug concentration ($C_{max}$), the time after oral administration at which the maximum drug concentration was observed ($t_{max}$), and the oral bioavailability (%F) were determined. Drug concentrations were measured by centrifuging plasma samples, extracting the supernatants with tert-butyl methyl ether, and analyzing the extracts by HFLC. Oral bioavailability (%F) was calculated on the basis of the ratio of the amount of drug absorbed systemically from oral administration ($AUC_{p.o.}$) relative to the amount of systemic drug obtained from intravenous administration ($AUC_{i.v.}$) The results are shown below in Table 3.

TABLE 3

| Comp. No. | B | B' | HIV-1 $K_i$ (pM) | HIV-2 $EC_{50}$ ($\mu$M) | RatIV $t_{1/2}$ (min.) | RatIV CL (ml/min./kg) | Rat P.O. $C_{max}$ (nM) | Rat P.O. $t_{max}$ (min.) | Rat P.O. % F (%) |
|---|---|---|---|---|---|---|---|---|---|
| (16) | 2,6-dimethylphenoxy-CH2-C(O)- | cyclic urea-CH(iPr)-C(O)- | 8 | 0.023 | 27 | 9.8 | 269 | 10–15 | 1 |
| (43) | cyclic urea-CH(iPr)-C(O)- | 2,6-dimethylphenoxy-CH2-C(O)- | 176 | 0.54 | 28 | 36.6 | 2100 | 120 | 42 |
| (19) | thiazol-5-yl-CH2-O-C(O)- | cyclic urea-CH(iPr)-C(O)- | 70 | 0.5 | 18 | 25 | 24.800 | 120–360 | 100 |
| (45) | 2,6-dimethylphenoxy-CH2-C(O)- | morpholine-C(O)-NH-CH(iPr)-C(O)- | 50 | 0.17 | 20 | 67.5 | 573 | 16 | 29 |

The foregoing data provides examples of compounds of the present invention that exhibit good oral bioavailability. For example, compounds 43 and 19 in Table 3 exhibited oral bioavailabilities of 42% and 100%, respectively, and each compound exhibited micromolar $C_{max}$ concentrations when administered orally. The compounds of the present invention also are expected to exhibit good oral bioavailability in humans.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of the formula:

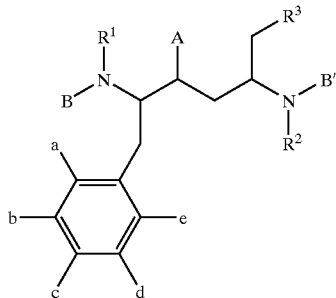

(I)

wherein:

a, b, c, d, and e, are the same or different and each is H, $R^7$, $OR^7$, $SR^7$, $NR^7R^8$, $NHCOR^7$, $CO_2R^7$, CN, $NO_2$, $NH_2$, $N_3$, or a halogen, wherein $R^7$ and $R^8$ are the same or different and each is H, an unsubstituted $C_1$–$C_{20}$ alkyl, or a substituted $C_1$–$C_{20}$ alkyl;

$R^1$ and $R^2$ are the same or different and each is H or a $C_1$–$C_{20}$ alkyl, wherein $R^1$ and $R^2$ are unsubstituted or substituted;

$R^3$ is isopropyl, wherein $R^3$ is unsubstituted or substituted;

A is OH, $NH_2$, or SH;

B and B' are the same or different and each is of the formula:

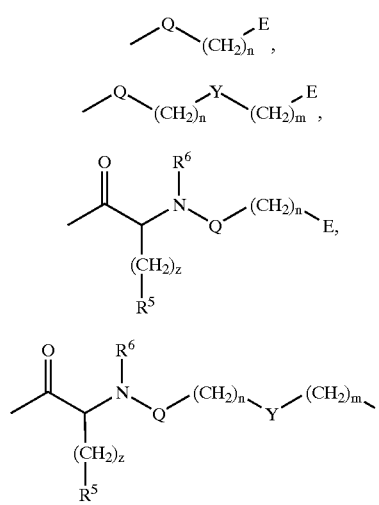

(Ia)
(Ib)
(Ic)
(Id)
(Ie)

or

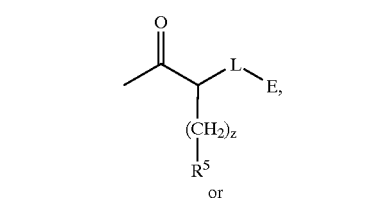

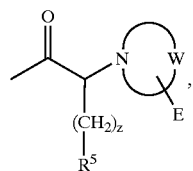

(If)

wherein:

m, n, and z, are the same or different and each is an integer from 0 to 4;

Q is $SO_2$ or C=(X), wherein X is O, $NR^7$, $NCO_2R^7$, $NSO_2R^7$, or S;

Y is O, S, $NR^4$, a $C_6$–$C_{15}$ aryl, or a heteroaryl having 6 atoms, at least two of which are heteroatoms, in the ring skeleton thereof, wherein $R^4$ is H, a $C_1$–$C_{20}$ an alkyl, a $C_2$–$C_{20}$ alkenyl, a $C_2$–$C_{20}$ alkynyl, a cycloalkyl having from 3 to about 10 carbon atoms in the carbocyclic skeleton thereof, a heterocycloalkyl having 6 atoms, at least two of which are heteroatoms, in the ring skeleton thereof, a phenyl, a naphthyl, or a heteroaryl having 6 atoms, at least two of which are heteroatoms, in the ring skeleton thereof, wherein $R^4$ is unsubstituted or substituted, and, when Y is an aryl or a heteroaryl, it is unsubstituted or substituted;

$R^5$ is H, a $C_1$–$C_{20}$ alkyl, a $C_2$–$C_{20}$ alkenyl, $C_2$–$C_{20}$ alkynyl, a cycloalkyl having from 3 to about 10 carbon atoms in the carbocyclic skeleton thereof, a heterocycloalkyl having 6 atoms, at least two of which are heteroatoms, in the ring skeleton thereof, a phenyl, a naphthyl, or a heteroaryl having 6 atoms, at least two of which are heteroatoms, in the ring skeleton thereof, wherein $R^5$ is unsubstituted or substituted;

L is O, S, or NH;

$R^6$ is H, a $C_1$–$C_{20}$ alkyl, a $C_2$–$C_{20}$ alkenyl, a $C_2$–$C_{20}$ alkynyl, a cycloalkyl having from 3 to about 10 carbon atoms in the carbocyclic skeleton thereof, a heterocycloalkyl having 6 atoms, at least two of which are heteroatoms, in the ring skeleton thereof, a phenyl, a naphthyl, or a heteroaryl having 6 atoms, at least two of which are heteroatoms, in the ring skeleton thereof, wherein $R^6$ is unsubstituted or substituted; and W of formula (If) is an organic residue comprising at least one carbon atom and at least one heteroatom, wherein W shares at least two bonds with the nitrogen atom bonded thereto such that the substituent:

of formula (If) defines a heterocycle, having 6 atoms, at least two of which are heteroatoms, in the ring skeleton thereof, which is unsubstituted or substituted; and E is H, $(CH_2)_qR^9$, $O(CH_2)_qR^9$, $S(CH_2)_qR^9$, $N[(CH_2)_qR^9]R^{10}$, $CO(CH_2)_qR^9$, $CS(CH_2)_qR^9$, $CO_2(CH_2)_qR^9$, $NHCO_2(CH_2)_qR^9$, $C(O)S(CH_2)_qR^9$, $C(S)O(CH_2)_qR^9$, $CS_2(CH_2)_qR^9$, $C(O)N[(CH_2)_qR^9]R^{10}$, $NHC(O)N[(CH_2)_qR^9]R^{10}$, $C(S)N[(CH_2)_qR^9]R^{10}$, $NHC(S)N[(CH_2)_qR^9]R^{10}$, $NR^{10}CO(CH_2)_qR^9$, $NR^{10}CS(CH_2)_qR^9$, $NR^{10}CO_2$ $(CH_2)_qR^9$, $NR^{10}C(O)S(CH_2)_qR^9$, $NR^{10}$ $CS_2(CH_2)_qR^9$, $O_2C(CH_2)_qR^9$, $S_2C(CH_2)_qR^9$, SCO $(CH_2)_qR^9$, $OCS(CH_2)_qR^9$, $SO_2(CH_2)_qR^9$, $OSO_2$ $(CH_2)_qR^9$, $NR^{10}SO_2(CH_2)_qR^9$, CN, $NO_2$, $N_3$, or a halogen, wherein:

q is an integer from 0–4;

$R^9$ is a $C_1$–$C_{20}$ alkyl, a $C_2$–$C_{20}$ alkenyl, a $C_2$–$C_{20}$ alkynyl, a cycloalkyl having from 3 to about 10 carbon atoms in the carbocyclic skeleton thereof, a heterocycloalkyl having 6 atoms, at least two of which are heteroatoms, in the ring skeleton thereof, a phenyl, a naphthyl, or a heteroaryl having 6 atoms, at least two of which are heteroatoms, in the ring skeleton thereof, wherein $R^9$ is unsubstituted or substituted; and $R^{10}$ is H, an unsubstituted $C_1$–$C_{20}$ alkyl, or a substituted $C_1$–$C_{20}$ alkyl; or B and $R^1$ together with the nitrogen atom to which they are bonded, and/or B' and $R^2$ together with the nitrogen atom to which they are bonded, comprise a heterocycle, having 6 atoms in the ring skeleton thereof, of the formula:

wherein W and E are as defined herein and said heterocycle is unsubstituted or substituted, wherein:

when $R^1$, $R^2$ and/or $R^4$ is substituted, each is substituted with one or more substituents selected from the group consisting of $R^7$, $OR^7$ $SR^7$, $NR^7R^8$, CN, $NO_2$, $N_3$, and halogens;

when $R^3$ is substituted, it is substituted with one or more substituents selected from the group consisting of $OR^7$, $SR^7$, CN, $NR^7R^8$, $NO_2$, $N_3$, and halogens;

when Y and/or $R^5$ is substituted, it is substituted with one or more substituents selected from the group consisting of, $R^7$, $OR^7$, $SR^7$, $NR^7R^8$, $COR^7$, $CSR^7$, $CO_2R^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, a guanidyl, CN, $NO_2$, $N_3$, and halogens;

when $R^6$ is substituted, it is substituted with one or more substituents selected from the group consisting of $R^7$, $OR^7$, $SR^7$, $CO_2R^7$, $SO_2R^7$, $NR^7R^8$, CN, $NO_2$, $N_3$, a cycloalkyl having from 3 to about 10 carbon atoms in the carbocyclic skeleton thereof, a heterocycloalkyl having 6 atoms, at least two of which are heteroatoms, in the ring skeleton thereof, a phenyl, a naphthyl, or a heteroaryl having 6 atoms, at least two of which are heteroatoms, in the ring skeleton thereof, and halogens;

when W of formula (If), the heterocycle defined by B and $R^1$ together with the nitrogen atom to which they are bonded, and/or the heterocycle defined by B' and $R^2$ together with the nitrogen atom to which they are bonded, are substituted, each is substituted with one or more substituents selected from the group consisting of oxo, thio, $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)$ $NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, CN, $NO_2$, $N_3$, and halogens, when $R^1$ and/or $R^8$ are substituted, each is substituted with one or more halogen atoms;

when $R^9$ is substituted, it is substituted with one or more substituents selected from the group consisting of $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)$ $NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, a guanidyl, oxo, thio, CN, $NO_2$, $N_3$, and halogens; and when $R^{10}$ is substituted, it is substituted with one or more substituents selected from the group consisting of CN, $NH_2$, $NO_2$, $N_3$, and halogens;

or a pharmacologically acceptable salt thereof.

2. The compound of claim 1, wherein a, b, c, d, e, $R^1$, and $R^2$ are H, and A is OH.

3. The compound of claim 1, wherein at least one of B and B' is:

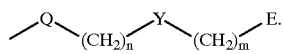

4. The compound of claim 3, wherein Q is C=O, Y is O or S, m and n are the same or different and each is 0 or 1, and E is $R^9$.

5. The compound of claim 4, wherein Y is O, and at least one of B or B'is:

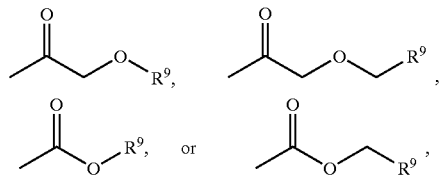

wherein $R^9$ is a heterocycloalkyl having 6 atoms, at least two of which are heteroatoms, in the ring skeleton thereof, a phenyl, a naphthyl, or a heteroaryl having 6 atoms, at least two of which are heteroatoms, in the ring skeleton thereof, wherein $R^9$ is unsubstituted or is substituted with one or more substituents selected from the group consisting of $R^7$, $OR^7$, $SR^7$, $NR^7R^8$, $COR^7$, $CSR^7$, $CO_2R^7$, $C(O)SR^7$, $C(S)$ $OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C$ $(O)SR^8$, $NR^7CS_2R^7$, $O_2CR^7$, $S_2CR^7$, $SCOR^7$, $OCSR^7$, $SO_2R^7$, $OSO_2R^7$, $NR^8SO_2R^7$, a guanidyl, CN, $NO_2$, $N_3$, and halogens, wherein $R^7$ and $R^8$ are the same or different and each is H, an unsubstituted $C_1$–$C_{20}$ alkyl or a $C_1$–$C_{20}$ alkyl substituted with one or more halogen atoms.

6. The compound of claim 5, wherein $R^9$ is selected from the group consisting of 2-methylphenyl, 2,6-dimethylphenyl, 3-amino-2-methylphenyl, 3-acetamido-2-methylphenyl, 3-hydroxy-2-methylphenyl, 4-hydroxy-2-methylphenyl, 4-amino-2-methylphenyl, 3-acetamido-2-methylphenyl, 4-methoxy-2-methylphenyl, 4-fluoro-2-methylphenyl, 4-trifluoromethyl-2-methylphenyl, 2,4-dimethylphenyl, 2-methyl-4-nitrophenyl, 3-amino-2,6-dimethylphenyl, 3-hydroxy-2,6-dimethylphenyl, 2-methyl-3-nitrophenyl, 4-acetyl-2-methylphenyl, 4-aminocarbonyl- 2-methylphenyl, benzopiperazinyl, tert-butyl, hydroxy tert-butyl, and morpholinyl.

7. The compound of claim 1, wherein B or B' is:

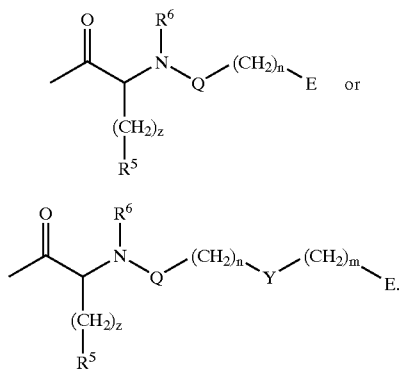

8. The compound of claim 7, wherein B or B' is of formula (Ic), Q is C=O, n is 0 and E is $R^9$, wherein $R^9$ is a heterocycloalkyl having 6 atoms, at least two of which are heteroatoms, in the ring skeleton thereof.

9. The compound of claim 8, wherein $R^9$ is a morpholinyl substituent.

10. The compound of claim 7, wherein:

z is 0 or 1;

$R^5$ is an unsubstituted $C_1$–$C_{20}$ alkyl or a $C_1$–$C_{20}$ alkyl substituted with one or more substituents selected from the group consisting of $R^7$, $OR^7$ and $C(O)NR^7R^8$;

$R^6$ is H;

Q is C=O;

Y is O or S;

m and n are the same or different and each is 0 or 1; and

E is $R^9$, wherein $R^9$ is a phenyl, a naphthyl or a heteroaryl having 6 atoms, at least two of which are heteroatoms, in the ring skeleton thereof, wherein $R^9$ is unsubstituted or is substituted with one or more substituents selected from the group consisting of $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, a guanidyl, CN, $NO_2$, $N_3$, and halogens;

wherein $R^7$ and $R^8$ are the sane or different and each is H, an unsubstituted $C_1$–$C_{20}$ alkyl or a $C_1$–$C_{20}$ alkyl substituted with one or more halogens.

11. The compound of claim 10, wherein B or B' is of the formula (Id), wherein z is 0, $R^5$ is isopropyl, Y is O, m is 1, and n is 0, such that B or B' is:

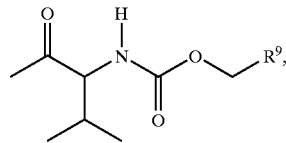

wherein $R^9$ is phenyl, which is unsubstituted or is substituted with one or more substituents selected from the group consisting of $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, a guanidyl, CN, $NO_2$, $N_3$, and halogens, wherein $R^7$ and $R^8$ are the same or different and each is H, an unsubstituted $C_1$–$C_{20}$ alkyl or a $C_1$–$C_{20}$ alkyl substituted with one or more halogens.

12. The compound of claim 1, wherein B or B' is of the formula (Ie), wherein L i's NH, z is 0, and $R^5$ is isopropyl such that B or B' is:

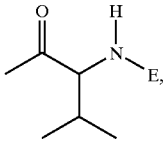

wherein E is H, $COR^9$, or $SO_2R^9$, wherein $R^9$ is methyl.

13. The compound of claim 1, wherein B or B' is:

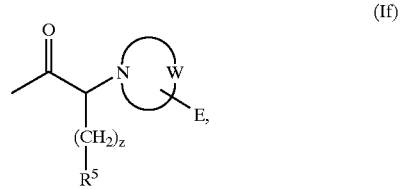

wherein the heterocycle:

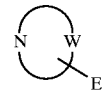

of formula (If) is unsubstituted or substituted with one or more substituents selected from the group consisting of $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$; $SCOR^7$, $OCSR^7$, $SO_2R^7$, $OSO_2R^7$, $NR^8SO_2R^7$, CN, $NO_2$, $N_3$, and halogens, wherein $R^7$ and $R^8$ are the same or different and each is H, an unsubstituted $C_1$–$C_{20}$ alkyl or a $C_1$–$C_{20}$ alkyl substituted with one or more halogen atoms.

14. The compound of claim 13, wherein W is of the formula —$(CH_2)_2O(CH_2)_2$—, —$(CH_2)_2S(CH_2)_2$—, —$(CH_2)_2SO(CH_2)_2$—, —$(CH_2)_2SO_2(CH_2)_2$—, or —$(CH_2)_2NH(CH_2)_2$—, wherein W is unsubstituted or substituted.

15. The compound of claim 13, z is 0, $R^5$ is isopropyl, and W of formula (If) is an organic residue that defines a heterocycle such that B or B' is of the formula:

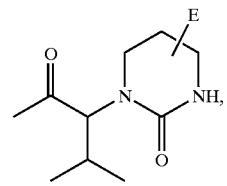

wherein said heterocycle is unsubstituted or substituted with one or more substituents selected from the group consisting of $R^7$, $OR^7$, $SR^7$, $NR^7R^8$, $COR^7$, $CSR^7$, $CO_2R^7$, $C(O)SR^7$, $C(S)OR^7$, $CS_2R^7$, $C(O)NR^7R^8$, $NHC(O)NR^7R^8$, $C(S)NR^7R^8$, $NHC(S)NR^7R^8$, $NR^8COR^7$, $NR^8CSR^7$, $NR^8CO_2R^7$, $NR^8C(O)SR^7$, $NR^8CS_2R^7$, $O_2CR^7$, $S_2CR^7$, $SCOR^7$, $OCSR^7$, $SO_2R^7$, $OSO_2R^7$, $NR^8SO_2R^7$, CN, $NO_2$, $N_3$, and halogens, wherein $R^7$ and $R^8$ are the same or different and each is H, an unsubstituted $C_1$–$C_{20}$ alkyl or a $C_1$–$C_{20}$ alkyl substituted with one or more halogen atoms.

16. The compound of claim 3, wherein B or B' is:

(Ib)

wherein:
Q is $SO_2$ or C=O;
m and n are the same or different and are each 0 or 1; and
Y is a $C_6$–$C_{15}$ aryl or a heteroaryl having 6 atoms, at least two of which are heteroatoms, in the ring skeleton thereof, wherein Y is unsubstituted or substituted.

17. The compound of claim 16, wherein Q is C=O; m and n are 0; and Y is an unsubstituted phenyl or a substituted phenyl such that B or B' is:

wherein E is H, $NR^9R^{10}$, $NHCO_2(CH_2)_qR^9$, $NHC(O)N[(CH_2)_qR^9]R^{10}$, $NHC(S)N[(CH_2)_qR^9]R^{10}$, $NR^{10}CO[(CH_2)_qR^9]$, $NR^{10}CS[(CH_2)_qR^9]$, $NR^{10}CO_2[(CH_2)_qR^9]$, $NR^{10}C(O)S[(CH_2)_qR^9]$, $NR^{10}CS_2[(CH_2)_qR^9]$, $NR^{10}SO_2[(CH_2)_qR^9]$, CN, $NO_2$, $N_3$, or a halogen.

18. The compound of claim 17, wherein E is $NHCO_2(CH_2)_qR^9$, wherein q is 0 or 1, and $R^9$ is a phenyl.

19. The compound of claim 1, wherein B is bonded to the nitrogen atom bearing $R^1$ via an amide bond and is selected from the group consisting of:

wherein B' is bonded to the nitrogen bearing $R^2$ via an amide bond and is selected from the group consisting of:

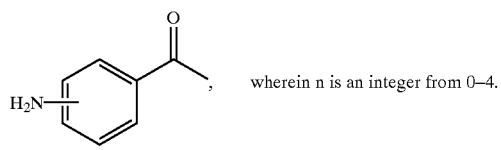, wherein n is an integer from 0–4.

20. The compound of claim 1, wherein B and B' are the same or different and each is bonded to the nitrogen bearing $R^1$ and $R^2$, respectively, via an amide bond, and each is selected from the group consisting of:

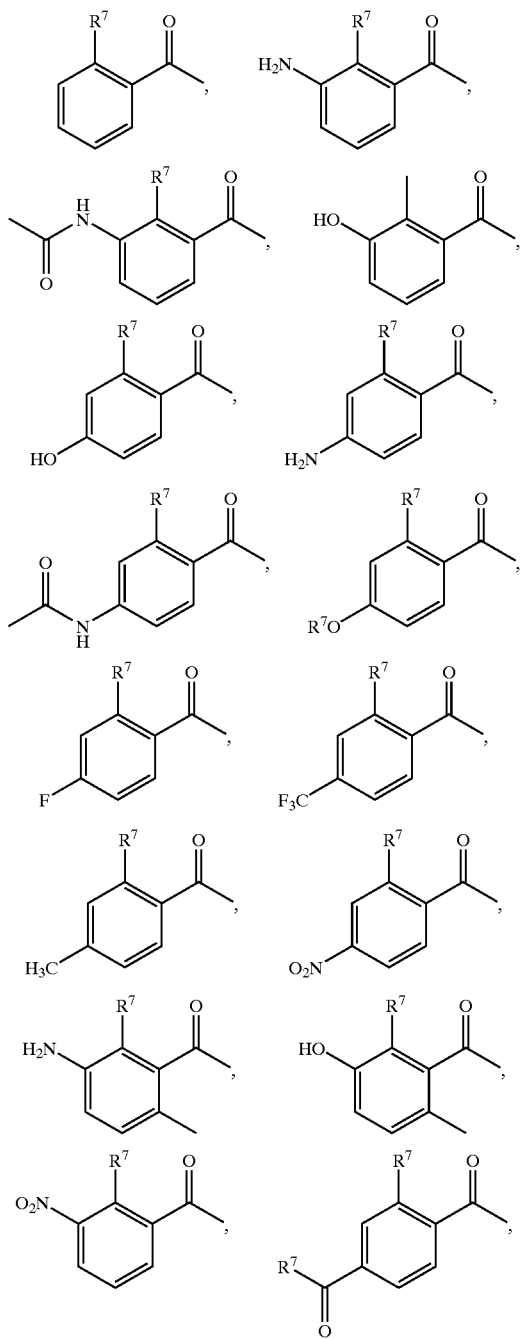

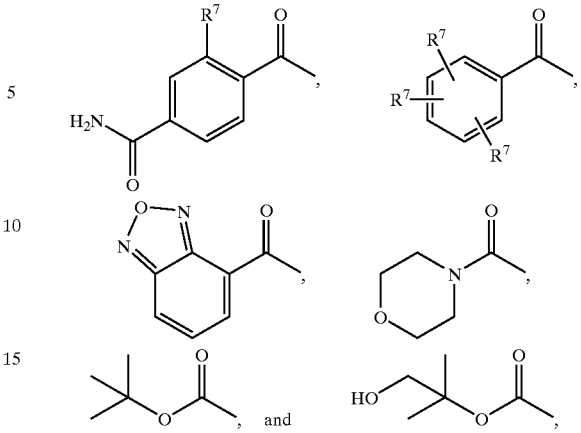

wherein $R^7$ is H, an unsubstituted $C_1$–$C_{20}$ alkyl or a $C_1$–$C_{20}$ alkyl substituted with one or more halogens, wherein each occurrence of $R^7$ is the same or different when said compound is substituted with two or more $R^7$ substituents.

21. The compound of claim 20, wherein B and B' are the same or different and each is of the formula:

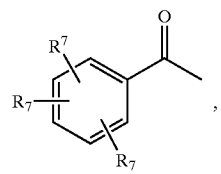

wherein $R^7$ is H, an unsubstituted $C_1$–$C_{20}$ alkyl or a $C_1$–$C_{20}$ alkyl substituted with one or more halogens and each occurrence of $R^7$ on said compound is the same or different.

22. The compound of claim 1, wherein B and $R^1$ together with the nitrogen atom to which they are bonded comprise a heterocycle, having 6 atoms, at least two of which are heteroatoms, in the ring skeleton thereof, of the formula:

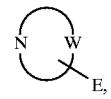

such that said compound is of the formula:

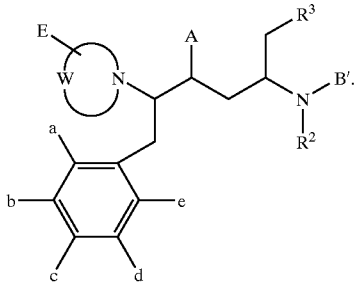

(Ig)

23. The compound of claim 22, wherein W is of the formula —(CH$_2$)$_2$O(CH$_2$)$_2$—, —(CH$_2$)$_2$S(CH$_2$)$_2$—, —(CH$_2$)$_2$SO(CH$_2$)$_2$—, —(CH$_2$)$_2$SO$_2$(CH$_2$)$_2$—, or —(CH$_2$)$_2$NH(CH$_2$)$_2$—, wherein W is unsubstituted or substituted.

24. The compound of claim 1, wherein B' and $R^2$ together with the nitrogen atom to which they are bonded comprise a heterocycle, having 6 atoms in the ring skeleton thereof, of the formula:

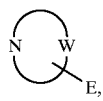

such that said compound is of the formula:

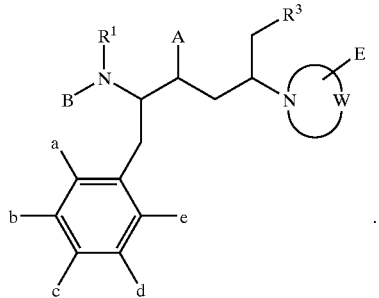

(Ih)

25. The compound of claim 24, wherein W is of the formula —(CH$_2$)$_2$O(CH$_2$)$_2$—, —(CH$_2$)$_2$S(CH$_2$)$_2$—, —(CH$_2$)$_2$SO(CH$_2$)$_2$—, —(CH$_2$)$_2$SO$_2$(CH$_2$)$_2$—, or —(CH$_2$)$_2$NH(CH$_2$)$_2$—, wherein W is unsubstituted or substituted.

26. A composition comprising a carrier and a therapeutically effective amount of at least one compound of claim 1.

27. A method of treating an HIV infection comprising administering a therapeutically effective amount of at least one compound of claim 1.

28. A method of treating cancer comprising administering a cathepsin D inhibiting-effective amount of at least one compound of claim 1.

29. The method of claim 28, wherein said cancer is breast cancer.

30. A method of treating a malarial infection comprising administering a plasmepsin inhibiting-effective amount of at least one compound of claim 1.

31. A compound having the core structure:

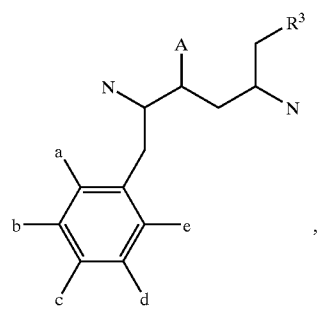

wherein
a, b, c, d, and e, are the same or different and each is H, R$^7$, OR$^7$, SR$^7$, NR$^7$R$^8$, NHCOR$^7$, CO$_2$R$^7$, CN, NO$_2$, NH$_2$, N$_3$, or a halogen, wherein R$^7$ and R$^8$ are the same or different and each is H, an unsubstituted alkyl, or a substituted alkyl;
R$^3$ is isopropyl, wherein R$^3$ is unsubstituted or substituted; and
A is OH, NH$_2$, or SH.

* * * * *